United States Patent [19]

Sprecker et al.

[11] 4,275,251

[45] Jun. 23, 1981

[54] SUBSTITUTED TRICYCLODECANE DERIVATIVES, PROCESSES FOR PRODUCING SAME AND ORGANOLEPTIC USES THEREOF

[75] Inventors: Mark A. Sprecker, Sea Bright; John B. Hall, Rumson, both of N.J.

[73] Assignee: International Flavors & Fragrances Inc., New York, N.Y.

[21] Appl. No.: 144,898

[22] Filed: Apr. 29, 1980

[51] Int. Cl.³ .............................................. C07C 35/22
[52] U.S. Cl. .................................... 568/817; 568/816; 568/369; 568/463; 252/522 R
[58] Field of Search ................ 260/463; 568/817, 816; 252/522

[56] References Cited

U.S. PATENT DOCUMENTS

| | | | |
|---|---|---|---|
| 3,271,259 | 9/1966 | Arctander | 568/817 |
| 3,748,284 | 7/1973 | Crossman | 252/522 |
| 3,989,760 | 11/1976 | Light et al. | 568/817 |
| 4,123,394 | 10/1978 | Skerianetz et al. | 568/817 |

FOREIGN PATENT DOCUMENTS 22330 2/1977 Australia .
815232 1/1959 United Kingdom .

OTHER PUBLICATIONS

Buchi et al., "J Amer. Chem. Soc.," vol. 83, p. 927, (1961).
Kheiseter et al., "Chem. Abst.", vol. 61, p. 8199e, (1964).
Hoffman et al., "Chem. Abst.", vol. 91, p. 56477g, (1979).
Zeinalov et al., "Chem. Abst.", vol. 68, p. 49319d, (1960).
Opdyke, "Chem. Abst.", vol. 92, p. 11070y, (1980).
Arctandy, "Perfume and Flavor Chem., (Aroma Chem.), (1969), p. 1582.

Primary Examiner—Werren B. Lone
Attorney, Agent, or Firm—Arthur L. Liberman

[57] ABSTRACT

Described are substituted tricyclodecane derivatives having the generic structure:

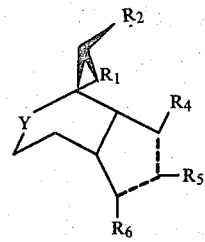

wherein Y is a moiety having a structure selected from the group consisting of:

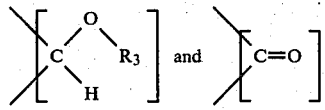

wherein one of the dashed lines represents a carbon-carbon single bond and the other of the dashed lines represents a carbon-carbon double bond; wherein $R_1$ and $R_2$ represent hydrogen or methyl with the proviso that one of $R_1$ and $R_2$ is hydrogen and the other of $R_1$ and $R_2$ is methyl; wherein $R_3$ is hydrogen, $C_1$–$C_3$ acyl, $C_3$ or $C_4$ alkyl or $C_3$ or $C_4$ alkenyl; wherein $R_4$, $R_5$ and $R_6$ represent hydrogen or methyl with the additional proviso that one of $R_4$, $R_5$ and $R_6$ is methyl and the other two of $R_4$, $R_5$ and $R_6$ is hydrogen. Also described are processes for preparing such substituted tricyclodecane derivatives and processes for using the above defined substituted tricyclodecane derivatives for their organoleptic properties and compositions containing said substituted tricyclodecane derivatives including perfumes, perfumed articles, such as solid or liquid anionic, cationic, nonionic and zwitterionic detergents, fabric softeners and cosmetic powders; foodstuffs, chewing gums, toothpastes, medicinal products and chewing tobaccos; smoking tobacco compositions and smoking tobacco flavoring compositions and smoking tobacco articles containing such smoking tobacco compositions.

2 Claims, 35 Drawing Figures

NMR SPECTRUM FOR EXAMPLE I.

GLC PROFILE FOR EXAMPLE II.

GLC PROFILE FOR EXAMPLE I.

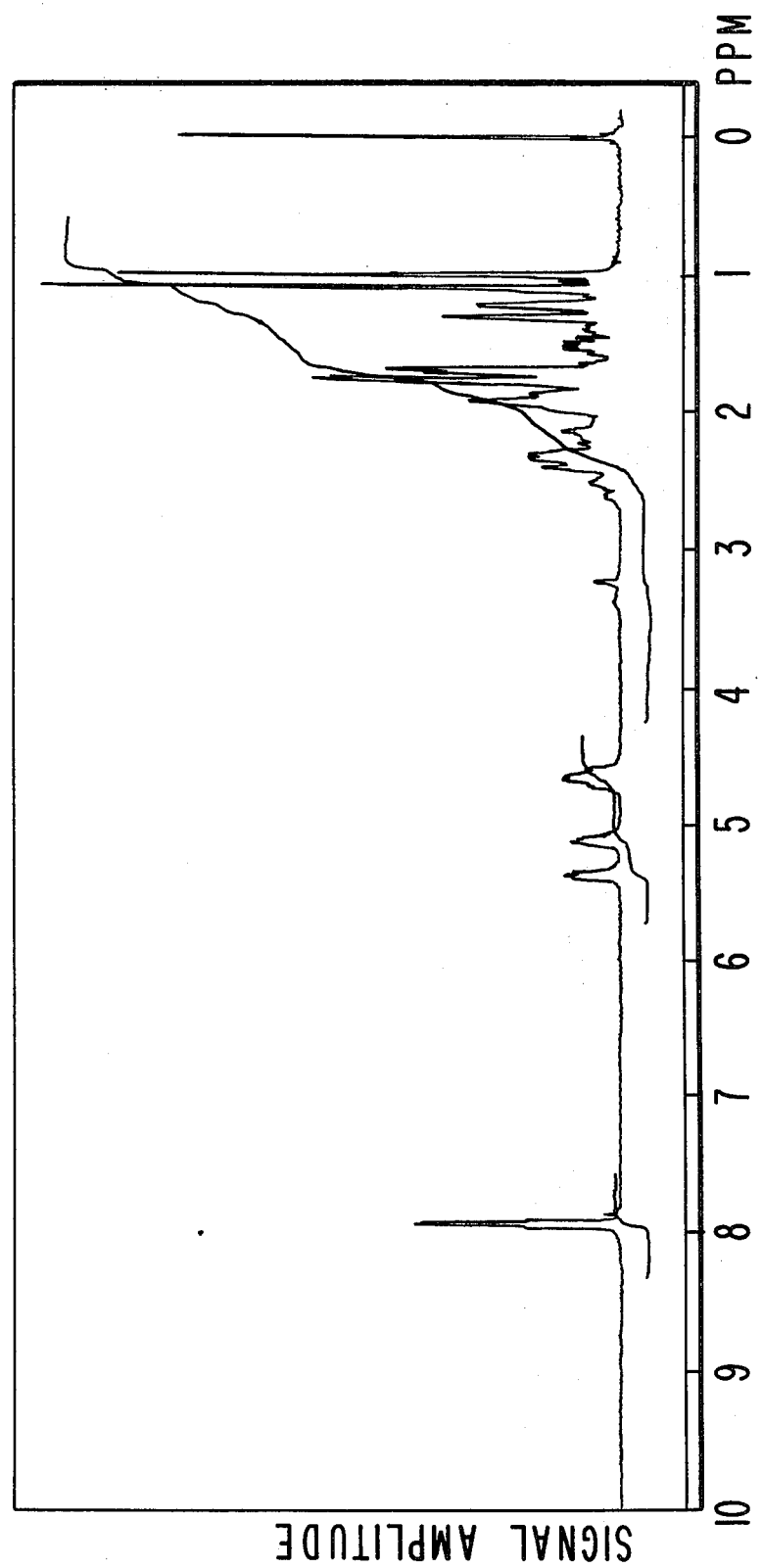

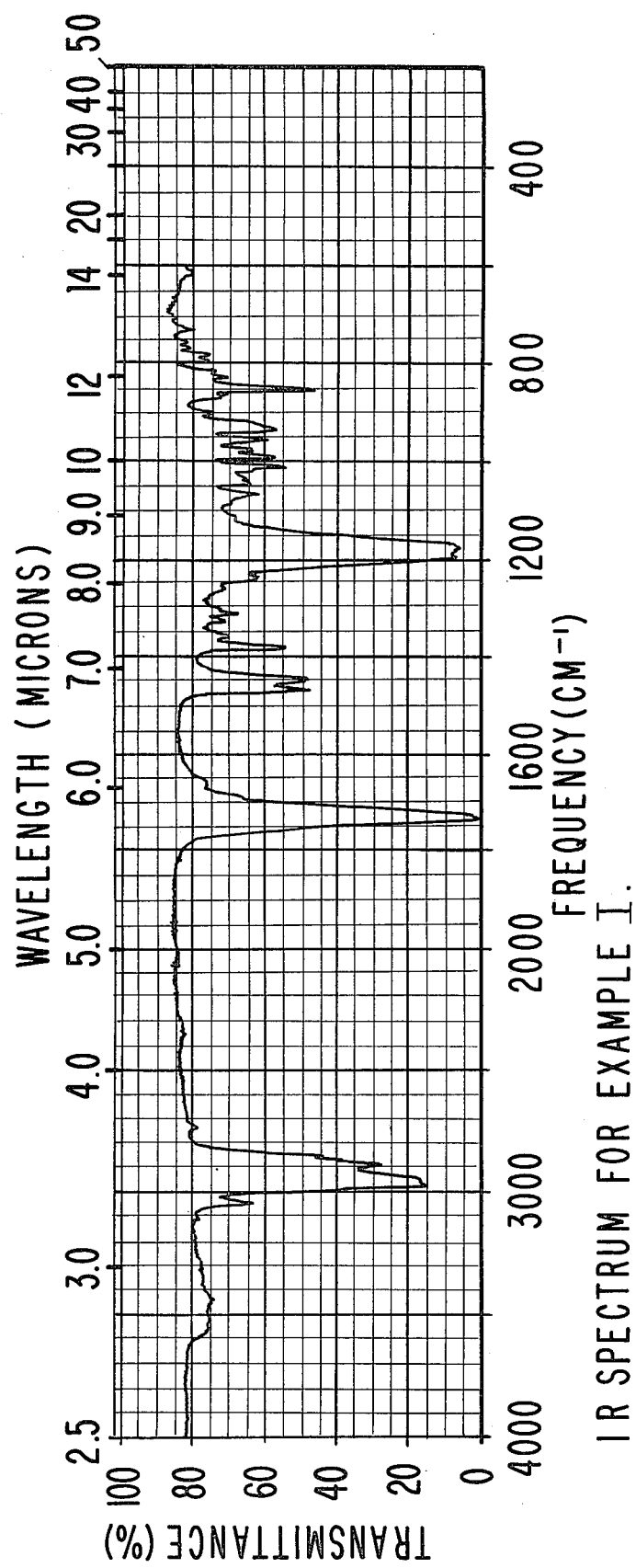

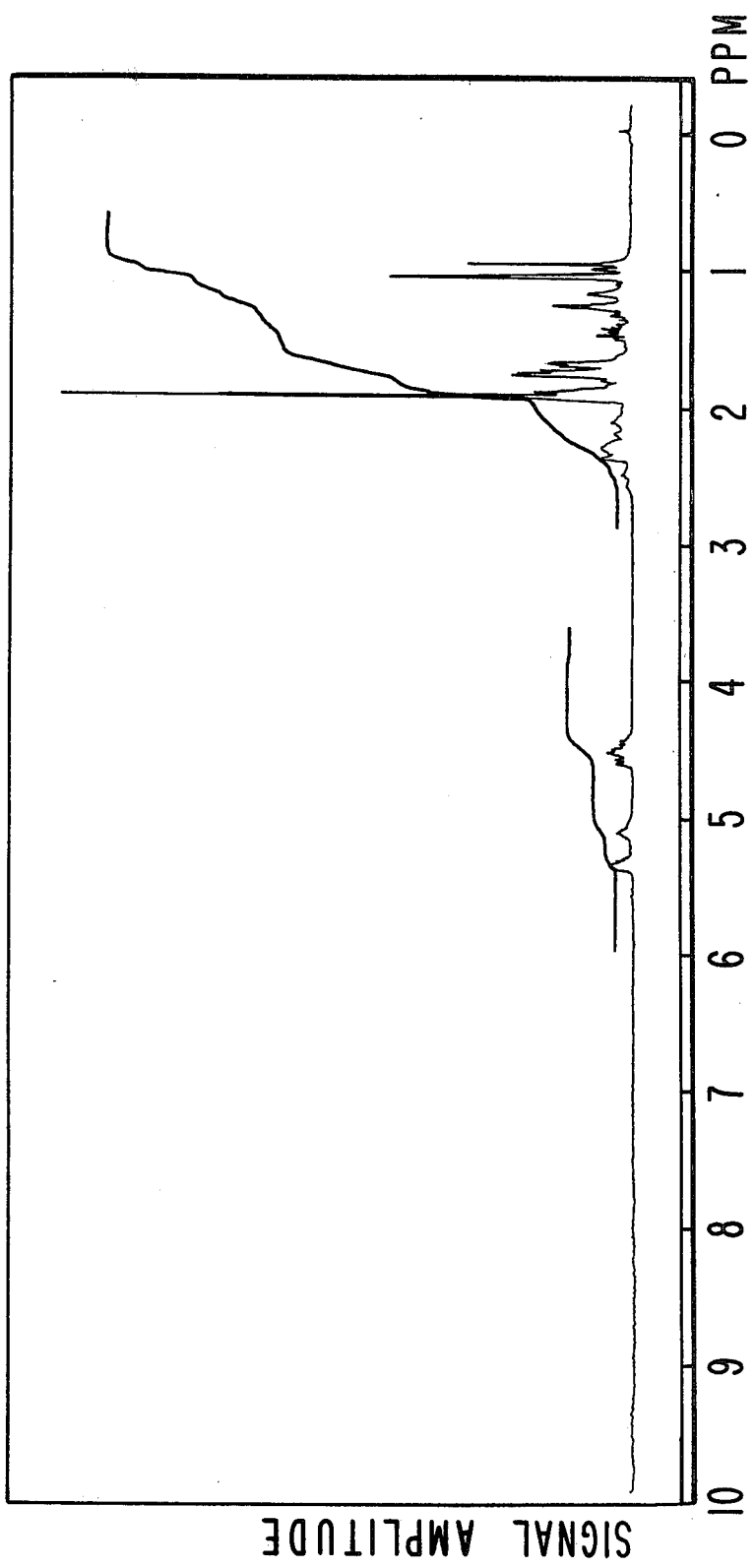

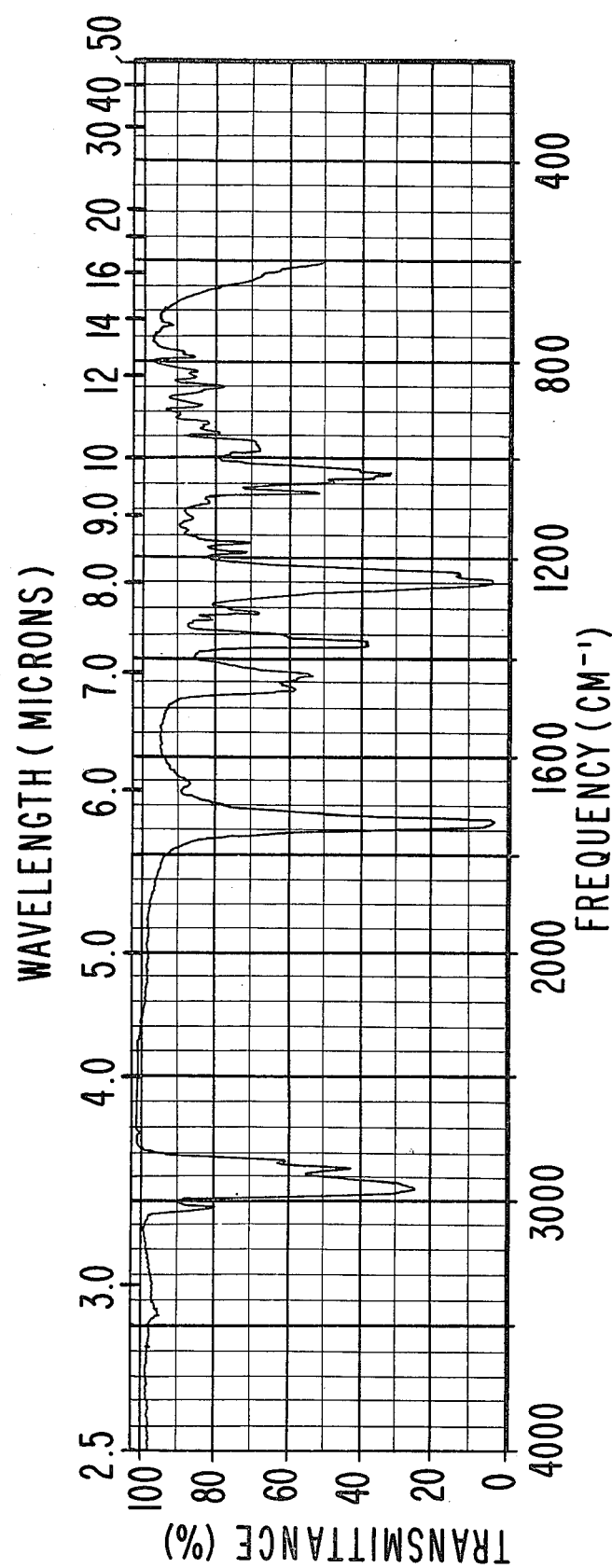

GLC PROFILE FOR EXAMPLE IV.

GLC PROFILE FOR EXAMPLE III.

NMR SPECTRUM FOR EXAMPLE III.

IR SPECTRUM FOR EXAMPLE III.

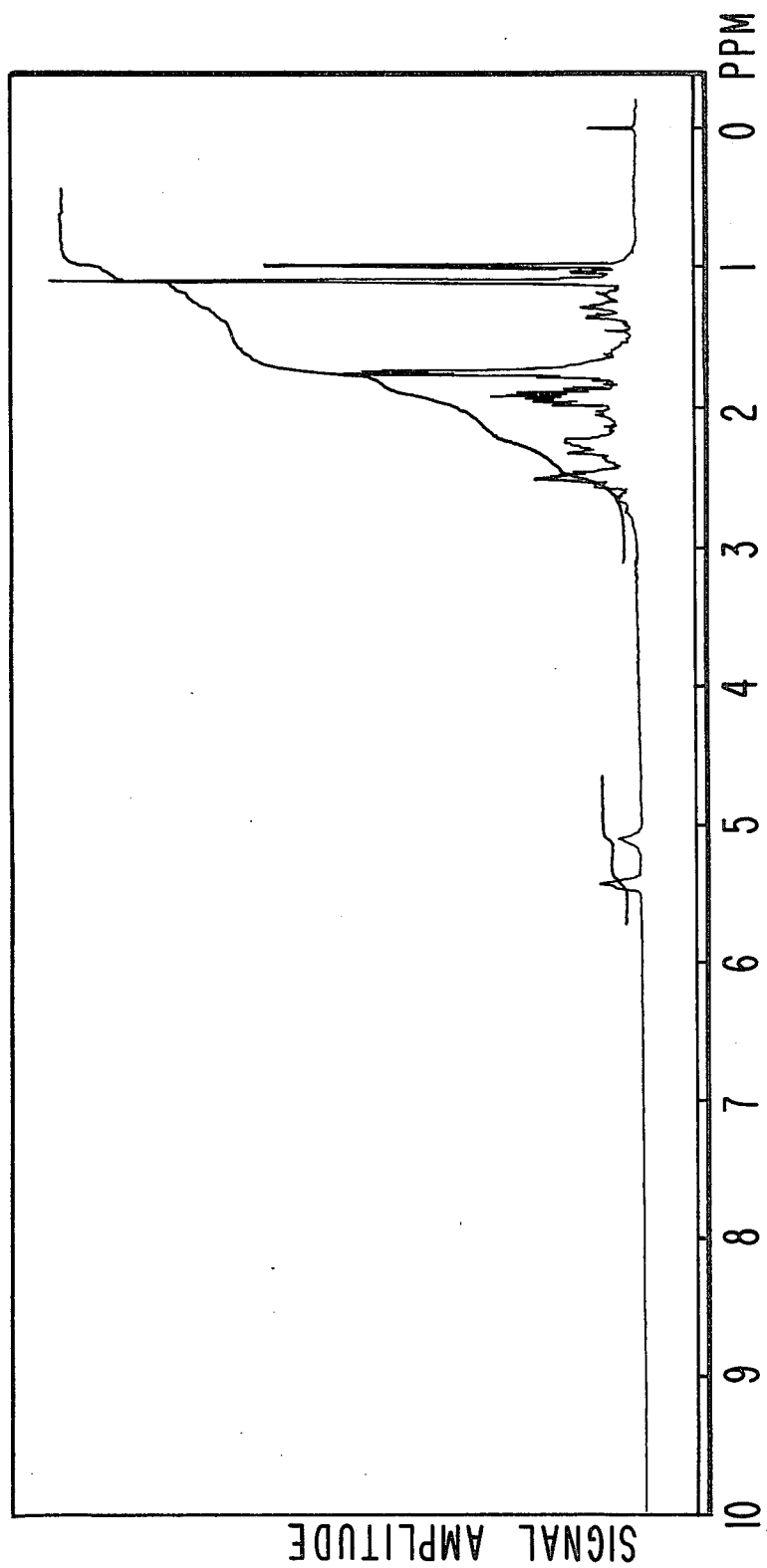

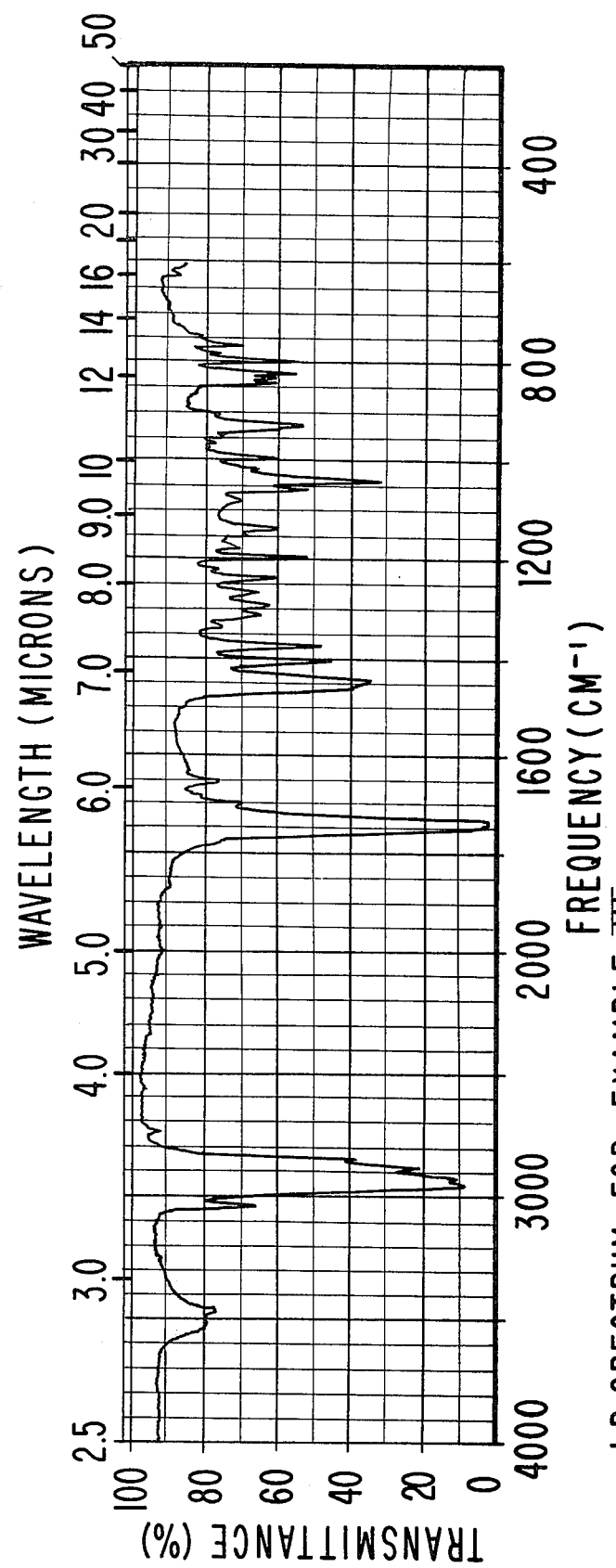
FIG.12 IR SPECTRUM FOR EXAMPLE VI.

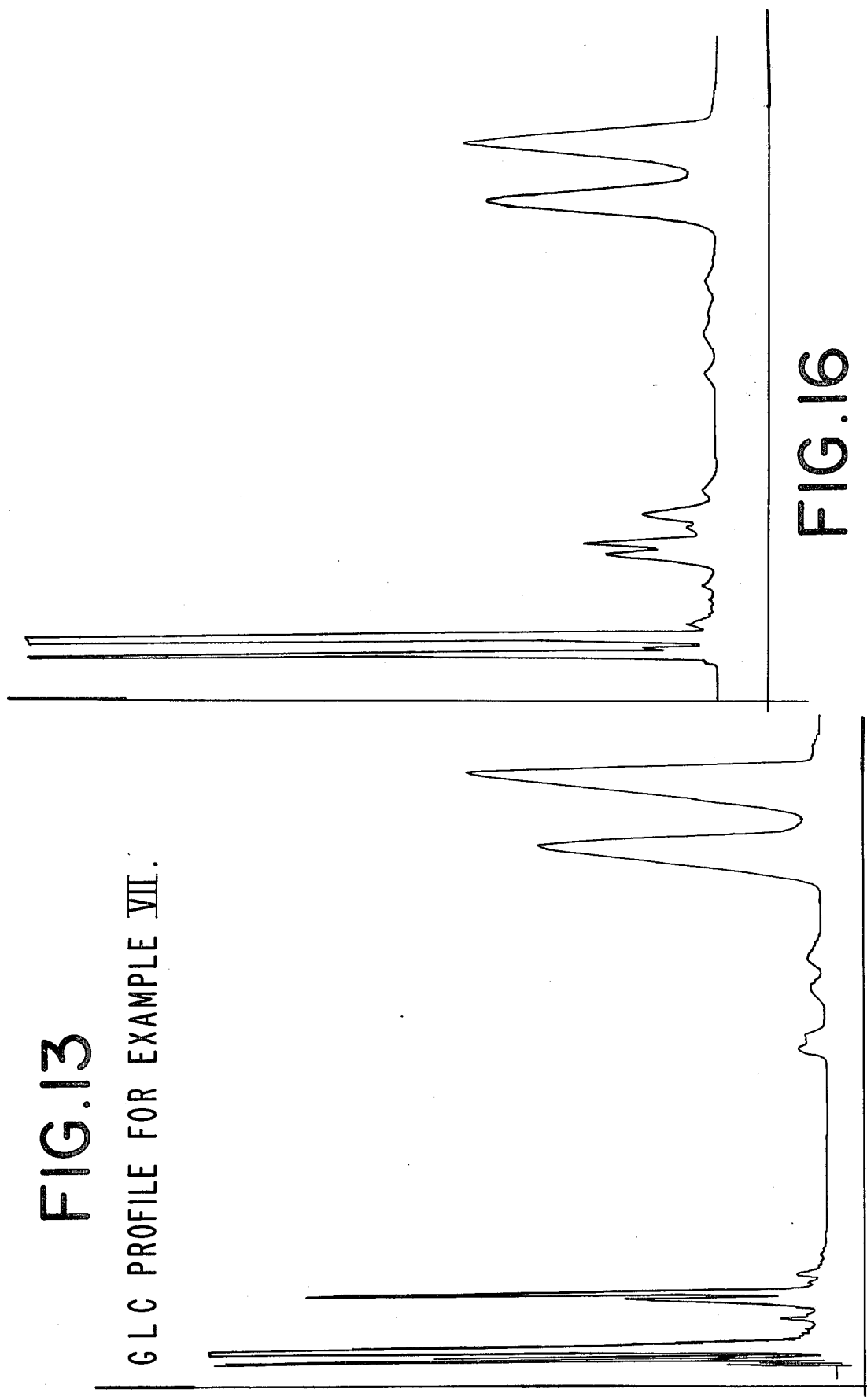

NMR SPECTRUM FOR EXAMPLE VII.

IR SPECTRUM FOR EXAMPLE VII.

NMR SPECTRUM FOR EXAMPLE VIII.

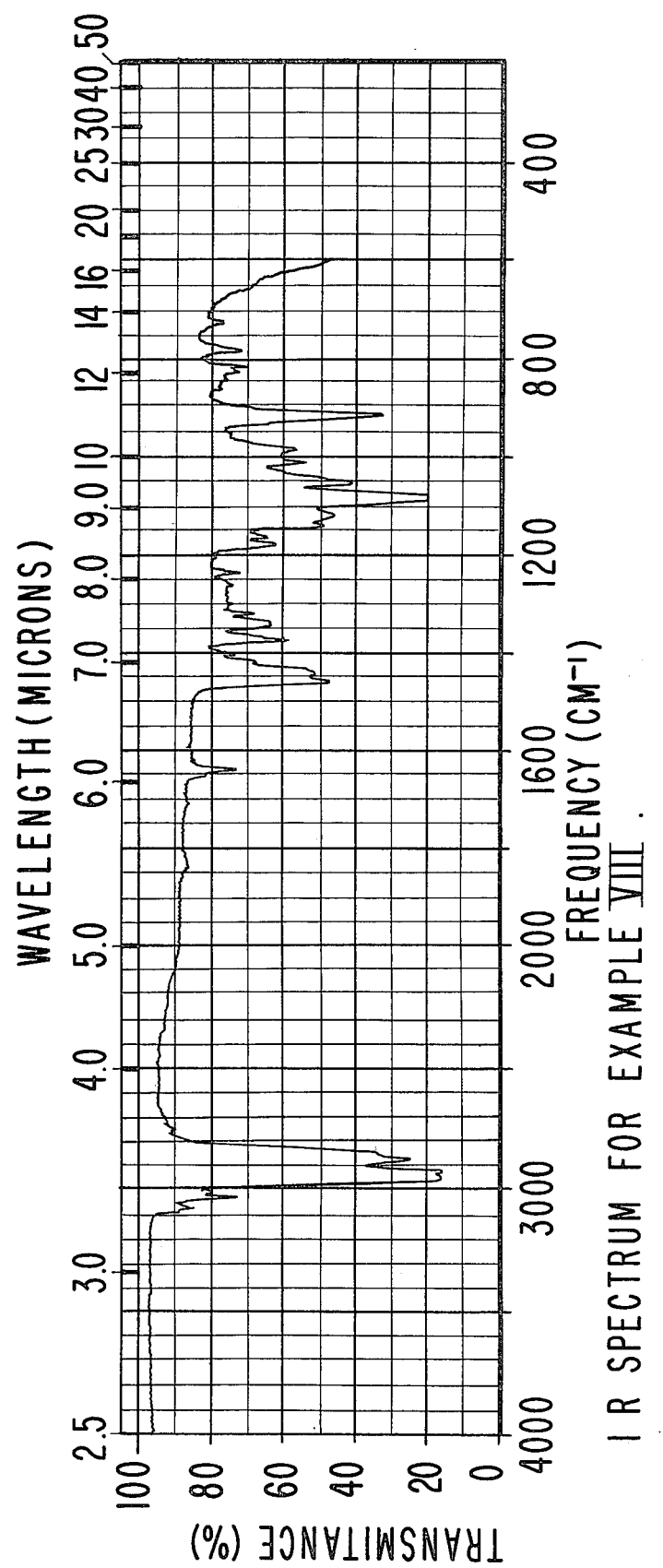

GLC PROFILE FOR EXAMPLE X.

GLC PROFILE FOR EXAMPLE IX.

NMR SPECTRUM FOR EXAMPLE IX.

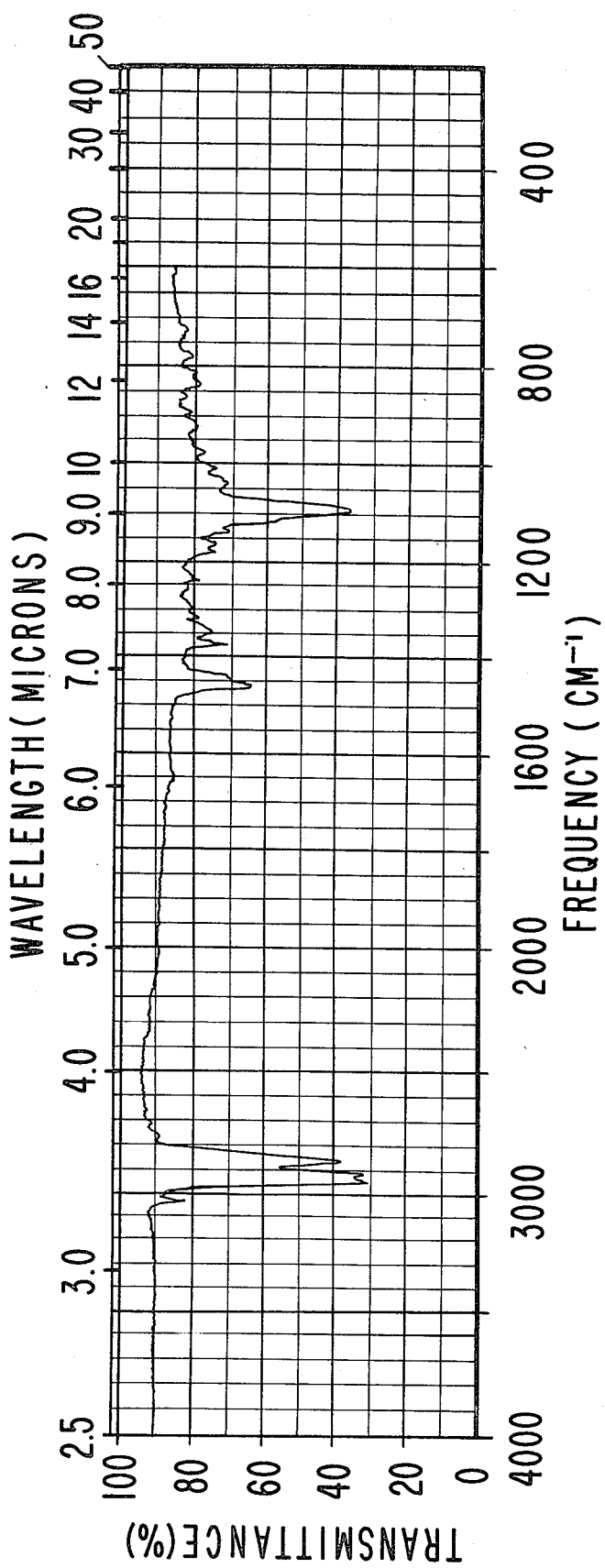

NMR SPECTRUM FOR EXAMPLE X.

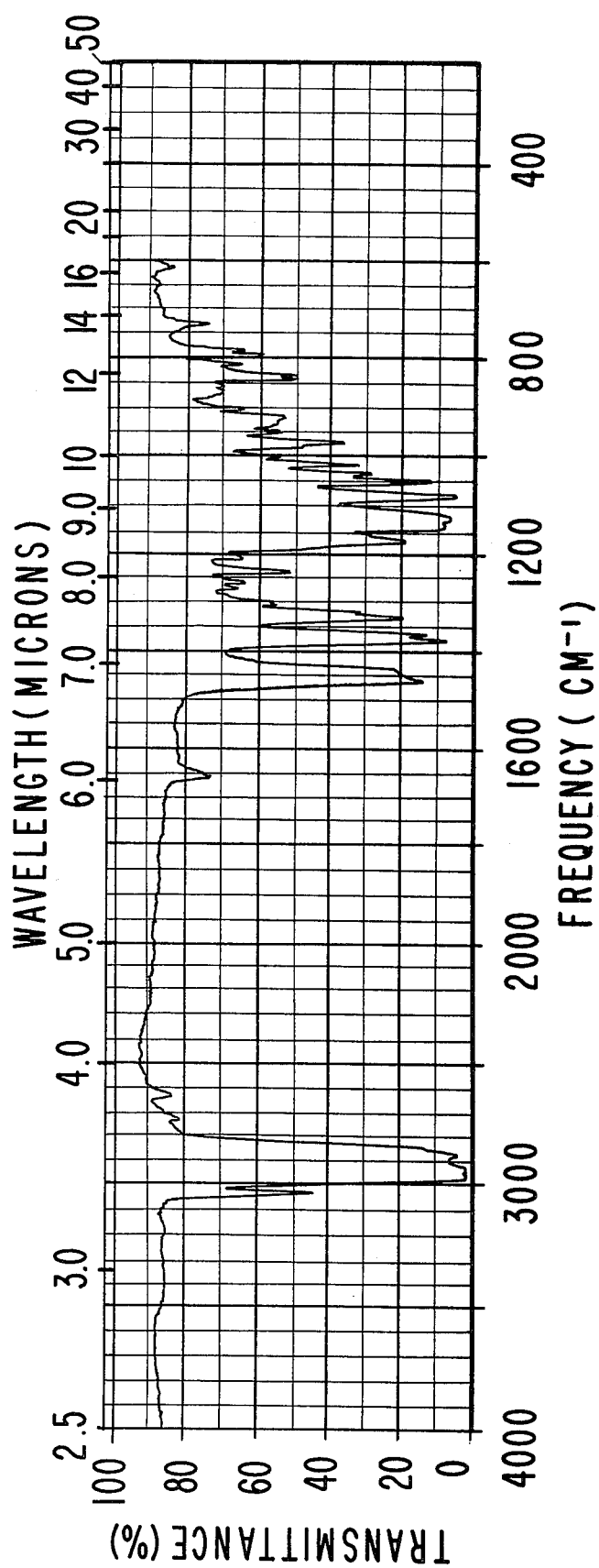

GLC PROFILE FOR EXAMPLE XII.

GLC PROFILE FOR EXAMPLE IV.

NMR SPECTRUM FOR PEAK I OF EXAMPLE IV.

FIG. 27 NMR SPECTRUM FOR PEAK 2 OF EXAMPLE IV.

IR SPECTRUM FOR PEAK 3 OF EXAMPLE IV.

NMR SPECTRUM FOR EXAMPLE XI

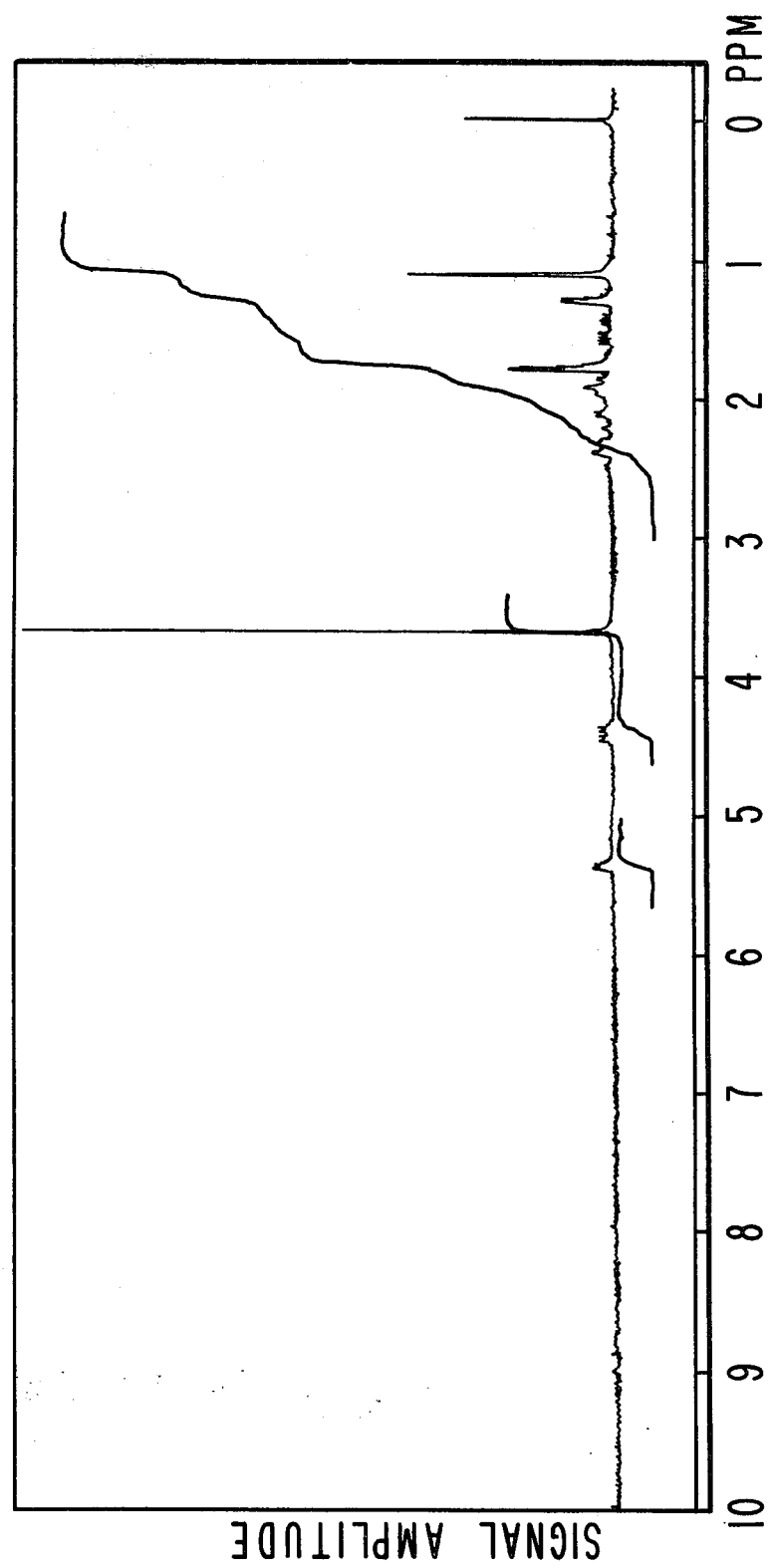
FIG.33 NMR SPECTRUM FOR FRACTION 5 OF EXAMPLE XII.

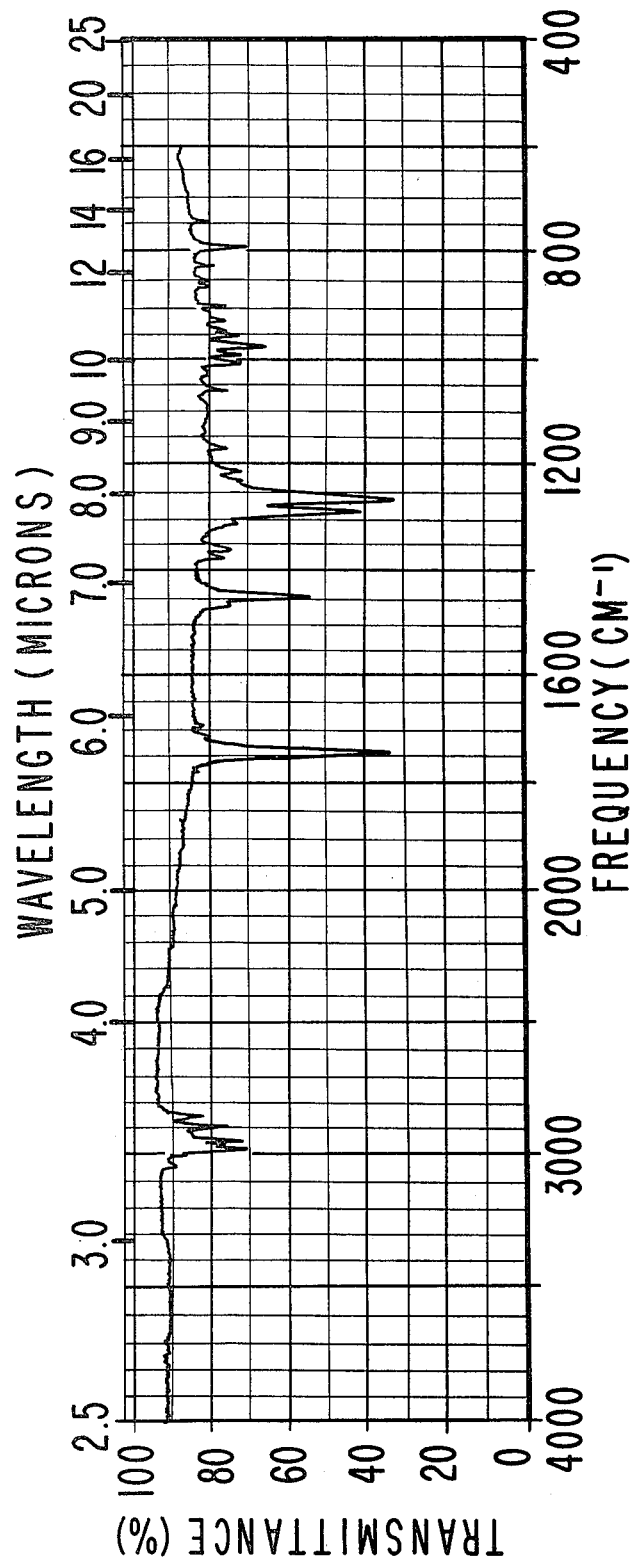

MASS SPECTRUM FOR FRACTION 5 OF EXAMPLE XII.

SUBSTITUTED TRICYCLODECANE DERIVATIVES, PROCESSES FOR PRODUCING SAME AND ORGANOLEPTIC USES THEREOF

BACKGROUND OF THE INVENTION

Materials including mixtures of natural products which can provide patchouli-like, green, floral, musty/camphoraceous, rosey, woody, anisic, ionone-like, fruity (banana-like), spicey (cinnamon-like), bitter sweet, milky, petitgrain-like, lavender, bergamot-like, fatty and minty fragrance notes are known in the art of perfumery. Many of the natural materials which provide such fragrances and contribute desired nuances to perfumery compositions are high in cost, vary in quality from one batch to another and/or are generally subject to the usual variations in natural products.

There is, accordingly, a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined patchouli-like fragrance, for example, has been difficult and relatively costly in the areas of both natural products and synthetic products.

Thus, Light, et al in U.S. Pat. No. 3,989,760 provides processes and compositions for altering the flavor and-/or aroma of consumable products, including foods, tobacco and perfumes, particularly, perfumes having a patchouli aroma, utilizing as the essential ingredient the organic tricyclic alcohol having the formula:

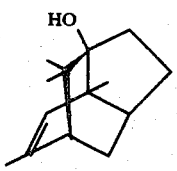

Buchi, et al., 83 J.Am.Chem.Soc. 927 (1961), shows the production of a material called "patchoulione" which is stated to be octahydro-1,4,9,9-tetramethyl-3a,7-methanoazulen-5-(4H)-one having the structure:

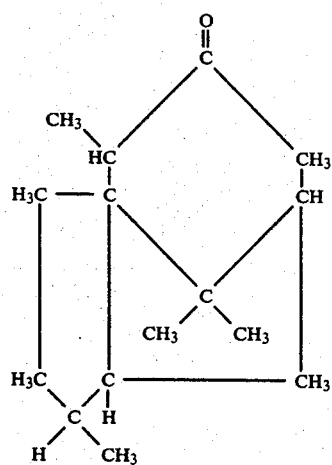

U.S. Pat. No. 3,748,284 issued on July 24, 1973 discloses perhydro derivatives of methanoazulen as having camphoraceous woody fragrances and having the ability to impart this fragrance to perfumed compositions and perfumed articles. The compounds disclosed are:
a. Octahydro-1,4,9,9-tetramethyl-4,7-methanoazulen-3(2H)-one;
b. Octahydro-1,4,9,9-tetramethyl-4,7-methanoazulen-2(3H)-one; and
c. Octahydro-1,4,9,9-tetramethyl-4,7-methanoazulen-8(7H)-one.

Umarani, et al., Sept./Oct. 1969, P. & E.O.R., 307 discloses two compounds relevant to the instant case:
"isopatchoulinol" having the structure:

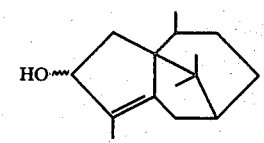

and "patchouli alcohol" having the structure:

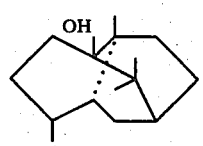

In addition, artificial flavoring agents for foodstuffs have received increasing attention in recent years. In many years, such food flavoring agents have been preferred over natural flavoring agents at least in part due to their diminished cost and their reproducible flavor qualities. For example, natural food flavoring agents such as extracts, concentrates and the like are often subject to wide variations due to changes in the quality, type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods is not completely known. This is noticeable in products having sweet, cocoa butter-like, herbaceous, green, floral and anise (licorice-like) flavoring and aroma characteristics.

Reproduction of sweet, cocoa-butter-like, herbaceous, green, floral and anise flavor and aroma characteristics has been the subject of long and continuing searches by those engaged in the production of foodstuffs and beverages. The severe shortage of food in many parts of the world has given rise to the development of previously unused sources of protein which are unpalatable. Accordingly, the need has arisen for the use of flavoring materials which will make such sources of protein palatable to human sensory organs.

Even more desirable is a product that can serve to substitute for difficult-to-obtain natural perfumery oils and at the same time substitute for natural flavoring oils and at the same time substitute for natural flavoring ingredients in both foodstuffs as well as tobacco. Cocoa-like, sweet, floral and green aroma and taste characteristics in smoking tobacco both prior to and on smoking in the main stream and in the side stream are particularly desirable for uses in conjunction with smoking tobacco and smoking tobacco articles, like cigarettes, cigars and the like.

Oxygenated compounds having a bicyclopentadiene nucleus are known in the prior art and uses thereof in perfumery are also known. Thus, for example, Kheisets and Virezub at Chem. Abstracts, 61, 8199c (Abstract of Zh.Obshch. Khim. 34 (6) 2081-4) discloses for use in perfumery compounds having the structure:

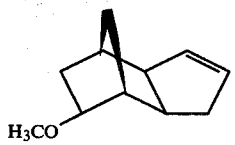

The Zeinalov, et al at Chem. Abstracts, 68, 49319d, discloses the compound having the structure:

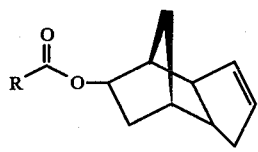

wherein R is methyl, n-propyl or n-butyl.

Opdyke in Chem. Abstracts, 92:11070y (Abstract of Food, Cosmet. Toxicol. 1976, 14, Suppl. 889) discloses the compound having the structure:

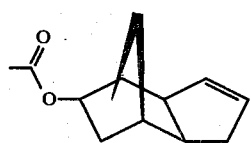

in fragrance raw materials and its toxicological properties.

For use in perfumery, U.S. Pat. No. 3,593,745 issued on Aug. 10, 1971 discloses the compound having the structure:

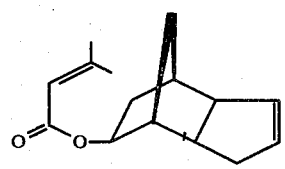

The compound having the structure:

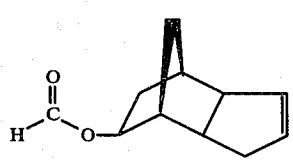

is disclosed in U.K. Pat. No. 815,232 issued on June 24, 1959.

Furthermore, the compound having the structure:

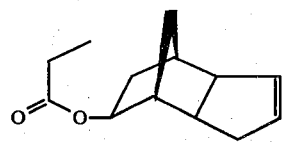

has been in use in the perfume industry for the past ten years and is known as "Cyclaprop".

German Offenlengungsschrift No. 2,642,519 published on Mar. 23, 1978 and abstracted in Chem. Abstracts, 91:56477g discloses for use in perfumery the compounds having the structures:

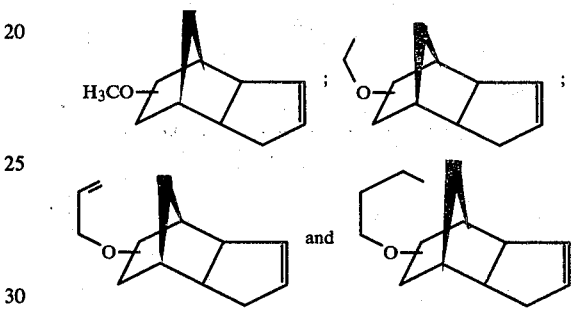

and generically the compound having the structure:

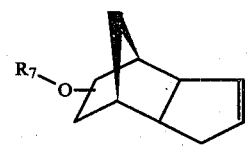

wherein $R_7$ is alkyl or alkenyl.

U.S. Pat. No. 4,123,394 issued on Oct. 31, 1978 discloses specifically the compound having the structure:

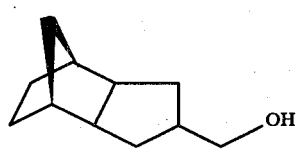

and generically the compound having the structure:

wherein $R_8$ is hydrogen, acyl, alkyl or alkenyl.

Arctander, "Perfume and Flavor Chemicals (Aroma Chemicals)", 1969 at monograph 1582 discloses 3a; 4,5,6,7,7a-hexahydro-4,7-methano-5-indano having the structure:

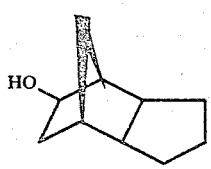

and indicates it to be a semi-solid crystalline mass or a viscous pale straw colored or almost colorless liquid having a peculiar earthy, sweet, musky odor of moderate tenacity. Arctander indicates that "a number of adducts and derivatives have been made and a few have become useful in perfume chemicals" and further that this material has notes in common with sandalwood, oakmoss, cedarwood and galbanum and it could be used in conjunction with certain materials. Arctander further states that this compound is stable in soap and offers a low cost material for soap, detergent and other household product fragrances and its musky character blends well with woody and amber-like notes but leaves a floral picture out of the question. Arctander further states that this material is rarely offered under its chemical name but it may enter various specialities and perfume bases as a minor component and during the 1965–1966 period of scarcity and high prices of patchouli oil, the subject alcohol found some uses in the creation of patchouli oil substitutes. Reference is made by Arctander to U.S. Pat. No. 3,271,259 issued on Sept. 6, 1966.

U.S. Pat. No. 3,271,259 issued on Sept. 6, 1966 entitled "Synthetic Lavandin Oil" discloses the use in perfumery of the compound having the structure:

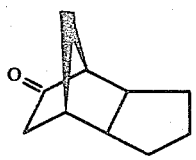

particularly in producing synthetic lavandin oil.

French Pat. No. 2,424,244 (corresponding to British Published Application 2,019,841) discloses 8-exo-hydroxymethyl-endo-tricyclodecanes useful as perfumery agents in soaps, shampoos, cosmetics and waxes wherein the fragrances range from green, green grass-like, fruit-like to wood-like. The generic structure of the compounds discloses in French Pat. No. 2,424,244 (assigned to Kao Soap Company of Japan) is:

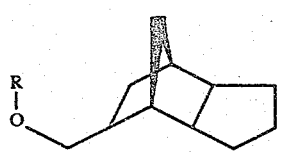

wherein R is unsaturated $C_1$–$C_5$ alkyl, $C_1$–$C_5$ acyl or oglycidyl and the esters are prepared from the compound wherein R is H by means of esterification with a carboxylic acid and a mineral acid catalyst and ethers are prepared from the compound wherein R equals H using a sodium hydride/alkyl iodide compound and the oglycidyl ethers are prepared from allyl ethers by treatment with peracids.

Australian Pat. No. AU-B1-22330/77 (506,675 filed on Feb. 16, 1977 and the abstract for which is published in Vol. 50, No. 1 of the Official Journal of Patents, Trademarks and Designs of Australia discloses a wood polymer composite comprising a wood substrate impregnated with a dicyclopentenyl acrylate or methacrylate polyer having as a repeating component:

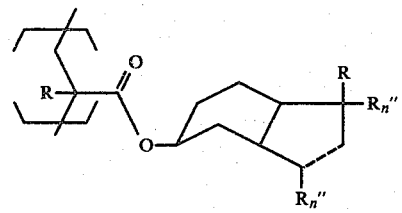

wherein R is hydrogen or methyl, R' and each R" are independently hydrogen, chlorine or bromine, n is 0 or 1, and the dashed line represents a carbon-carbn single bond or a carbon-carbon double bond with the proviso that when the dashed line is a carbon-carbon double bond, n is 0, but when the dashed line is a carbon-carbon single bond, n is 1. The Australian Patent, however, does not disclose any utilities of the monomeric precursor in perfumery.

The compound having the generic structure:

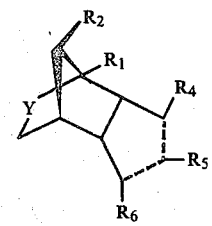

wherein Y is a moiety having a structure selected from the group consisting of:

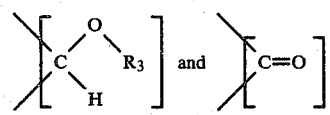

wherein one of the dashed lines represents a carbon-carbon single bond and the other of the dashed lines represents a carbon-carbon double bond; wherein $R_1$ and $R_2$ represent hydrogen or methyl with the proviso that one of $R_1$ and $R_2$ is hydrogen and the other of $R_1$ and $R_2$ is methyl; wherein $R_3$ is hydrogen, $C_1$–$C_3$ acyl, $C_3$ or $C_4$ alkyl or $C_3$ or $C_4$ alkenyl; wherein $R_4$, $R_5$ and $R_6$ represent hydrogen or methyl with the additional proviso that one of $R_4$, $R_5$ and $R_6$ is methyl and the other two of $R_4$, $R_5$ and $R_6$ is hydrogen have properties which are unexpected, unobvious and advantageous insofar as organoleptic uses are concerned when compared with the compounds of the prior art as discussed above.

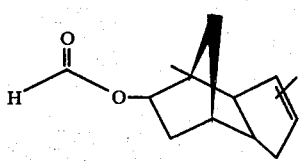

FIG. 2 represents the NMR spectrum for the reaction product of Example I containing the compound having the structure:

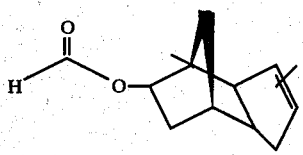

FIG. 3 represents the infrared spectrum for the compound having the structure:

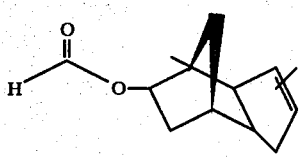

produced according to Example I.

Figure 4:
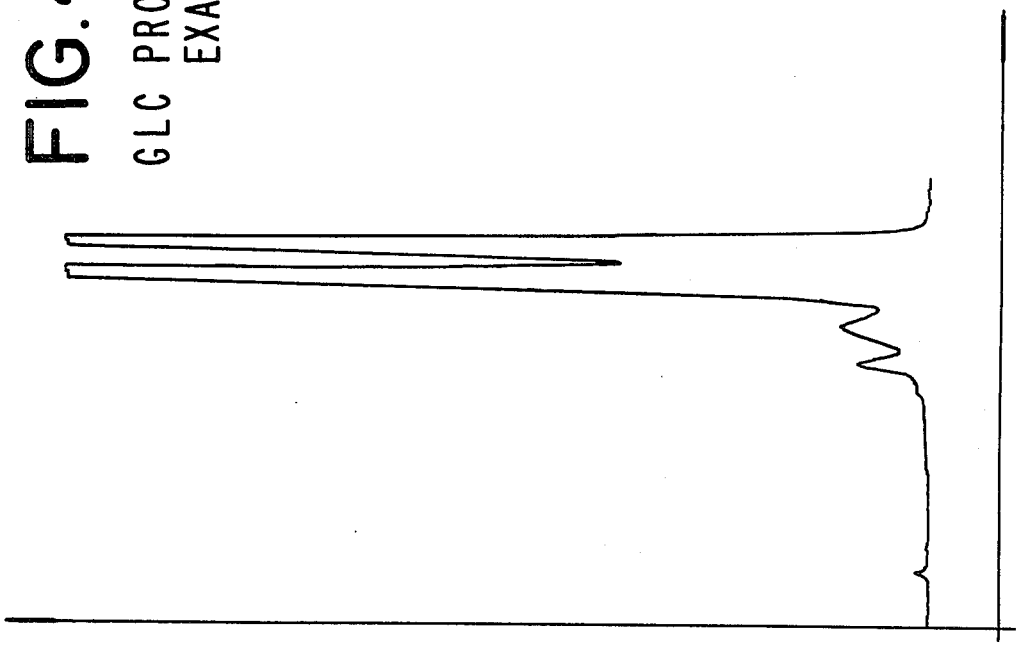

FIG. 4 represents the GLC profile for the reaction product of Example II containing primarily the compound having the structure:

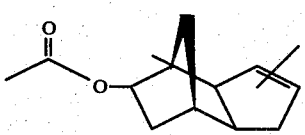

FIG. 5 represents the NMR spectrum for the compound having the structure:

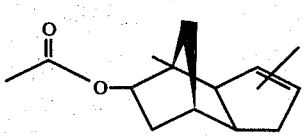

produced according to Example II.

FIG. 6 represents the infrared spectrum for the compound having the structure:

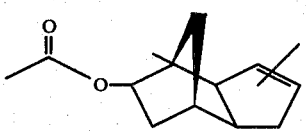

produced according to Example II.

Figure 7:
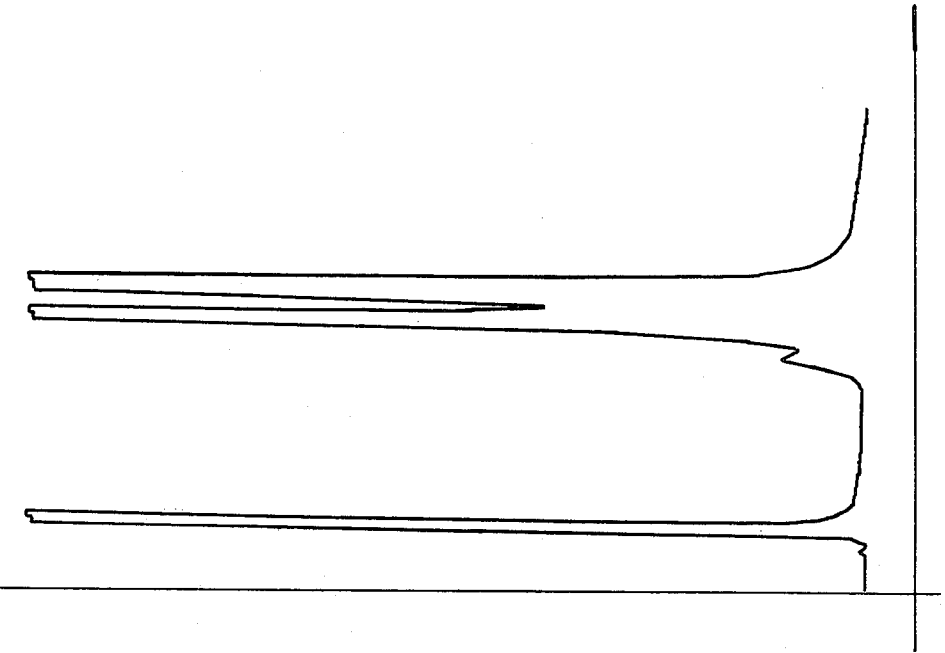

FIG. 7 represents the GLC profile for the compounds produced according to Example III having the structures:

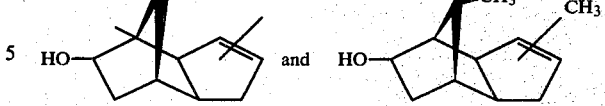

Figure 8:
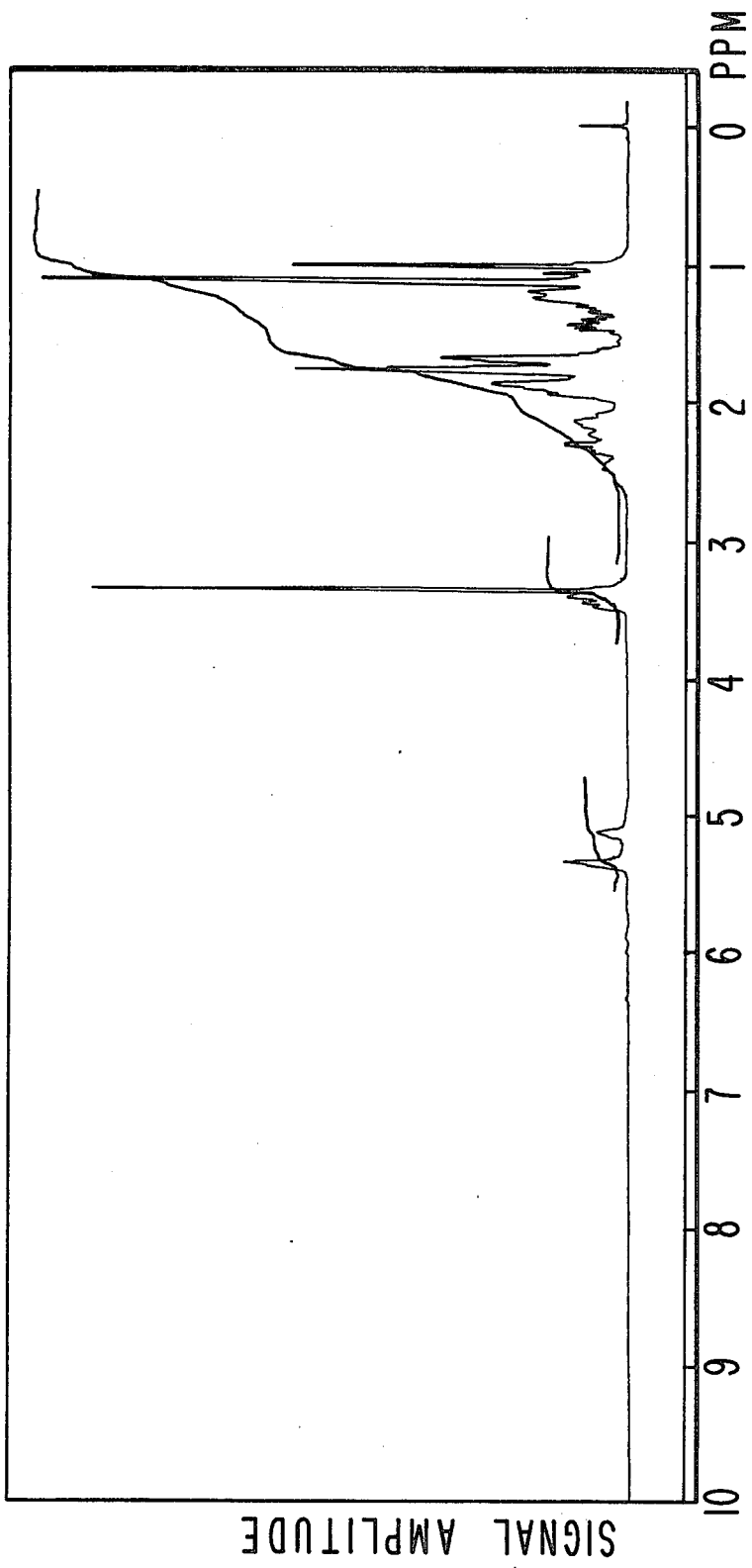

FIG. 8 represents the NMR spectrum for the compounds having the structures:

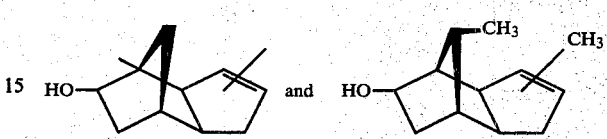

produced according to Example III.

Figure 9:
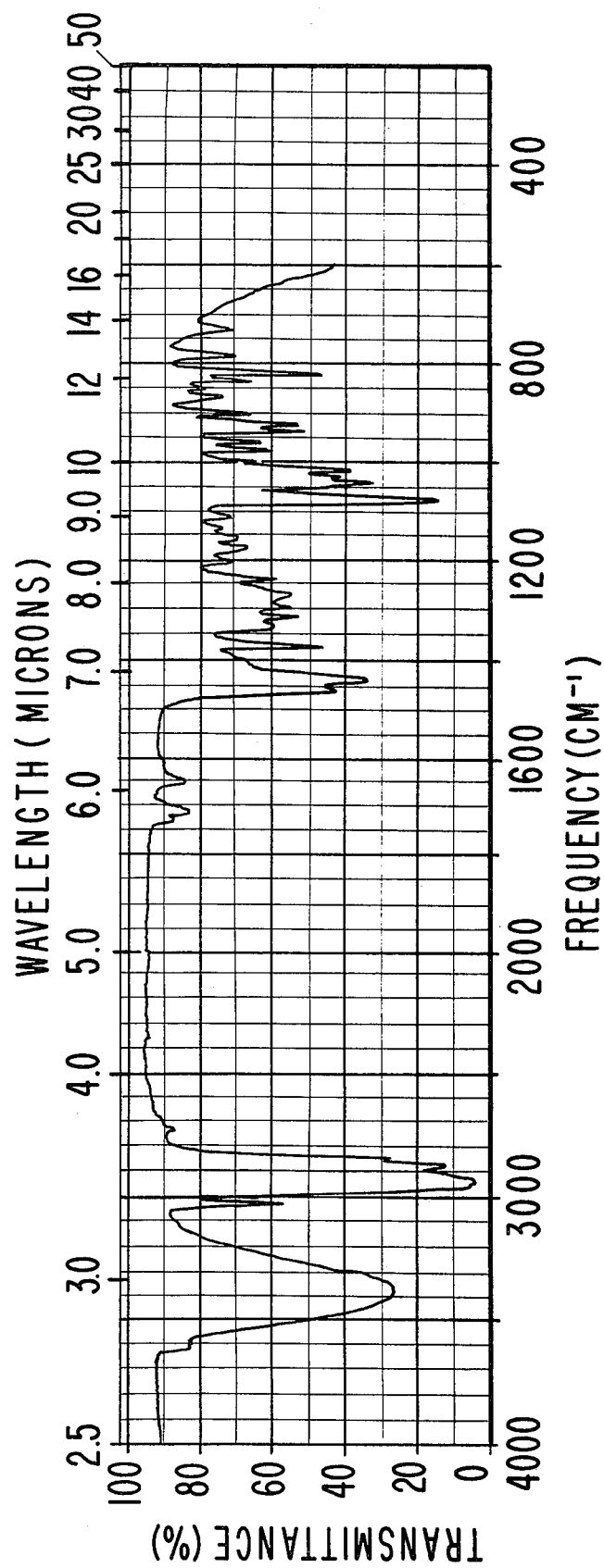

FIG. 9 represents the infrared spectrum for the compounds having the structures:

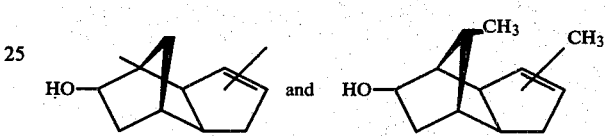

produced according to Example III.

Figure 10:
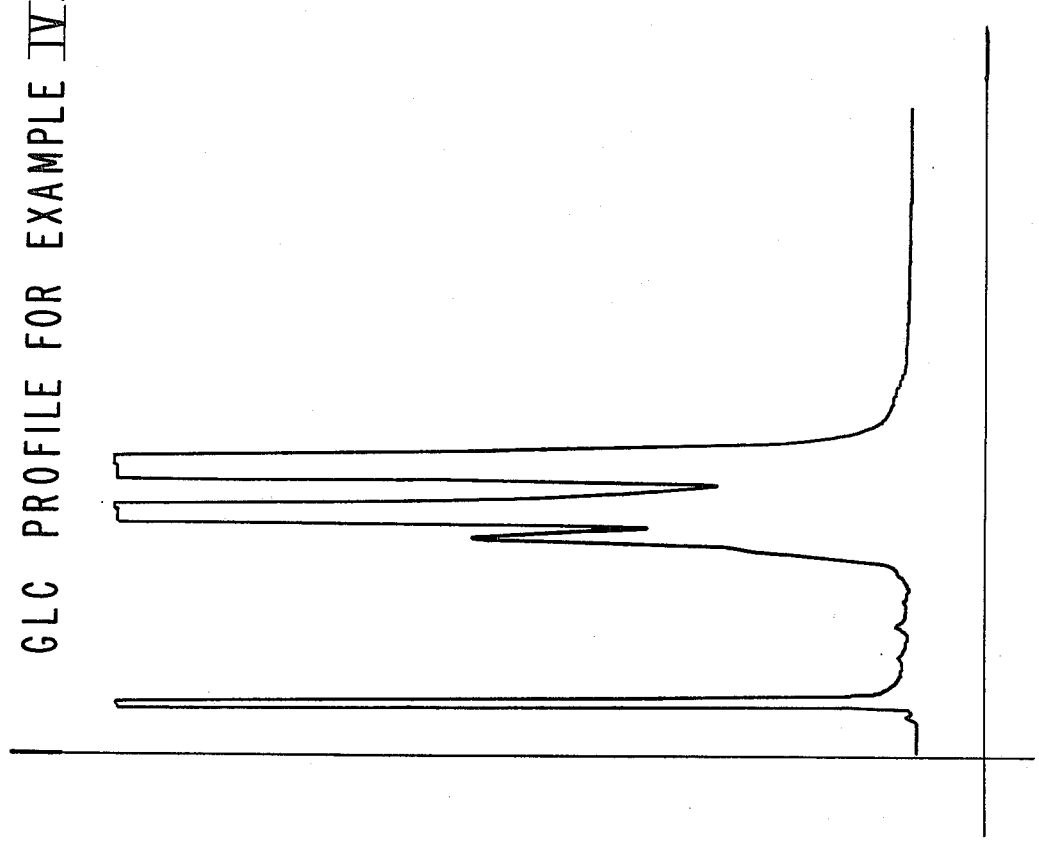

FIG. 10 represents the GLC profile for the compound having the structure:

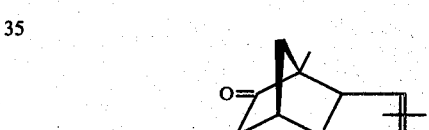

produced according to Example VI.

FIG. 11 represents the NMR spectrum for the compound having the structure:

produced according to Example VI.

FIG. 12 represents the infrared spectrum for the compound having the structure:

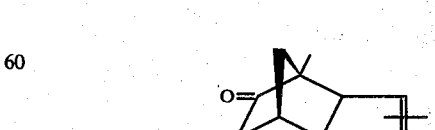

produced according to Example VI.

FIG. 13 represents the GLC profile for the compound primarily having the structure:

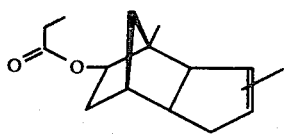

produced according to Example VII.

Figure 14:
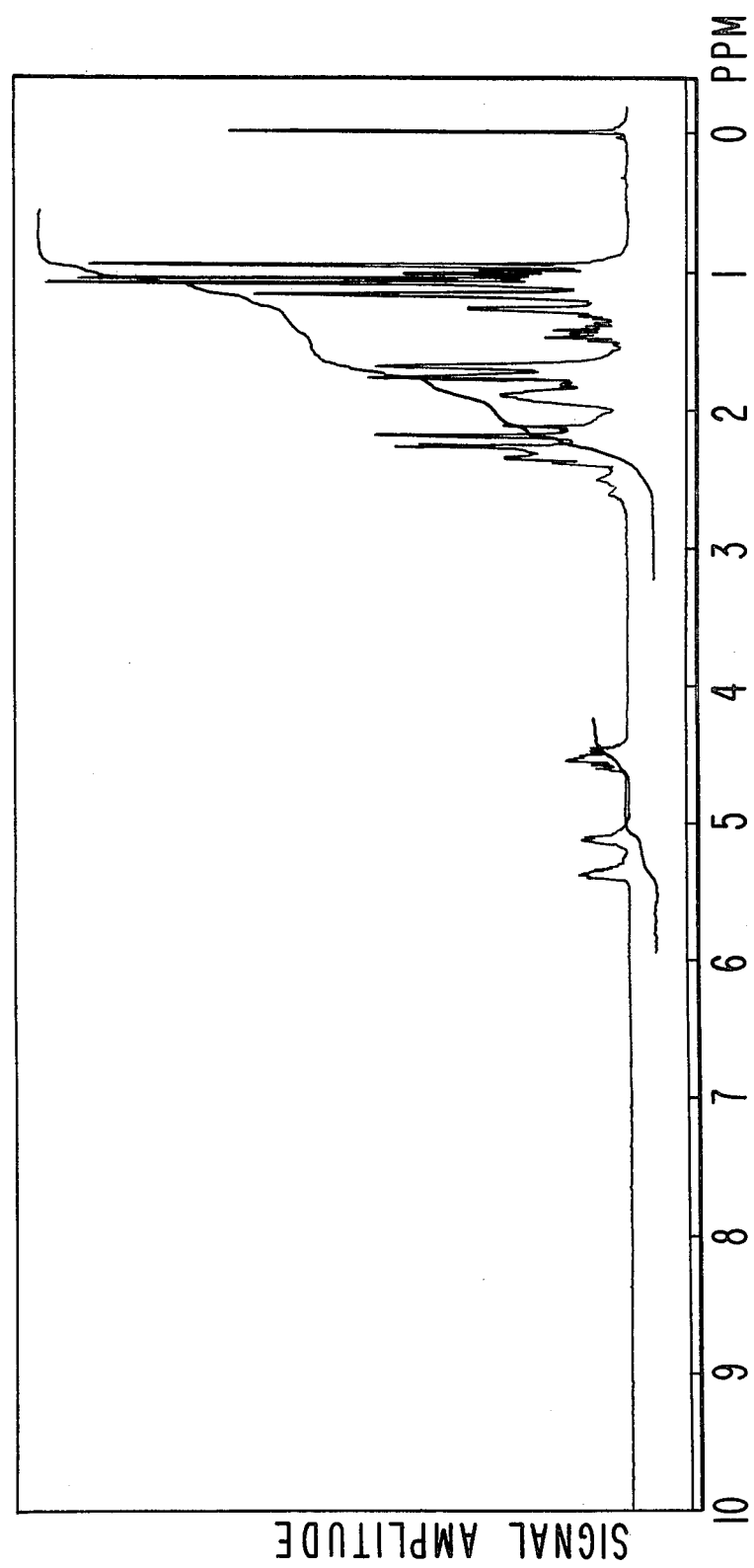

FIG. 14 represents the NMR spectrum for the compound having the structure:

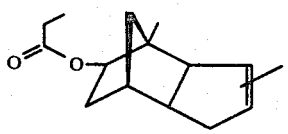

produced according to Example VII.

Figure 15:
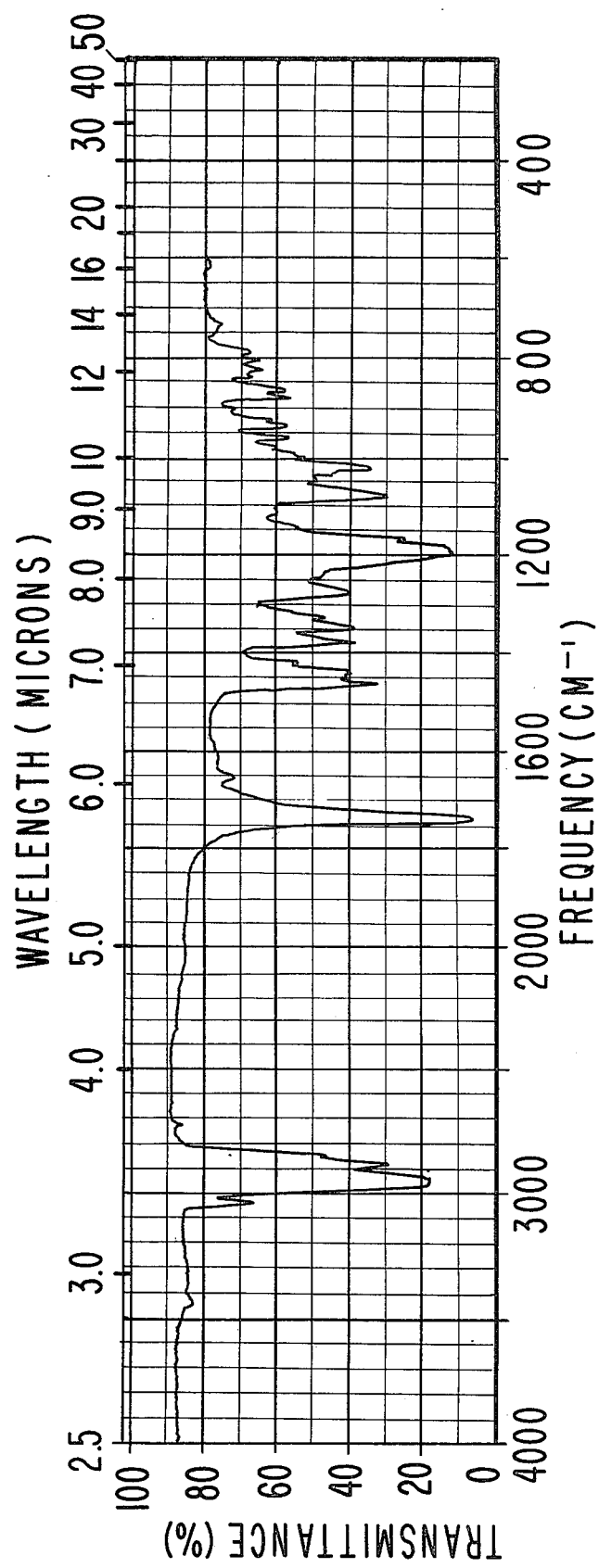

FIG. 15 represents the infrared spectrum for the compound having the structure:

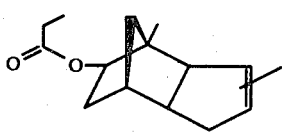

produced according to Example VII.

FIG. 16 represents the GLC profile for reaction product of Example VIII containing, primarily, the compound having the structure:

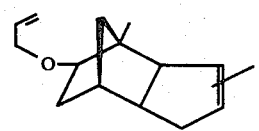

Figure 17:
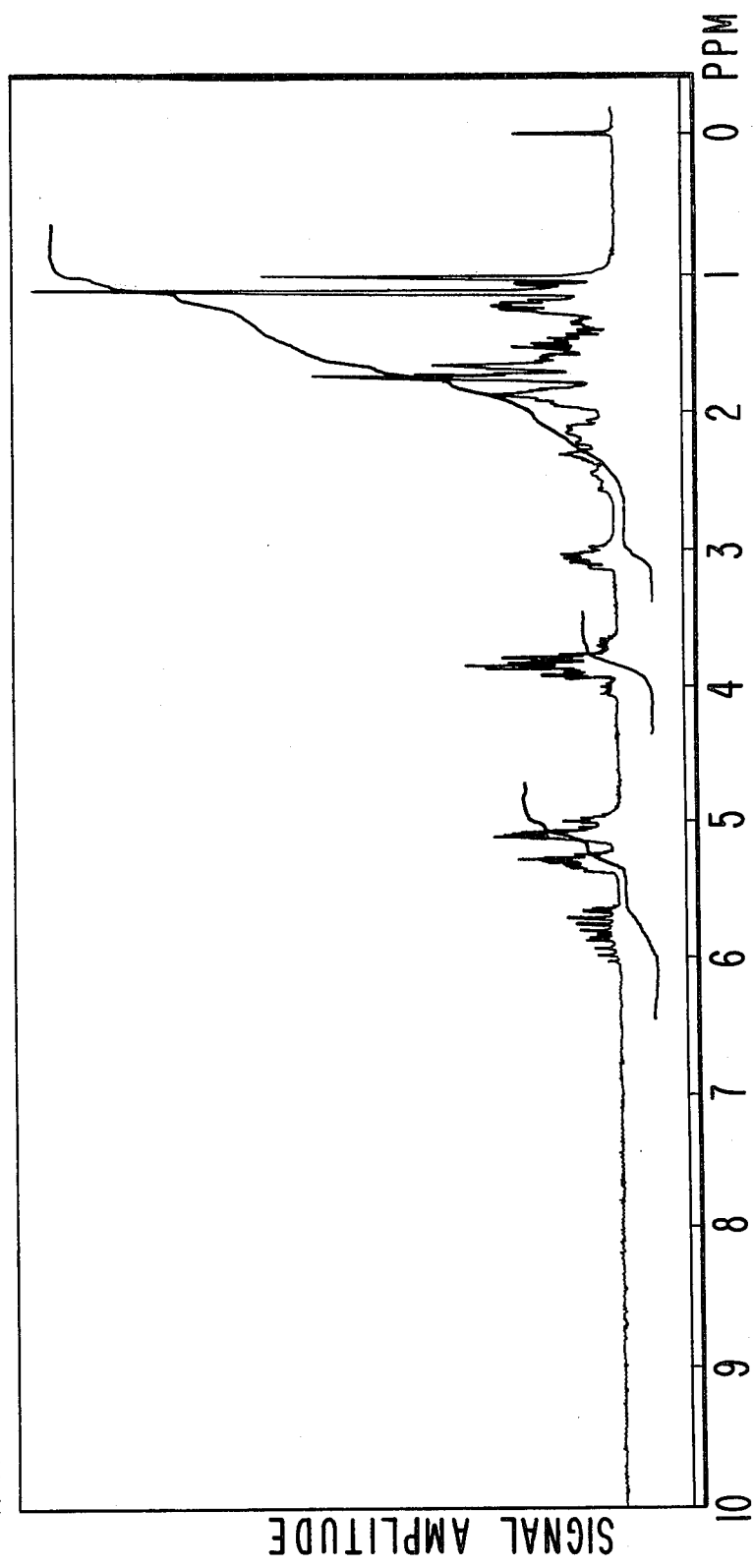

FIG. 17 represents the NMR spectrum for the reaction product of Example VIII containing primarily the compound having the structure:

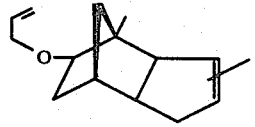

FIG. 18 represents the infrared spectrum for the reaction product of Example VIII containing, primarily, the compound having the structure:

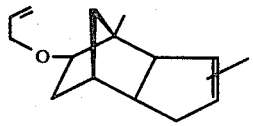

Figure 19:
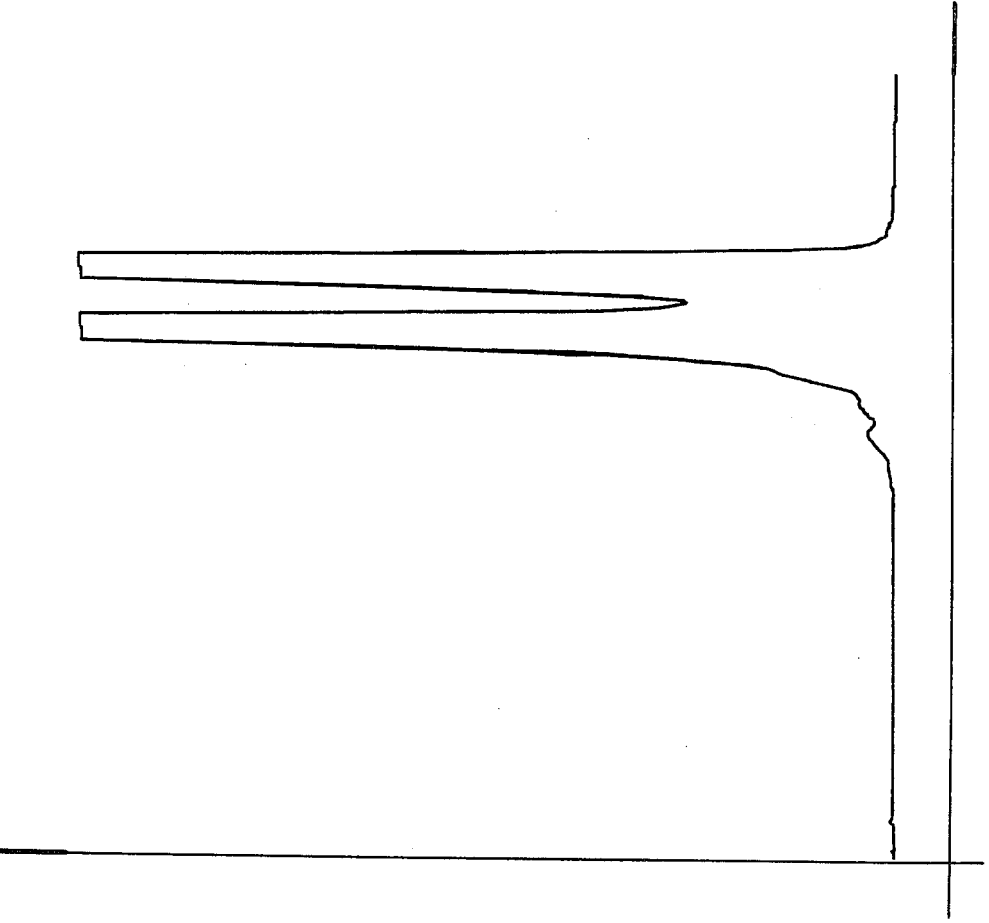

FIG. 19 represents the GLC profile for the reaction product produced according to Example IX containing, primarily, the compound having the structure:

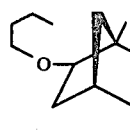

Figure 20:
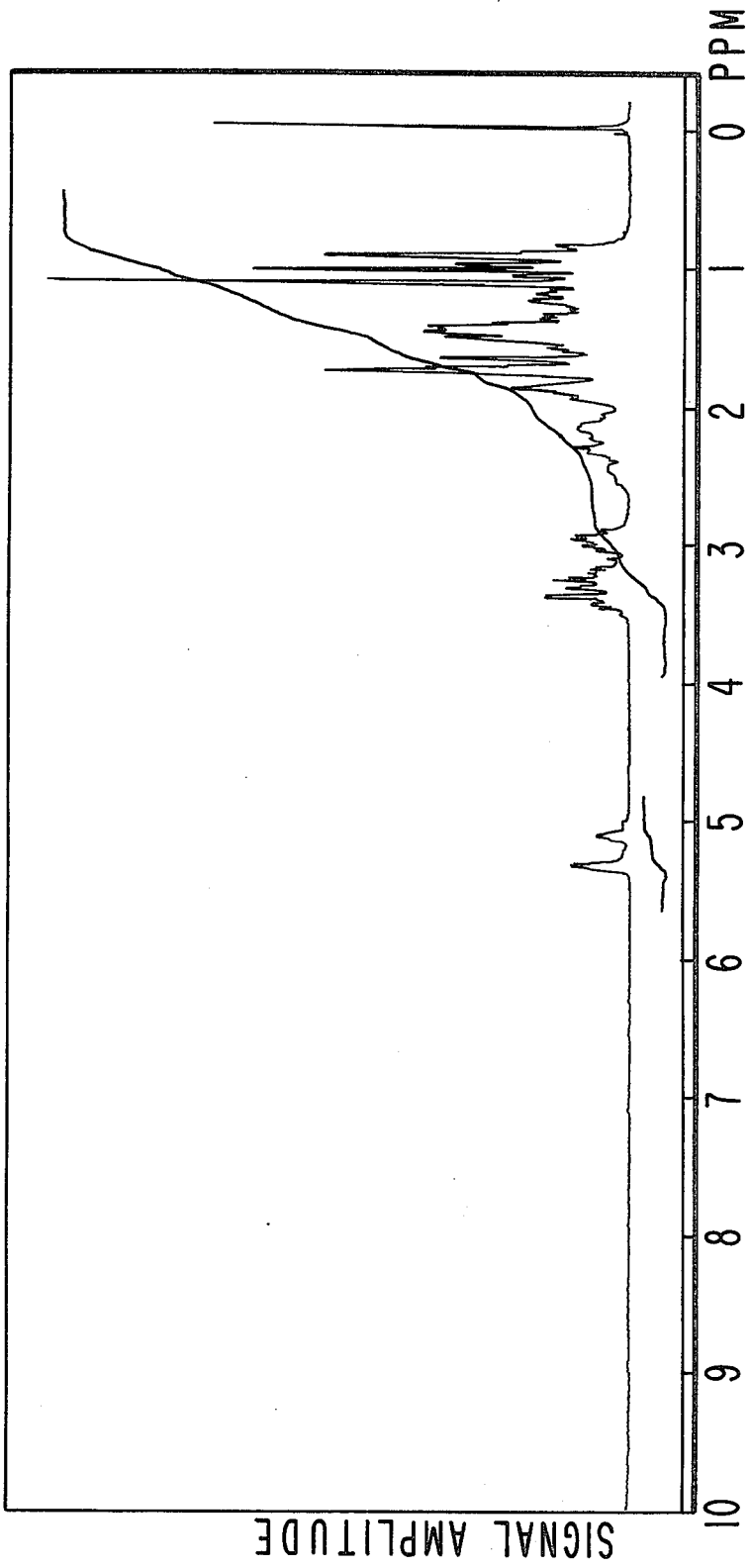

FIG. 20 represents the NMR spectrum for the reaction product of Example IX containing, primarily, the compound having the structure:

FIG. 21 represents the infrared spectrum for the reaction product of Example IX containing, primarily the compound having the structure:

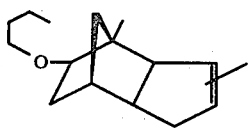

Figure 22:
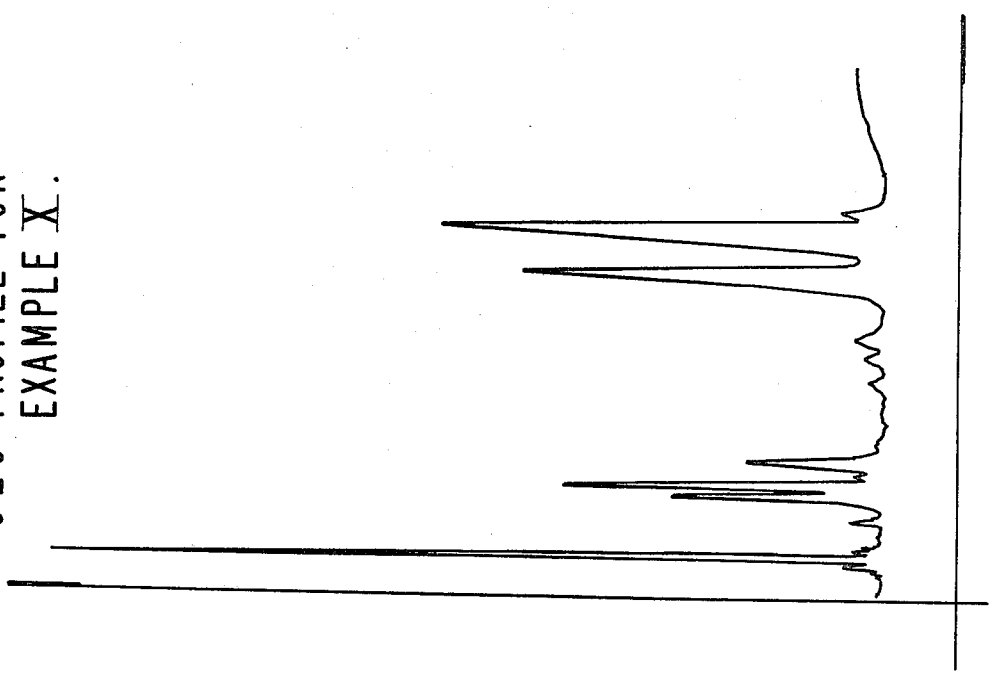

FIG. 22 represents the GLC profile for the reaction product of Example X containing, primarily, the compound having the structure:

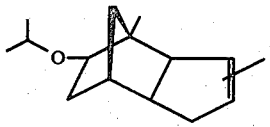

Figure 23:
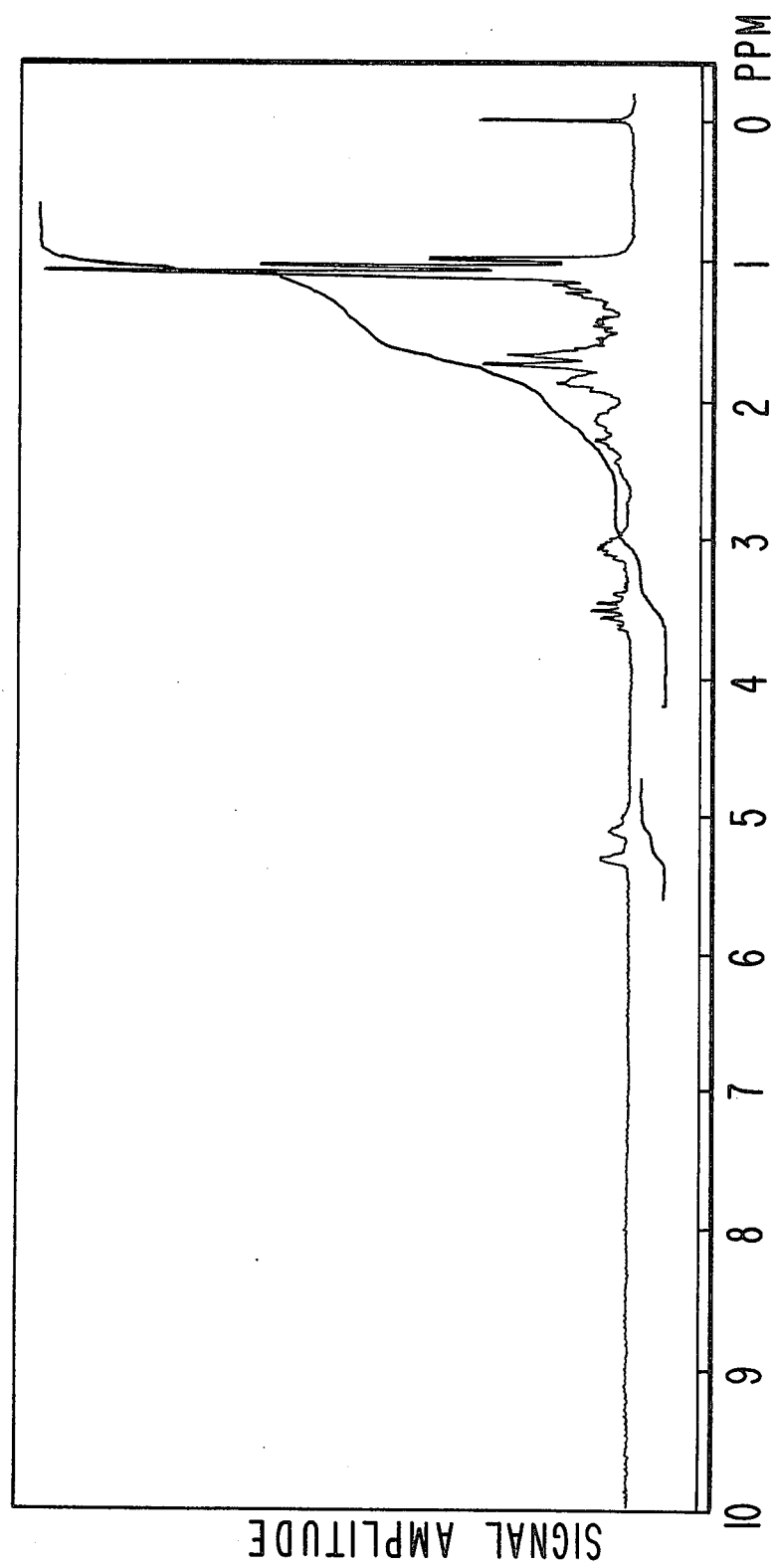

FIG. 23 represents the NMR spectrum for the reaction product of Example X containing, primarily, the compound having the structure:

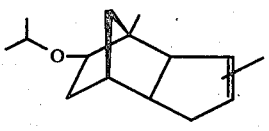

FIG. 24 represents the infrared spectrum for the reaction product of Example X containing, primarily, the compound having the structure:

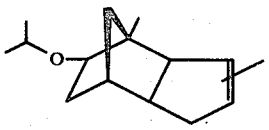

Figure 25:
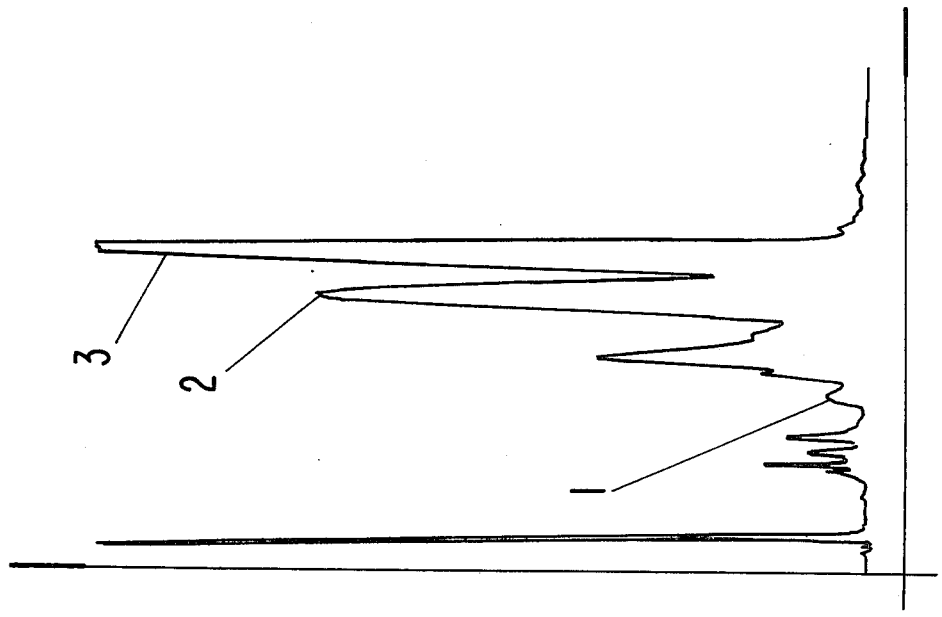

FIG. 25 represents the GLC profile for the reaction product of Example IV containing, primarily, the compounds having the structures:

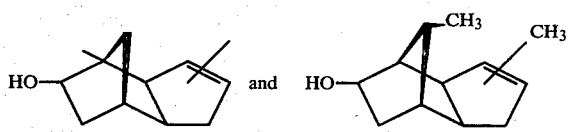

Figure 26:
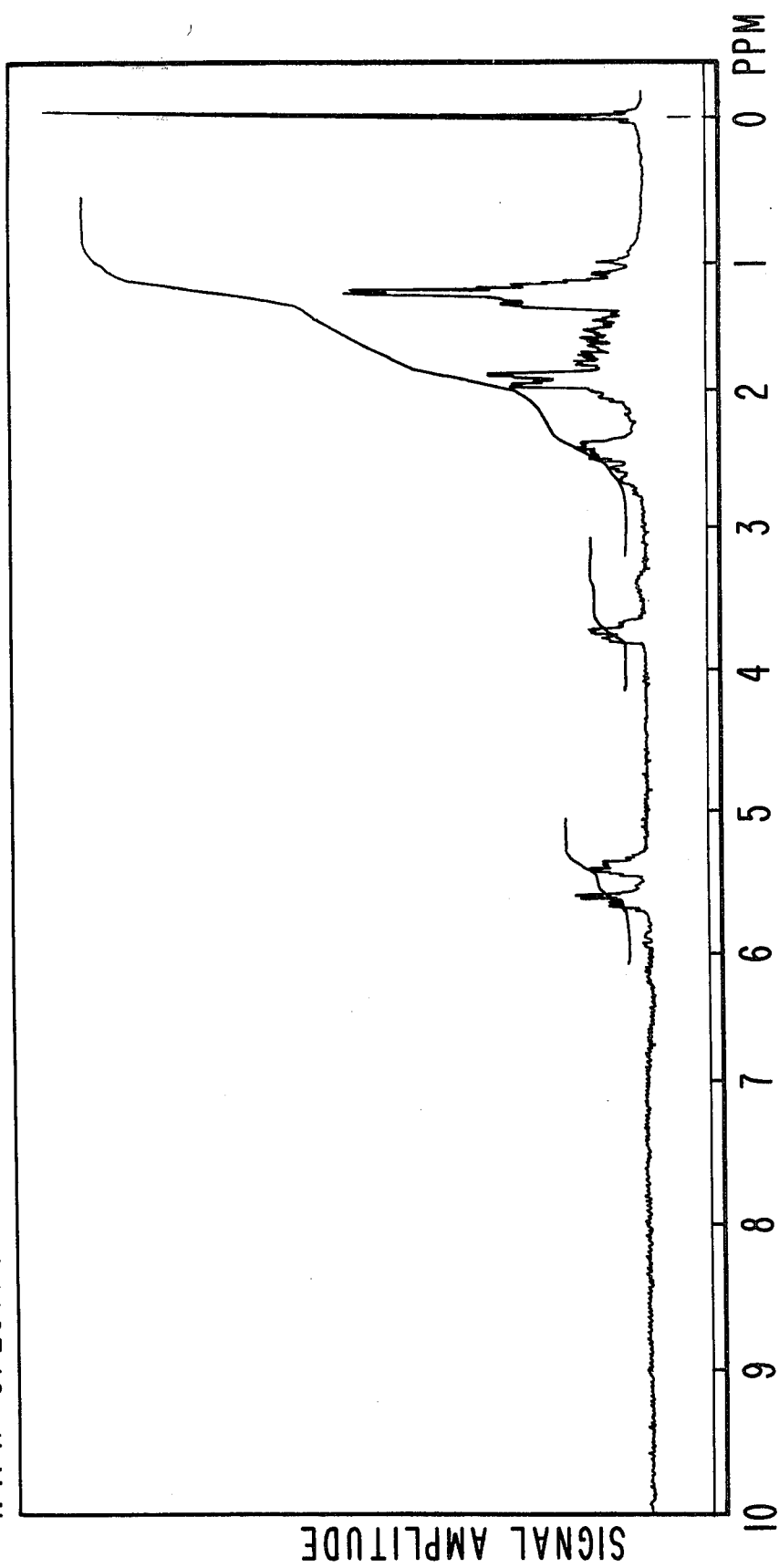

FIG. 26 represents the NMR spectrum for the compound produced according to Example IV having the structure:

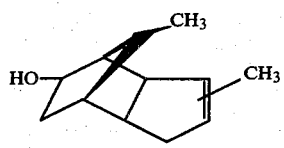

Figure 27:
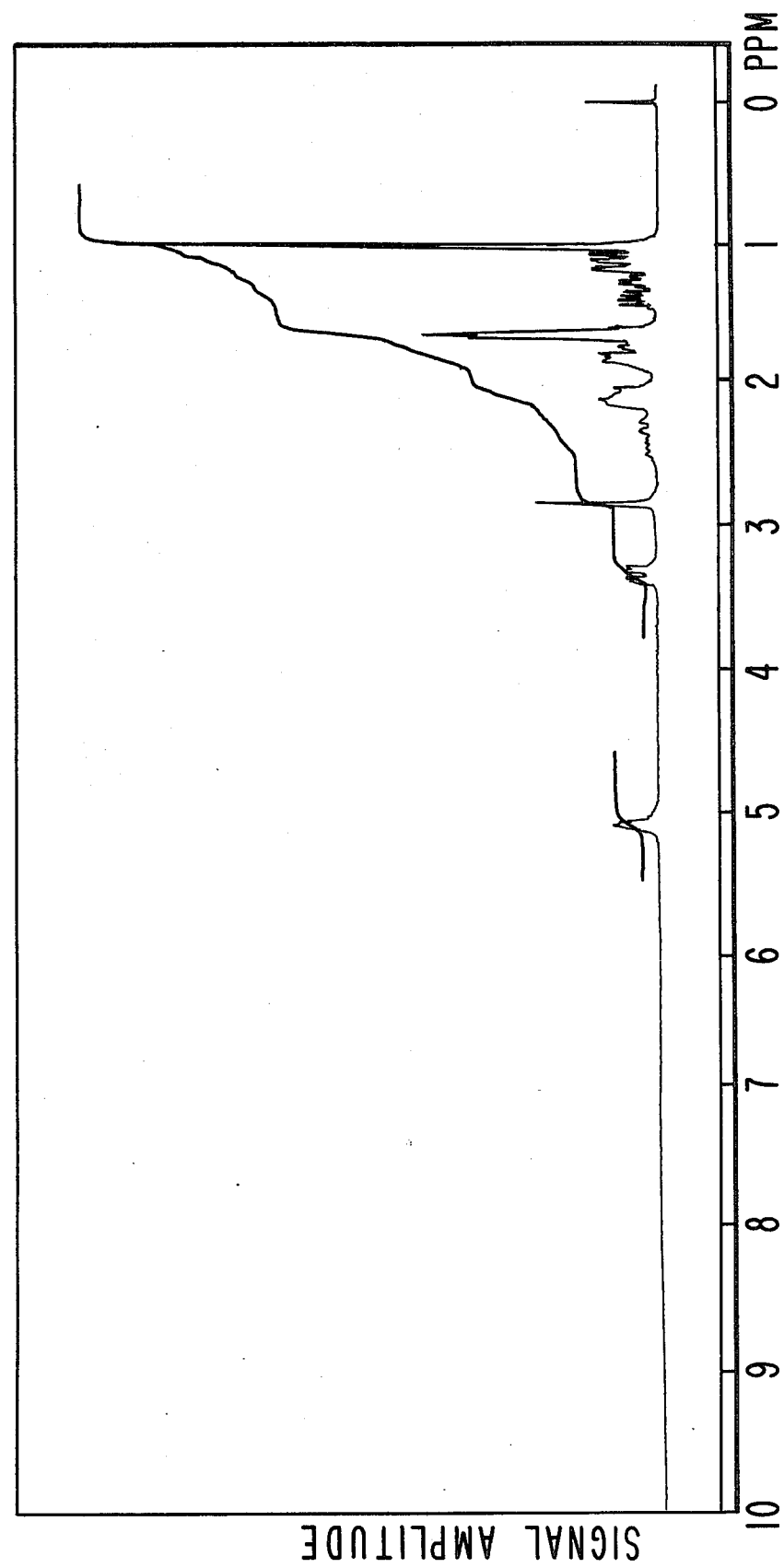

FIG. 27 represents the NMR spectrum for the compound produced according to Example IV having the structure:

Figure 28:
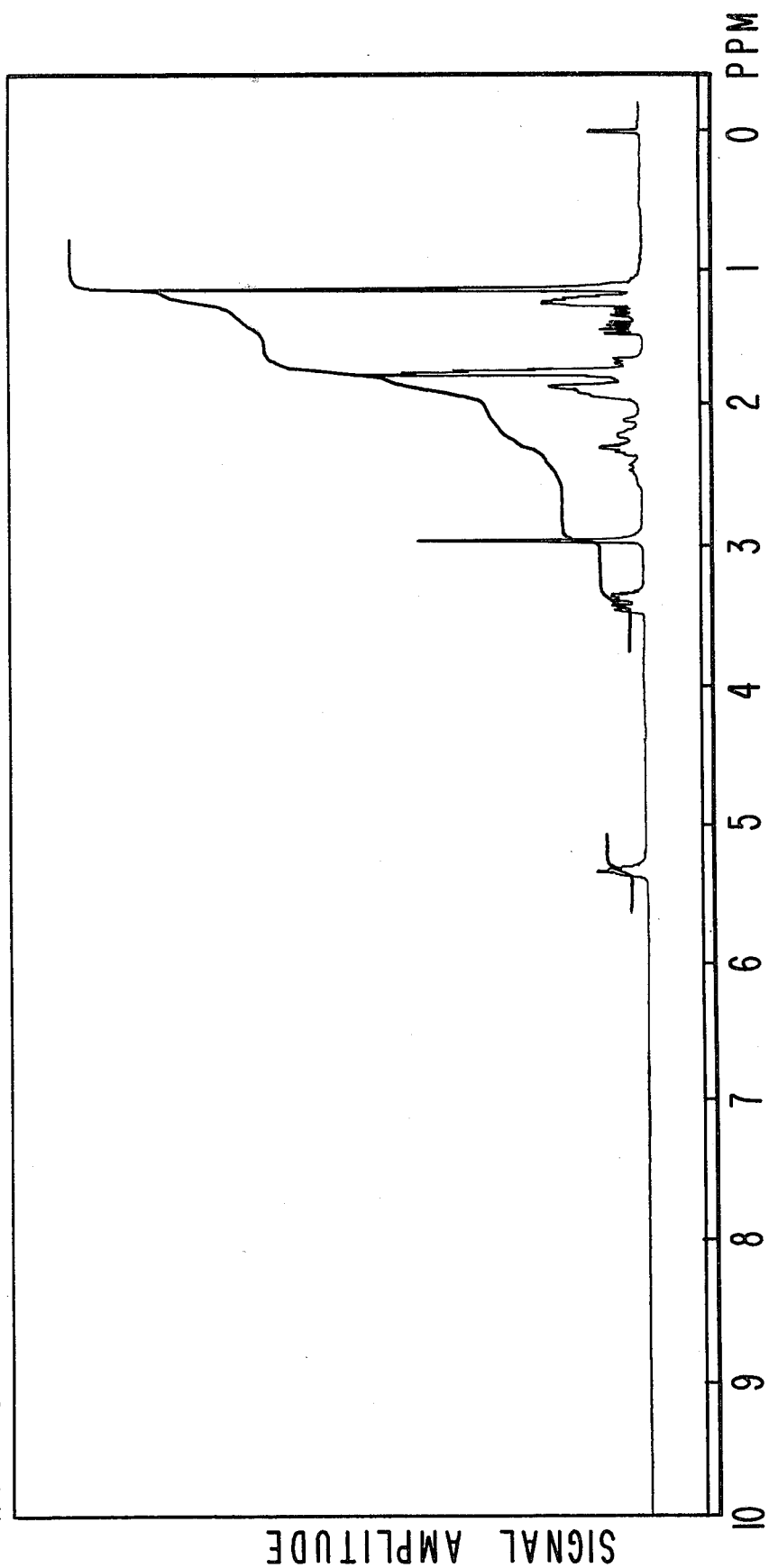

FIG. 28 represents the NMR spectrum for the compound having the structure:

produced according to Example IV.

Figure 29:
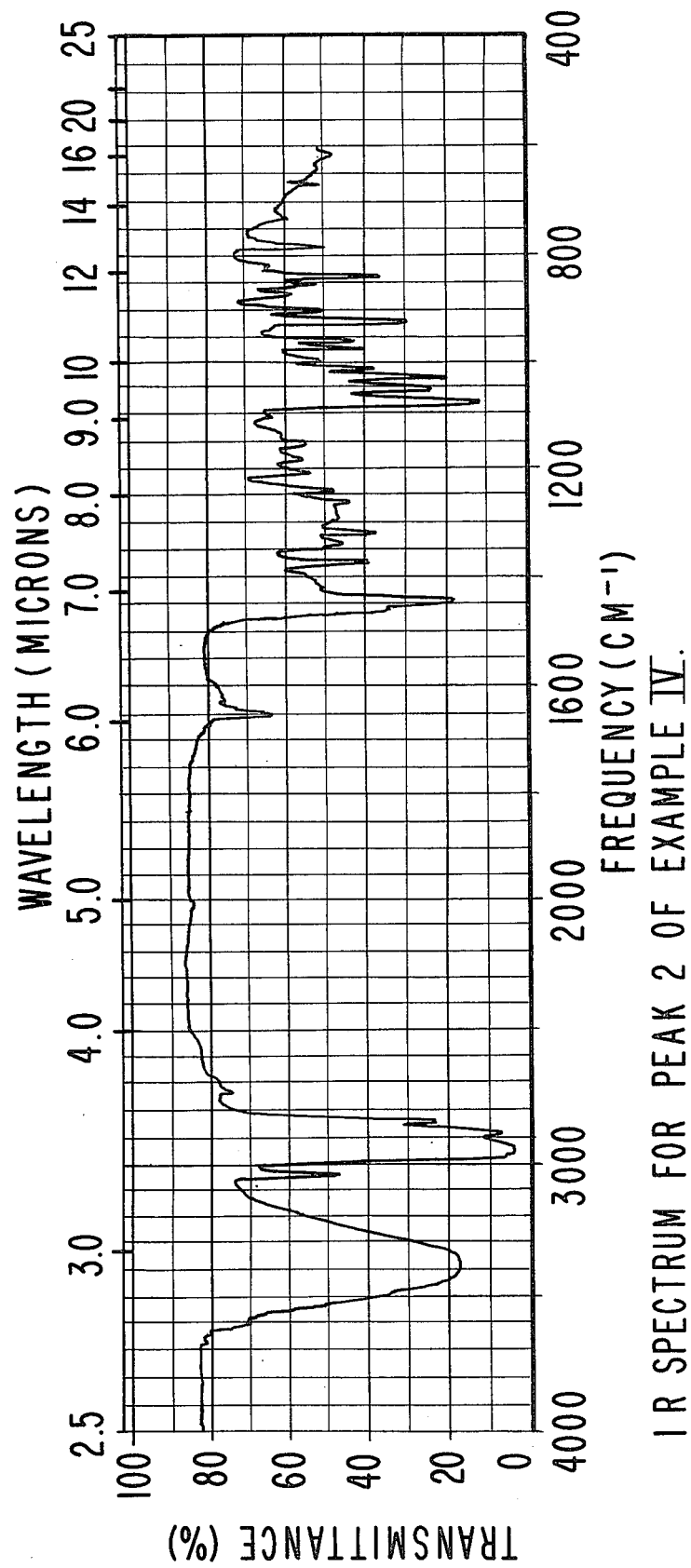

FIG. 29 represents the infrared spectrum for the compound having the structure:

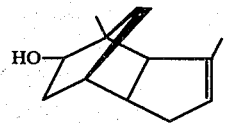

produced according to Example IV.

Figure 30:
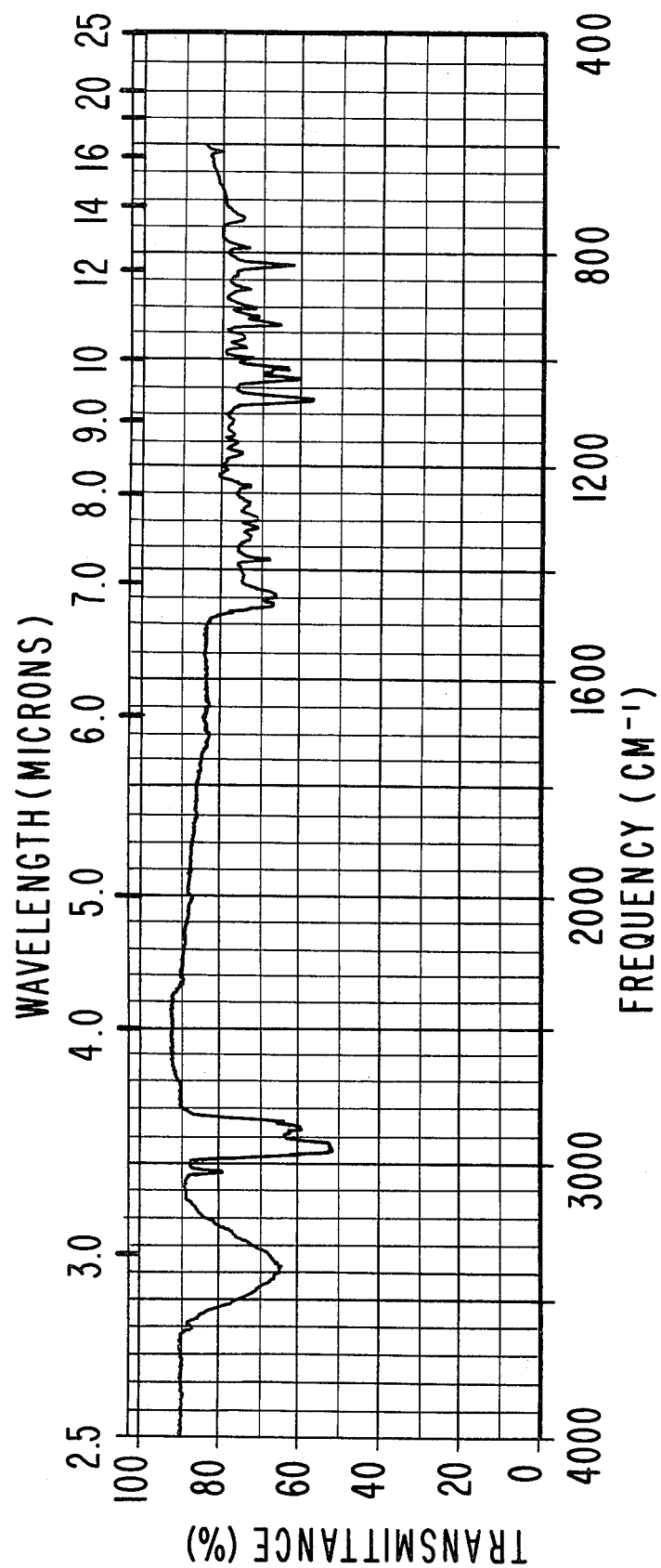

FIG. 30 represents the infrared spectrum for the compound having the structure:

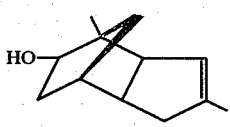

produced according to Example IV.

Figure 31:
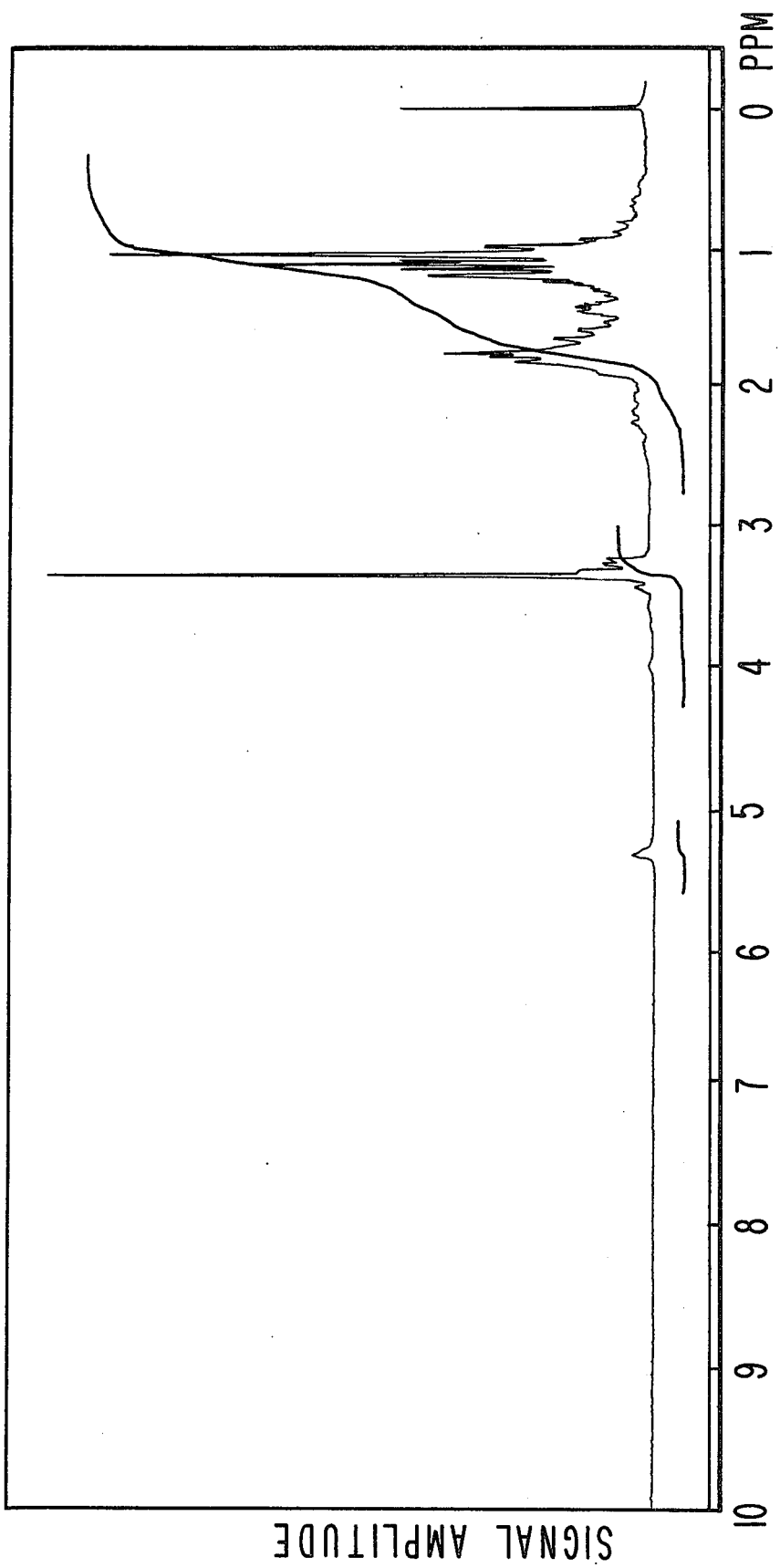

FIG. 31 represents the NMR spectrum for the compound produced according to Example XI having the structures:

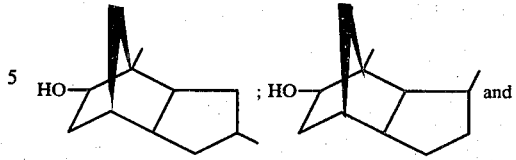

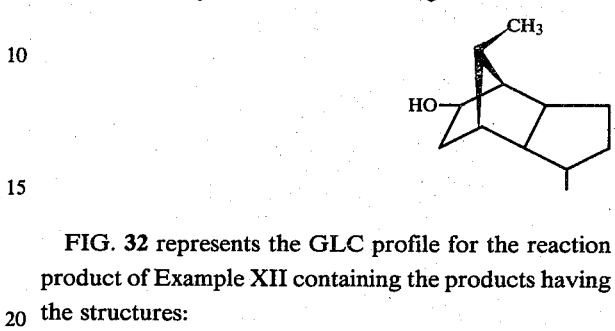

Figure 32:
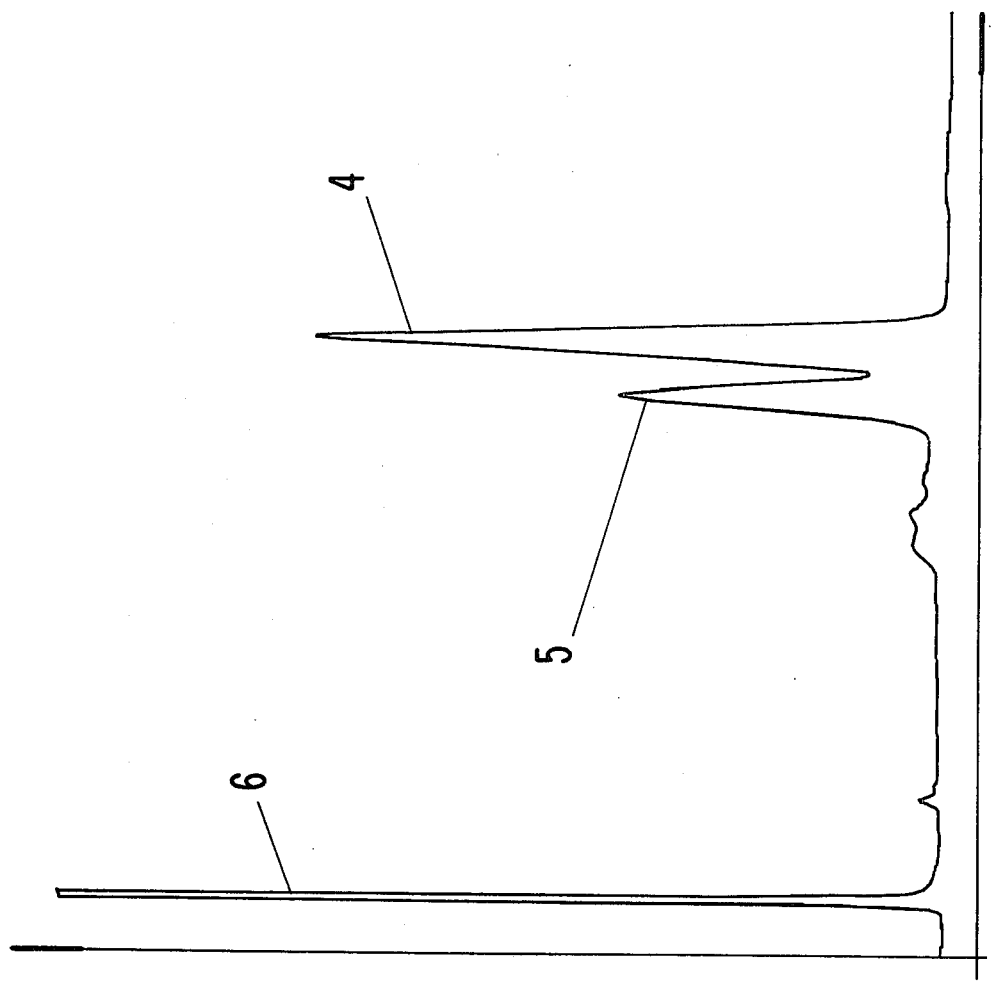

FIG. 32 represents the GLC profile for the reaction product of Example XII containing the products having the structures:

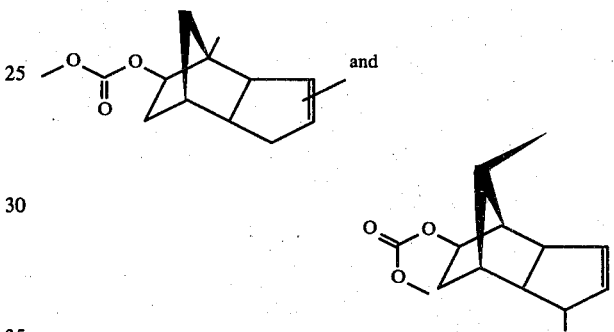

FIG. 33 represents the NMR spectrum for fraction 5 of the distillate of the reaction product of Example XII containing the compounds having the structures:

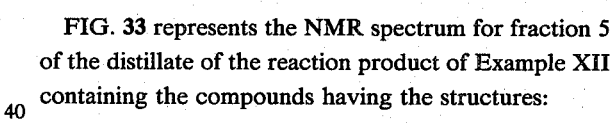

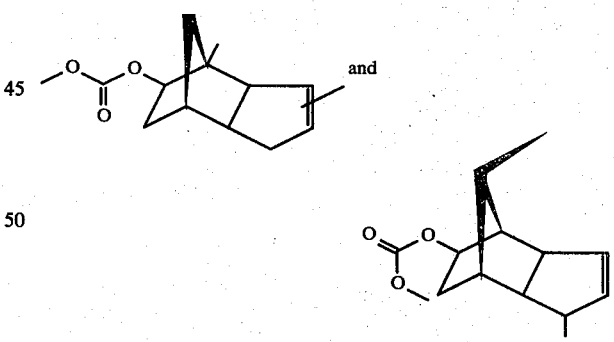

FIG. 34 represents the infrared spectrum for fraction 5 of the distillation product of the reaction product of Example XII containing the compounds having the structures:

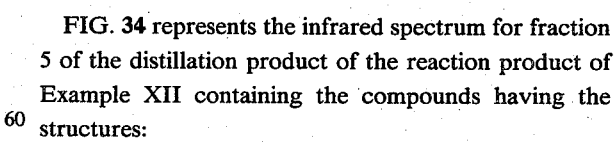

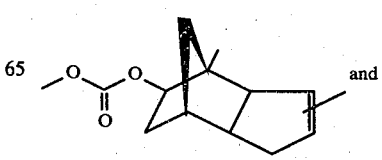

-continued

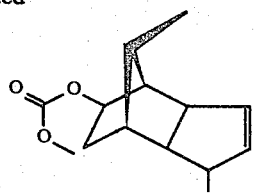

Figure 35:
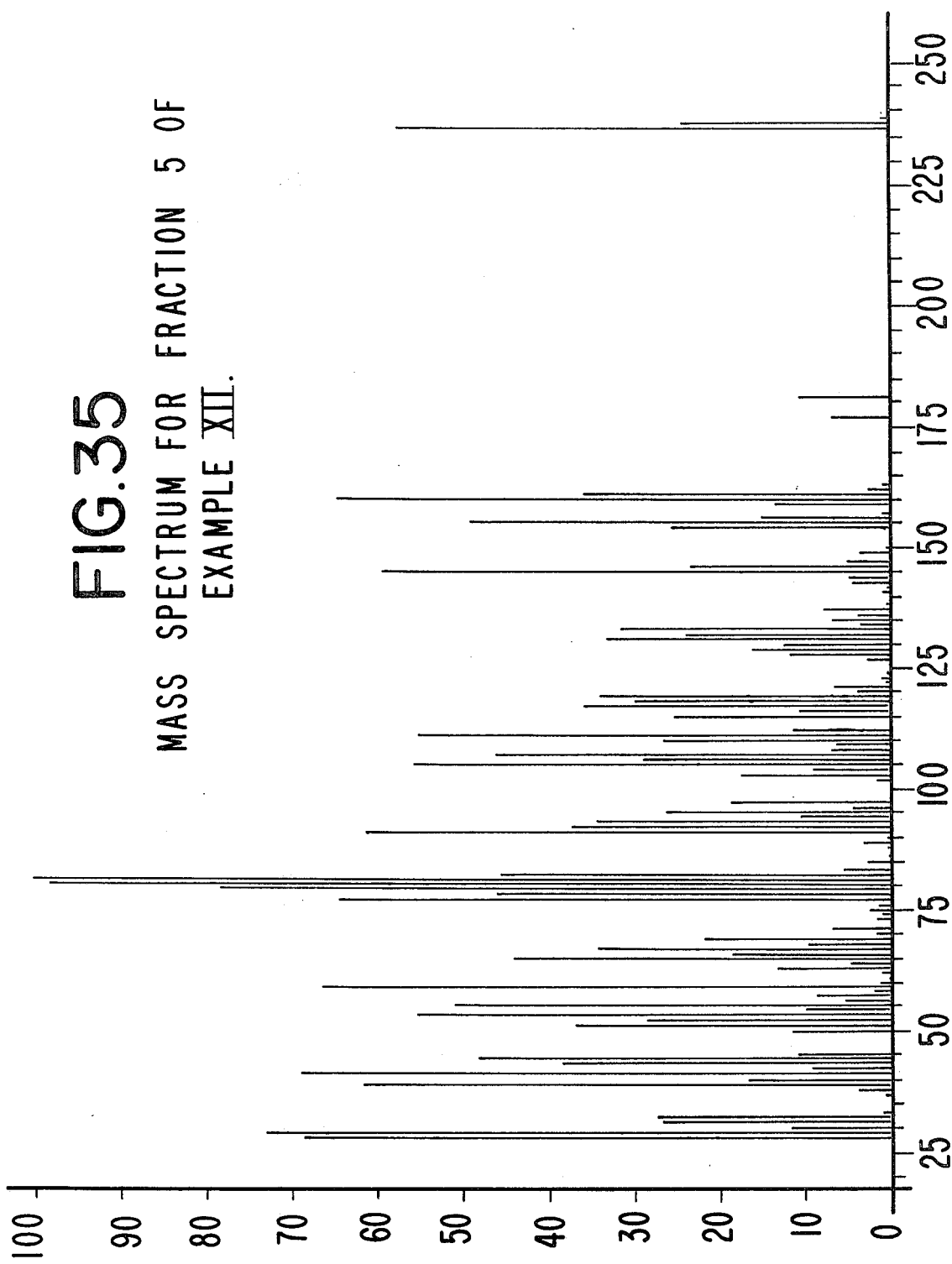

FIG. 35 represents the mass spectrum for fraction 5 of the distillation product of the reaction product of Example XII containing the compounds having the structures:

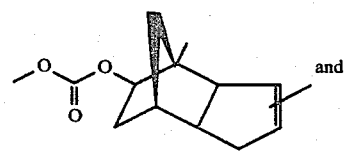

and

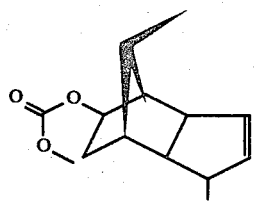

DETAILED DESCRIPTION OF THE DRAWING

FIG. 25 is the GLC (gas liquid chromatography) profile (conditions: ⅛"×10' column coated with 10% SE-30). The peak indicated with the numeral 1 signifies the compound having the structure:

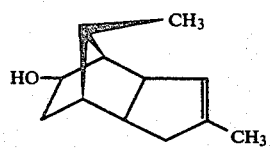

The peak indicated by the numeral 2 signifies the compound having the structure:

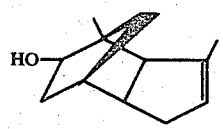

The peak signified by the numeral 3 signifies the compound having the structure:

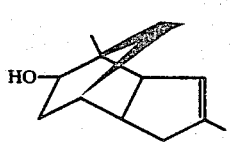

The compound having the structure:

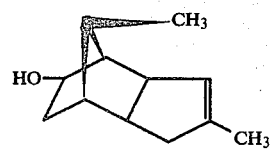

has a strong patchouli aroma.

In FIG. 5 which represents the GLC profile for the reaction product of Example XII, reference "4" and reference "5" represent products (ratio: 20.51 for peak "4":18.60 for peak "5") and peak "6" repesents the solvent peak for the GLC run. The GLC profile was carried out using an SE-30 column. Peak "4" and peak "5" contain the structures:

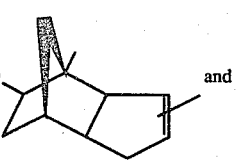

and

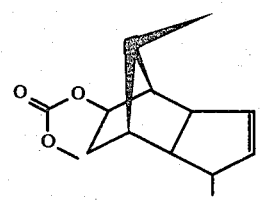

and the structure:

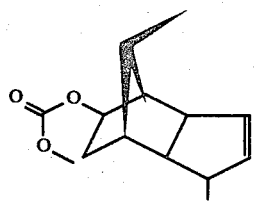

is in itself a mixture of positional isomers and each of the structures:

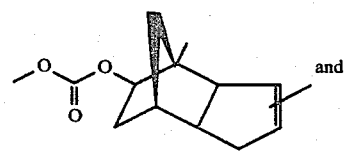

and

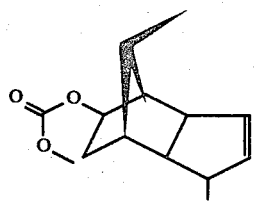

represent mixtures of "cis" and "trans" isomers or "endo" and "exo" isomers. The GLC column is a ⅛"×10' SE-30 packed column programmed at 200° C.

THE INVENTION

It has now been determined that certain substituted tricyclodecane derivatives are capable of imparting a variety of flavors and fragrances to various consumable materials. Briefly, our invention contemplates augmenting or enhancing the flavors and/or fragrances of such consumable materials by adding thereto a small but effective amount of at least one such substituted tricyclodecane derivatives defined according to the generic structure:

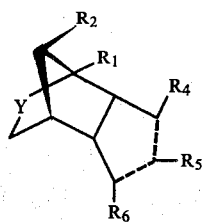

wherein Y is a moiety having a structure selected from the group consisting of:

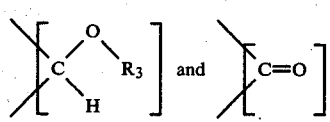

wherein one of the dashed lines represents a carbon-carbon single bond and the other of the dashed lines represents a carbon-carbon double bond; wherein $R_1$ and $R_2$ represent hydrogen or methyl with the proviso that one of $R_1$ and $R_2$ is hydrogen and the other of $R_1$ and $R_2$ is methyl; wherein $R_3$ is hydrogen, $C_1$–$C_3$ acyl, $C_3$ or $C_4$ alkyl or $C_3$ or $C_4$ alkenyl; wherein $R_4$, $R_5$ and $R_6$ represent hydrogen or methyl with the additional proviso that one of $R_4$, $R_5$ and $R_6$ is methyl and the other two of $R_4$, $R_5$ and $R_6$ is hydrogen and flavoring (e.g., for foodstuffs, chewing gum, chewing tobaccos, medicinal products and smoking tobacco) and fragrance compositions (e.g., perfume compositions and compositions for augmenting or enhancing the aroma of perfumed articles, such as solid or liquid anionic, cationoc, nonionic, zwitterionic detergents or fabric softeners or cosmetic powders) containing such substituted tricyclodecane derivatives. The invention also contemplates novel processes for producing such compounds.

The substituted tricyclodecane derivatives produced according to the processes of our invention which are used in practicing that part of our invention concerning flavoring and fragrance compositions are actually racemic mixtures rather than individual stereoisomers, such as is the case concerning isomers of patchouli alcohol isomers which are obtained from patchouli oil.

The substituted tricyclodecane derivatives of our invention insofar as their fragrance profiles are concerned have green, floral, woody, patchouli-like musty-camphoraceous, rosey, woody, anisic, ionone-like, fruity (banana), spicey (cinnamic), bitter sweet, milky, petitgrain-like, lavender, bergamot-like, fatty and minty aromas with spicey, green, basil, raspberry-like, sweatey, pith-like, pumpkin-like and creamy undertones and fruity/berry intense aromas on dry out.

Insofar as their flavor uses are concerned, (e.g., foodstuffs, chewing gums, medicinal products and chewing tobaccos), the substituted tricyclodecane derivatives of our invention have sweet, cocoa butter-like, herbaceous, green, floral, and anise aroma profiles and sweet, cocoa butter-like, herbaceous, green, floral and anise flavor profiles.

Insofar as smoking tobacco flavors are concerned, the substituted tricyclodecane derivatives of our invention have cocoa-like, sweet, floral and green aroma profiles prior to smoking and sweet, floral and aromatic aroma and taste nuances on smoking in both the main stream and the side stream.

The following table sets forth the structure and organoleptic property profiles for specific compounds according to the Examples listed herein and located infra:

TABLE I

| Structure | Fragrance Profile | Food Flavor Profile | Tobacco Flavor Profile |
|---|---|---|---|
| (produced according to Example I.) | A strong maple aroma with pumpkin-like and slightly spicy undertones. | | A sweet, fruity, citrusy aroma and taste prior to and on smoking in both the main stream and the side stream. |
| (produced according to Example II.) | A fruity, anisic aroma with a raspberry undertone; on dryout, fruity and berry-like. | A sweet, cocoa butter-like, herbaceous and green aroma and flavor profile at 0.2 ppm and at 1 ppm, herbaceous and green notes dominate over the cocoa-butter character. | A sweet, woody, spicy, herbaceous aroma and taste both prior to and on smoking in the main stream and side stream. |

TABLE I-continued

| Structure | Fragrance Profile | Food Flavor Profile | Tobacco Flavor Profile |
|---|---|---|---|
|  and 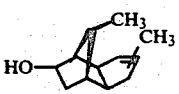 produced according to Example III, IV and V. | A woody, resinous, camphoraceous patchouli-like aroma reminiscent of patchouli alcohol; with oakmoss undertones then green, and woody and floral and rosey topnotes. | A floral, fruity, citronellol-like and patchouli aroma characteristic with a floral, fruity, citronellol-like patchouli and fresh walnut flavor characteristic at 2 ppm. | A sweet, herbaceous, spicy, hay-clover-like and woody aroma and taste profile both prior to and on smoking in the main stream and the side stream. |
|  and  produced according to Example VI. | A fatty, slightly minty and camphoraceous aroma with pith-like and pumpkin nuances as well as woody and piney undertones. | A floral, herbaceous, citrus-like, fruity and patchouli-like aroma and taste and flavor profile at 5 ppm. | A sweet, creamy and buttery aroma and taste both prior to and on smoking in the main stream and in the side stream. |
| 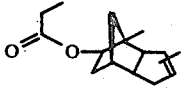 and 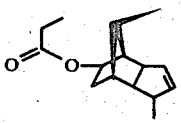 produced according to Example VII. | A green, fruity, creamy, rhubarb stem-like and banana-like aroma. | A green, fruity, pear-like, cocoa butter-like aroma and flavor profile causing it to be useful in pea flavor and cocoa butter flavor formulations at 1 ppm. | A sweet, fruity, plum-like, fatty, cucumber-like aroma and taste both prior to and on smoking in the main stream and in the side stream. |
|  and 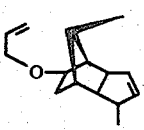 produced according to Example VIII. | A strong, herbaceous aroma with an oily and spicey, green, basil undertone. | A sweet, floral, anise-like, green and herbaceous aroma and flavor profile at 1 ppm. | A cocoa-like, sweet, floral and green aroma prior to smoking and a sweet, floral and green aroma on smoking in the main stream and in the side stream. |
|  and  produced according to Example IX. | A low keyed fruity (banana), spicey (cinnamic), green aroma with sweaty and creamy undertones. | A green, waxy, cocoa-butter-like aroma profile with a green, waxy, cocoa powder and bitter flavor profile at 2 ppm. | A sweet, floral, carnation, creamy aroma and taste prior to smoking and a green, floral aroma and taste on smoking in the main stream and in the side stream. |

TABLE I-continued

| Structure | Fragrance Profile | Food Flavor Profile | Tobacco Flavor Profile |
|---|---|---|---|
| 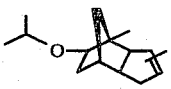 and 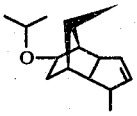 produced according to Example X. | A bitter, sweet, herbal, petitgrain-like, lavender and bergamot aroma profile with floral undertones. | A green, floral aroma characteristic with bitter flavor characteristics at 0.1 ppm. | A sweet, green, cucumber, melon, pea-like aroma and taste both prior to and on smoking in the main stream and the side stream. |
| 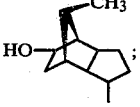 and 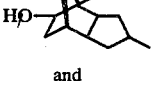 produced according to Example XI. | A minty, spicey, fruity aroma with caryophyllene-like, cedarwood and sandalwood undertones becoming borneol-woody-like on a dry-out. | A minty, cooling, camphoraceous, patchouli-like aroma and flavor profile causing it to be useful in oral hygiene flavors, mint flavors and peppermint flavors at 2 ppm. | A earthy, grapefruit peel-like, albedo, camphoraceous aroma and taste both prior to and on smoking in the main stream and in the side stream. |
| 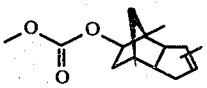 and 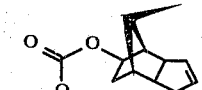 produced according to Example XII. | A fruity (apple), anisic-like aroma with dry, hay-like and berry-like undertones. | A green, waxy, cocoa-butter-like aroma and flavor character with additional bitter flavor nuances at 1 ppm. | A sweet, woody, camphoraceous, spicey aroma and taste profile both prior to and on smoking in the main stream and in the side stream. |

The substituted tricyclodecane derivatives produced according to the process of our invention which are used in practicing that part of our invention concerning flavor and fragrance compositions may be mixtures of isomers or they may be substantially pure forms of exo or endo isomers or specific stereoisomers such as the case concerning isomers of patchouli alcohol which are obtained from patchouli oil.

The substituted tricyclodecane derivatives prepared according to our invention can be obtained by reacting either mixtures or specific isomers of dimethyl cyclopentadiene and these isomers have the structures:

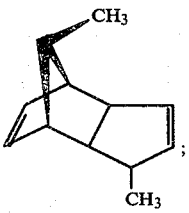

-continued

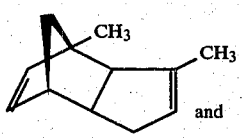 and

The compounds having the structures:

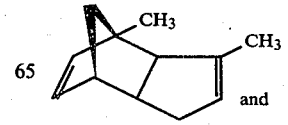 and

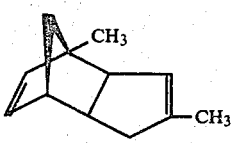

may be represented in admixture by the structural representation:

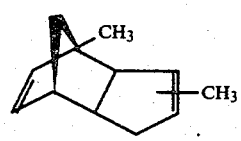

These materials may be prepared by dimerizing one or two or a mixture of all three of the methyl cyclopentadiene isomers having the structures:

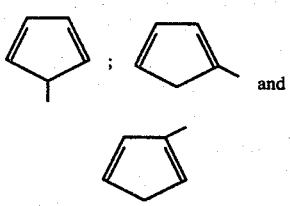

and

In addition, other isomers of the dimethylcyclopentadiene structure exist.

The ester derivatives, e.g., the formate, acetate and propionate derivatives of dimethylcyclopentadiene of our invention having the structures:

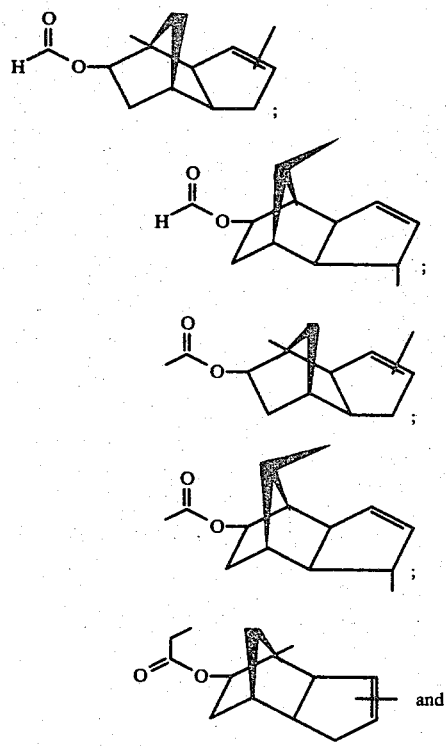

and

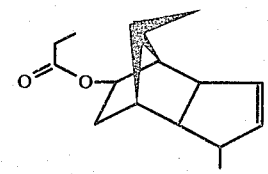

may be prepared by reacting one or more of the isomers of dimethylcyclopentadiene as set forth above with an appropriate alkanoic acid or mixture of alkanoic acids in the presence of a protonic acid or a Lewis acid. Examples of protonic acids useful in this reaction are sulfuric acid, phosphoric acid, para toluene sulfonic acid, methane sulfonic acid and acid clays, and acid ion exchange resins. Examples of Lewis acids which may be used are borontrifluoride, borontrifluoride etherate, zinc chloride and stannic chloride.

The reaction temperature may vary from about 0° C. up to about 50° C. with a reaction temperature of approximately 10° C. being preferred and the resulting yield is from 25 up to 50% by weight of the theoretical yield based on the amount of methyl cyclopentadiene dimer reactant present.

The concentration of acid, whether it be Lewis acid or protonic acid catalyst in the reaction mass, may vary from 0.01% up to 1 mole percent based on the weight of the reaction mass. The mole ratio of methyl cyclopentadiene dimer:carboxylic acid may vary from about 1:1 up to about 1:3 moles methyl cyclopentadiene dimer:carboxylic acid.

The resulting esters may also be prepared using esterification reagents other than alkyl carboxylic acids, for example, alkanoic acid anhydrides and mixed alkanoic acid anhydrides, such as, acetic anhydride, propionic anhydride and mixed acetic-propionic anhydride. In the alternative, other esterification reagents may be used, such as acyl halides, for example, acetyl chloride, acetyl bromide, propionyl chloride and propionyl bromide. When acylating agents, such as alkanoic acid anhydrides and acyl halides are used, the mole ratio of dimethyl bicyclopentadiene dimer:esterifying reagent preferably is about 1:1.

The alcohol derivatives of the substituted tricyclodecane derivatives of our invention having the structures:

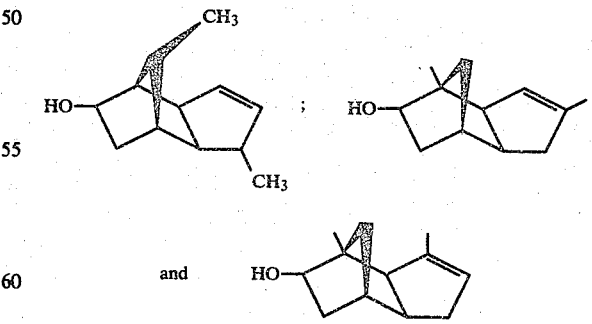

are prepared by hydrolyzing the esters prepared as indicated above. The hydrolysis takes place in the presence of a strong alkali metal hydroxide, such as 10 up to 50% by weight sodium hydroxide. It is preferred that from 1 up to 2 moles of sodium hydroxide be used per mole of ester derivative. The hydrolysis preferably also takes place from about 40° C. up to reflux, usually about 100°-120° C. as a maximum.

Instead of carrying out the reaction of two steps; first forming the ester and then hydrolyzing the ester to form the alcohol using the dimethyl bicyclopentadiene derivative as a starting reactant, the entire reaction can be done using one reactor without isolation of the ester; and this one reactor reaction preferably is carried out using the formate ester as an intermediate. In summary, the reaction sequence is illustrated by the following two reactions:

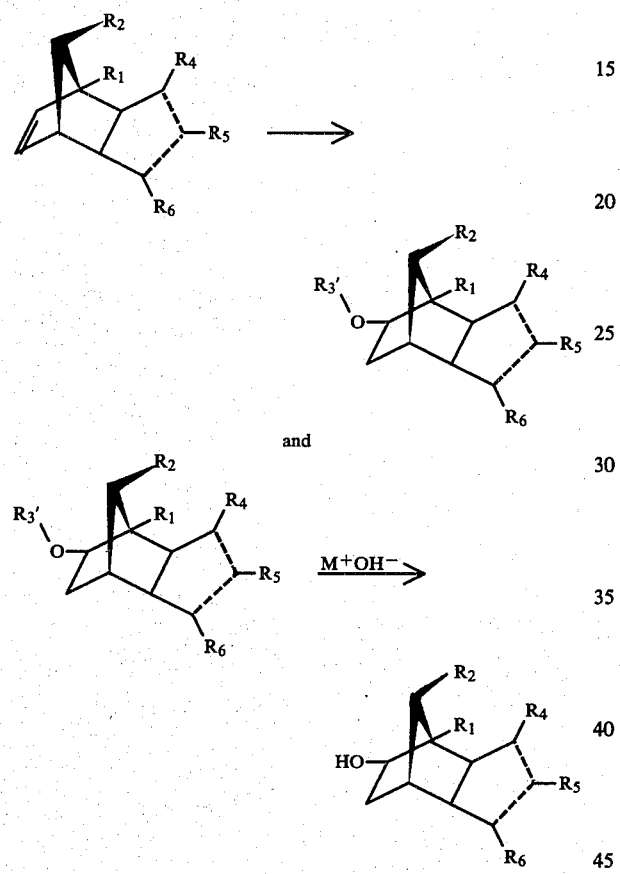

wherein one of $R_1$ or $R_2$ is methyl and the other of $R_1$ or $R_2$ is hydrogen and wherein one of $R_4$, $R_5$ and $R_6$ is methyl and the other two of $R_4$, $R_5$ and $R_6$ is hydrogen; wherein $R_3'$ is $C_1$-$C_3$ acyl and wherein M represents alkali metal, such as sodium, potassium and lithium, wherein one of the dashed lines represents a carbon-carbon single bond and the other of the dashed lines represents a carbon-carbon double bond.

The reaction to form the ether derivative of the methyl cyclopentadiene of our invention according to the reaction:

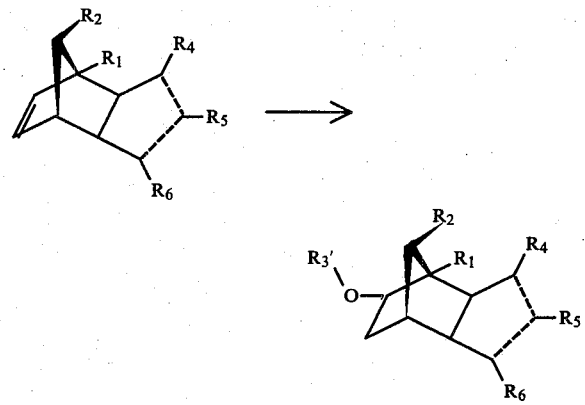

wherein $R_3'$ represents $C_2$-$C_4$ alkyl or $C_3$-$C_4$ alkenyl is carried out under conditions similar to those for preparation of the ester with the exception that, in general, the temperature of reaction is somewhat higher. The reaction is carried out between a $C_2$-$C_4$ alkanol or a $C_3$ or $C_4$ alkenol and one or more of the dimethyl bicyclopentadiene derivatives as enumerated above. It is preferred to use from about 1 up to 3 moles of alkanol or alkenol per mole of dimethyl dicyclopentadiene dimer. It is preferred that the catalyst be either a Lewis acid, such as boron trifluoride, boron trifluoride etherate, zinc chloride or stannic chloride or a protonic acid, such as sulfuric acid, para toluene sulfonic acid or phosphoric acid. It is further preferred that the reaction temperature be from about 25° C. up to reflux temperature, with reflux temperature being between about 100° and 125° C.

The ketone derivative of the dimethyl dicyclopentadiene dimer of our invention having the structures:

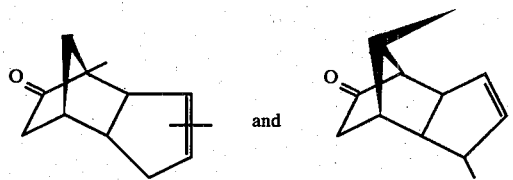

are prepared by oxidation of the corresponding alcohols using oxidizing agents, such as copper chromite or Jones reagents. The reaction sequence is illustrated thusly:

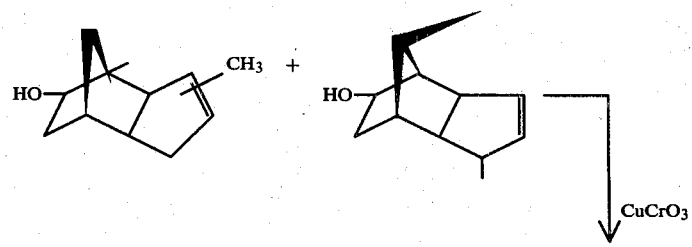

-continued

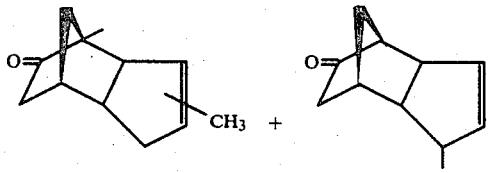

Also useful is sodium dichromate, Jones reagent or $CrO_3$ the like. The reaction that takes place is a chemical oxidation wherein equivalent quantities of oxidizing agent, e.g., sodium dichromate and alcohol are utilized. When copper chromite is used, the reaction is in the nature of a catalytic dehydrogenation. Thus, a catalytic quantity of copper chromite is all that is necessary. The reaction when carried out using catalytic dehydrogenation is preferably carried out at a temperature of between 180° and 220° C. at atmospheric pressure. When using the oxidizing reaction and using such oxidizing reagents as sodium dichromate or chromate trioxide, the reaction temperature is preferably in the range of from about 20° C. up to about 80° C. with the use of a solvent being preferred, e.g., toluene or methyl dichloride. Pyrididiumchlorochromate may also be used as an oxidizing agent with the temperature of reaction being in the range of between about 25° C. and about 100° C.

In summary, the reaction of the hydroxy derivative of the dimethyl bicyclopentadiene to the keto derivative of the dimethyl bicyclopentadiene derivative of our invention is illustrated according to the reaction:

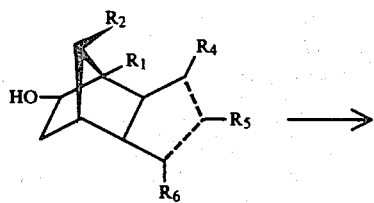

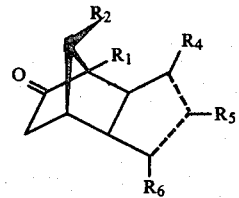

wherein one of $R_1$ or $R_2$ is methyl and the other of $R_1$ or $R_2$ is hydrogen; and wherein one of $R_4$, $R_5$ and $R_6$ is methyl and the other two of $R_4$, $R_5$ and $R_6$ are hydrogen, wherein one of the dashed lines represents a carbon-carbon single bond and the other of the dashed lines represents a carbon-carbon double bond.

In producing the compounds having the structures:

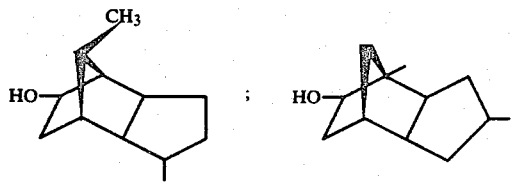

-continued

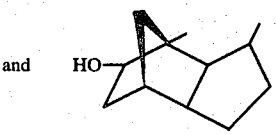

compounds having the structures:

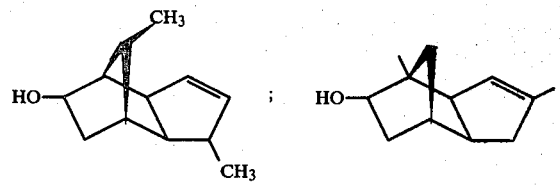

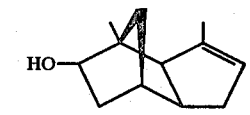

or mixtures thereof are preferably reduced using a reducing agent, such as hydrogen under pressure in the presence of a hydrogenation catalyst, such as Raney nickel, and supported palladium or platinum on carbon or calcium carbonate (e.g., a "Lindlar" catalyst of 5% palladium on calcium carbonate). By the same token, ethers and esters may also be hydrogenated whereby the double bond on the dimethyl bicyclopentadiene derivative is reduced to a carbon-carbon single bond according to the reaction:

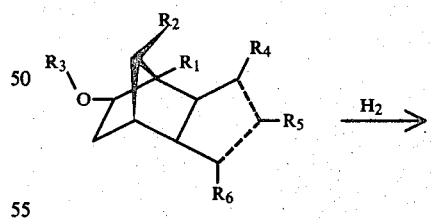

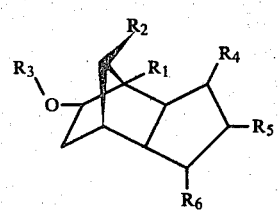

wherein $R_3$ represents hydrogen, $C_3$ or $C_4$ alkenol or $C_2$-$C_4$ alkyl or $C_1$-$C_3$ acyl; one of $R_1$ or $R_2$ is methyl and the other of $R_1$ or $R_2$ is hydrogen; and one of $R_4$, $R_5$ and $R_6$ is methyl and the other two of $R_4$, $R_5$ and $R_6$ represents hydrogen; wherein one of the dashed lines represents a carbon-carbon single bond and the other of the dashed lines represents a carbon-carbon double bond. When R$_3$ is alkenyl, the hydrogenation reaction will produce a mixture of alkyl and alkenyl ethers, the proportion of alkyl ether in the mixture being a function of the extent (time, pressure and temperature) of hydrogenation carried out. A long period of time of hydrogenation coupled with high pressure and high temperature will yield total elimination of the carbon-carbon double bonds in the molecule thereby yielding alkyl esters of dimethyl bicyclopentane derivatives, either in pure form or in admixture themselves depending upon the nature of the dimethyl bicyclopentadiene starting reactant used. The range of reaction temperature may vary from about 10° C. up to about 50° C. with a preferred reaction pressure of from about 25 psig up to 300 psig. It is preferred that the hydrogenation reaction be carried out in the presence of an inert solvent, such as isopropyl alcohol, ethyl alcohol, methyl alcohol or n-butanol. When such a solvent is used, it is preferred that the ratio of the dimethyl bicyclopentadiene derivative:solvent (weight:weight) be between about 1:1 and 3:1 with a preferred ratio being 2.5:1.

In producing carboalkoxy esters (e.g., "carbonates" of the dimethyl bicyclopentadiene derivatives of our invention having the structures:

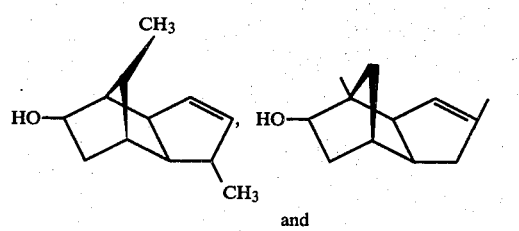

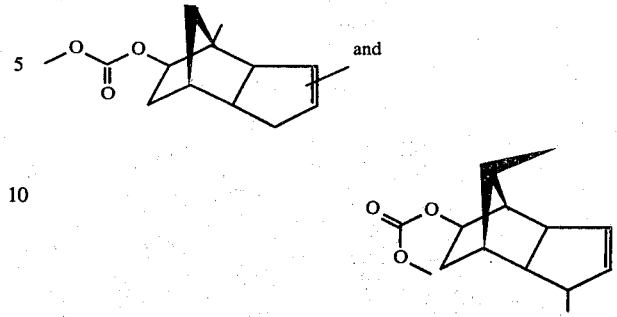

the starting materials are the hydroxyl derivatives of the dimethyl bicyclopentadiene derivatives of our invention having the structures:

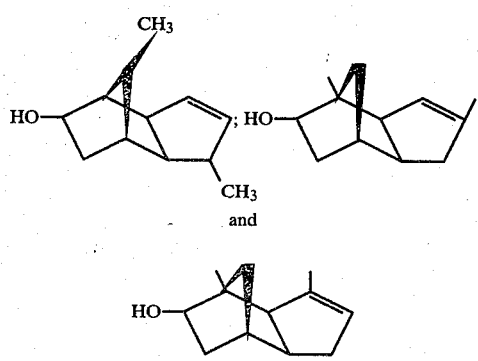

These compounds may either first be reacted with such materials as methyl chloroformate to form the methyl carbonate derivatives having the structures:

in a 1:1 mole ratio of reactants using ambient temperature and pressure or the reaction (in order to effect a higher yield . . . quantitative yields) may be carried out by first reacting the hydroxyl derivatives of the dimethyl bicyclopentadiene derivatives of our invention having the structures:

with an alkali metal hydride, such as lithium hydride thereby forming the alkali metal salts of the dimethyl bicyclopentadiene derivatives of our invention having the structures:

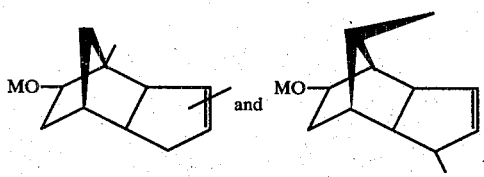

wherein M is sodium, potassium or lithium. These organometallic derivatives may in admixture or individually be reacted with dialkyl carbonate such as dimethyl carbonate thereby producing the desired carbonate derivatives of the dimethyl bicyclopentadienes of our invention according to the reaction:

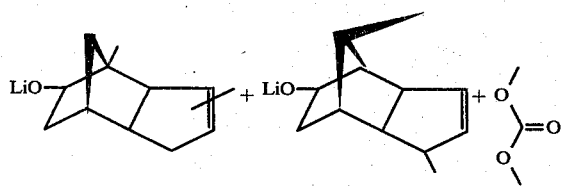

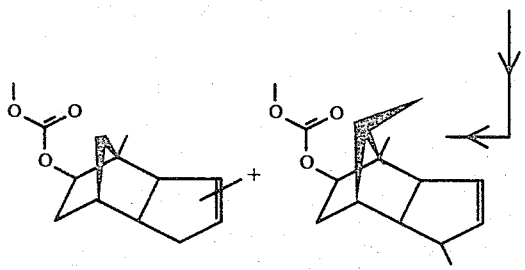

The temperature range most preferred for the foregoing reaction when reacting the alkali metal hydride with the alcohol derivative of the dimethyl bicyclopentadiene is from about 40° C. up to about 70° C. and it is most preferred to carry out the reaction in an inert cosolvent, such as toluene or xylene. After the reaction is completed, the second reaction with the dialkyl carbonate and the organometallic derivative should take place at reflux temperature in the same cosolvent as used in the first reaction with the alkali metal hydride. Thus, for example, if the cosolvent is toluene, the reaction should take place at about reflux or between the temperatures of about 90° C. and about 115° C. The period of time necessary for the reaction to go to completion is between about 2 and about 5 hours. The reaction pressure is preferably atmospheric but super atmospheric pressures may be utilized without any resultant decrease in the yield of desired reaction product.

At the end of each of the foregoing reactions, the reaction product may, if desired, by separated from the resultant reaction mass as by fractional distillation or preparative GLC (vapor phase chromatography). However, if the desired reaction product as above is to be utilized as a reaction intermediate, the necessity of careful rectification of the reaction product in order to achieve odor acceptable substances or flavor acceptable substances is not necessary since the resultant reaction product will be further reacted.

It will be appreciated from the present disclosure that the substituted tricyclodecane derivative according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify the organoleptic character.

The term "enhance" is intended herein to mean the intensification (by use of the substituted tricyclodecane derivative of our invention) of a flavor or aroma note or nuance in a tobacco flavor or foodstuff or perfume composition or a perfumed article without changing the quality of said note or nuance.

A "flavoring composition" is taken to mean one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible materials for man or animals, which materials usually do, not need not, have nutritional value. Thus, foodstuffs includes meats, gravies, soups, convenience foods, malt, alcoholic, and other beverages, milk and dairy products, seafoods including fish, crustaceans, mollusks, and the like, candies, vegetables, cereals, soft drinks, snacks, dog and cat food, other veterinary products, and the like.

The substituted tricyclodecane derivatives of our invention are also a useful tobacco flavorant and flavor enhancer.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the substituted tricyclodecane derivatives of our invention are useful include those designed or used for smoking such as in cigarette, cigar and pipe tobacco, as well as products such as snuff, chewing tobacco, and the like.

When the substituted tricyclodecane derivatives of this invention are used in a flavoring composition, they can be combined with conventional flavoring materials or adjuvants. Such co-ingredients or flavoring adjuvants are well known in the art for such use and have been extensively described in the literature. Requirements of such adjuvant materials are: (1) that they be non-reactive with the substituted tricyclodecane derivatives of our invention; (2) that they be organoleptically compatible with the substituted tricyclodecane derivatives of our invention whereby the flavor of the ultimate consumable material to which the substituted tricyclodecane derivatives are added is not detrimentally affected by the use of the adjuvant and (3) that they be ingestibly acceptable, and thus non-toxic or not otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids; alcohols, including primary and secondary alcohols, esters; carbonyl compounds including ketones and aldehydes; lactones; other cyclic organic materials including benzene derivatives, alicyclic compounds, heterocyclics such as furans, pyridines, pyrazines and the like; sulfur-containing materials including thiols, sulfides, disulfides and the like; proteins; lipids, carbohydrates; so-called flavor potentiators such as monosodium glutamate, guanylates, and inosinates; natural flavoring materials such as cocoa, vanilla and caramel; essential oils and extracts such as anise oil; clove oil; and the like; and artificial flavoring materials such as vanillin; and the like.

Specific preferred flavor adjuvants are as follows:
Ethyl-2-methyl butyrate;
Vanillin;
Butyl valerate;
2,3-Diethyl pyrazine;
Methyl cyclopentenolone;
Benzaldehyde;
Valerian Oil Indian; and
Propylene glycol When used in perfumery, in order to alter, modify or enhance the aroma of perfume compositions, or perfumed articles the substituted tricyclodecane derivatives of our invention can be used to contribute patchouli-like, peppery, woody, fruity and camphoraceous aromas. As an olfactory agent, the substituted tricyclodecane derivatives of this invention can be formulated into or used as a component of a "perfume composition".

The term perfume composition is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain (a) the main note of the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low boiling fresh smelling materials.

In perfume compositions, the individual component will contribute its particular olfactory characteristics but the overall effect of the perfume composition will be the sum of the effect of each ingredient. Thus, the substituted tricyclodecane derivatives of this invention can be used to alter, modify or enhance the aroma characteristics of a perfume composition, for example, by high-lighting or moderating the olfactory reaction contributed by another ingredient in the composition.

The amount of the substituted tricyclodecane derivatives of this invention which will be effective in perfume compositions depends on many factors, including the other ingredients, their amounts and the effects which are desired. It has been found that perfume compositions containing as little as 1 percent of the substituted tricyclodecane derivatives of this invention, or even less, can be used to impart a patchouli scent with peppery, woody, fruity and camphoraceous notes to soaps, cosmetics, and other products. The amount employed can range up to 50% or higher and will depend on considerations of cost, nature of the end product, the effect desired on the finished product and particular fragrance sought.

The substituted tricyclodecane derivatives of this invention can be used alone or in a perfume composition as an olfactory component in detergents, and soaps, space odorants and deodorants; perfumes; colognes; toilet waters; bath salts; hair preparations such as lacquers, brilliantines, pomades, and shampoos, cosmetic preparations such as creams, deodorants, hand lotions, and sun screens; powders such as talcs, dusting powders, face powder, and the like. When used as an olfactory component of a perfumed article, as little as 0.01 percent of one or more of the substituted tricyclodecane derivatives will suffice to impart a patchouli aroma with peppery, woody, fruity and camphoraceous notes. Generally, no more than 0.5 percent is required.

In addition, the perfume composition can contain a vehicle or carrier for the substituted tricyclodecane derivatives alone or with other ingredients. The vehicle can be a liquid such as an alcohol such as ethanol, a glycol such as propylene glycol, or the like. The carrier can be an absorbant solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims.

EXAMPLE I

PREPARATION OF HEXAHYDRO-5-FORMYLOXY-2 (AND 3),4-DIMETHYL-4,7-METHANOINDENE

Reaction:

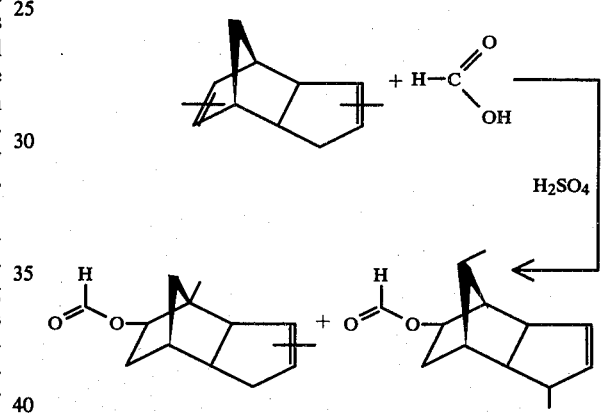

Methyl cyclopentadiene dimer (1072 grams) is slowly added over a two-hour period to a stirred solution of 95% formic acid (480 grams) and sulfuric acid (50 grams) at 6° to 10° C. The mass is stirred for two hours at 5° C. and then poured into two liters of water. The organic layer is washed twice with water and distilled through a short column to afford 460 grams of hexahydro-5-formyloxy-2 (and 3),4-dimethyl-4,7-methanoindene (b.p. 100° to 135° C. at 33 mm Hg. pressure).

Figure 1:
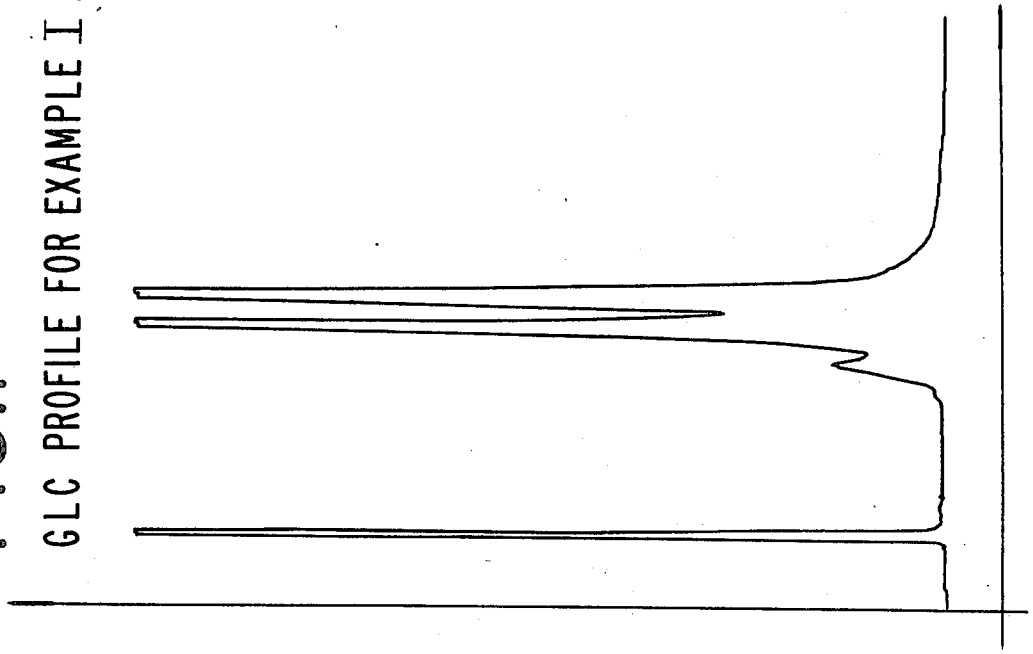
FIG. 1 represents the GLC profile for the reaction product produced according to Example I primarily containing the compound having the structure.

FIG. 1 is the GLC profile of the product (200° C. isothermal; ¼"×10' 10% SE-30 packed column).

FIG. 2 shows the NMR spectrum of hexahydro-5-formyloxy-2 (and 3),4-dimethyl-4,7-methanoindene.

FIG. 3 shows the IR spectrum of hexahydro-5-formyloxy-2 (and 3),4-dimethyl-4,7-methanoindene.

EXAMPLE II

PREPARATION OF HEXAHYDRO-5-ACETOXY-2 (AND 3),4-DIMETHYL-4,7-METHANOINDENE

Reaction:

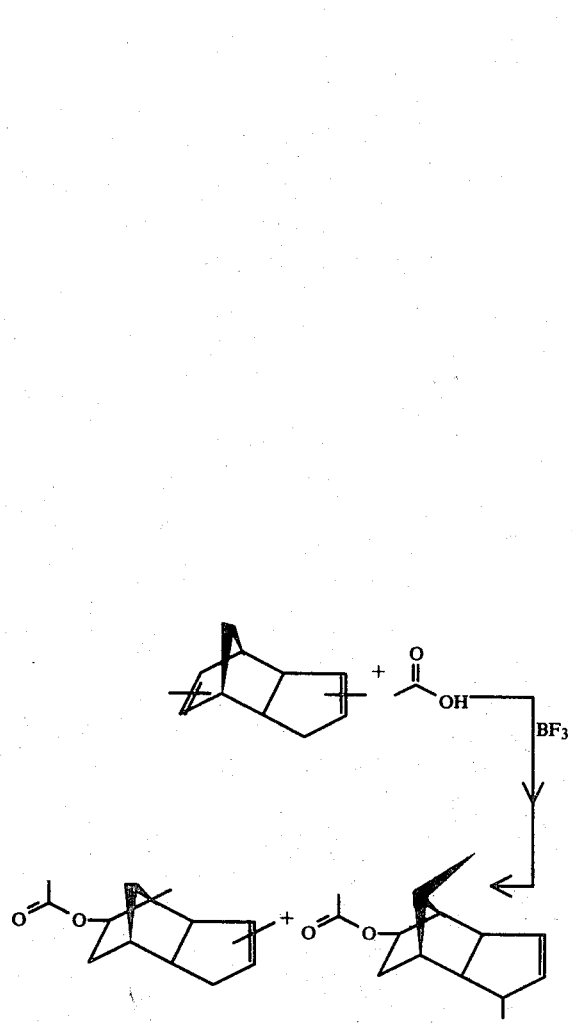

Methylcyclopentadiene dimer (640 grams) is added to a stirred solution of acetic acid (300 grams), toluene (400 ml), and boron trifluoride etherate (80 grams) at 45° C. over a two-hour period. The mass is stirred at 45° C. for one hour and then poured into one liter of water and 500 ml of toluene. The organic layer is washed two times with water, one time with 10% sodium bicarbonate, ond one time with water again. The organic layer is rushed over and the crude product is fractionally distilled through a 1½"×12' packed column to afford 373 grams of hexahydro-5-acetoxy-2 (and 3),4-dimethyl-4,7-methanoindene (b.p. 94° C. at 1.7 mm Hg. pressure).

FIG. 4 shows the GLC trace of hexahydro-5-acetoxy-2 (and 3),4-dimethyl-4,7-methanoindene (200° C. isothermal ¼"×10' 10% SE-30 packed column).

FIG. 5 shows the NMR spectrum of hexahydro-5-acetoxy-2 (and 3),4-dimethyl-4,7-methanoindene.

FIG. 6 shows the IR spectrum of hexahydro-5-acetoxy-2 (and 3),4-dimethyl-4,7-methanoindene.

EXAMPLE III

PREPARATION OF HEXAHYDRO-5-HYDROXY-2 (AND 3),4-DIMETHYL-4,7-METHANOINDENE

Reaction:

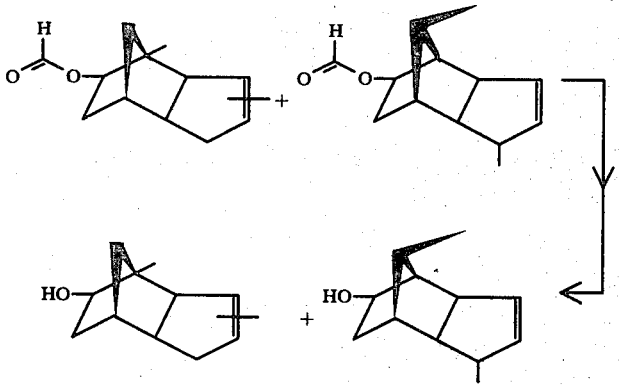

A solution of 400 grams of hexahydro-5-formyloxy-2 (and 3),4-dimethyl-4,7-methanoindene, 480 grams of 50% sodium hydroxide, 400 ml of toluene, and 100 ml of methanol are heated at reflux for two hours. The mass is cooled. The organic layer is separated and washed two times with water. Distillation through a 1½"×12' packed column affords 365 grams of product (b.p. 88°-106° C. at 3 mm Hg. pressure).

FIG. 7 shows the GLC trace of hexahydro-5-hydroxy-2 (and 3),4-dimethyl-4,7-methanoindene (220° C. isothermal, ¼"×10' 10% SE-30 packed column).

FIG. 8 shows the NMR spectrum of hexahydro-5-hydroxy-2 (and 3),4-dimethyl-4,7-methanoindene.

FIG. 9 shows the IR spectrum of hexahydro-5-hydroxy-2 (and 3),4-dimethyl-4,7-methanoindene.

EXAMPLE IV

PREPARATION OF HEXAHYDRO-5-HYDROXY-2 (AND 3),4-DIMETHYL-4,7-METHANOINDENE

Reaction:

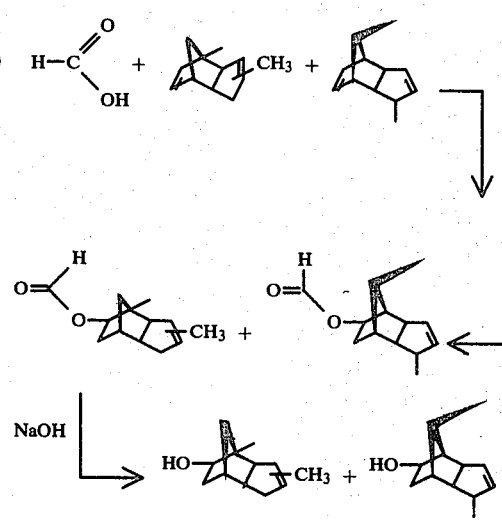

Methyl cyclopentadiene dimer (6480 grams) is slowly added over a five hour period to a stirred solution of 95% formic acid (2905 grams) and sulfuric acid (294 grams) at 6° to 10° C. The mass is stirred 30 minutes at 5° C. and then poured into 3 liters of 10% salt solution with stirring. The organic layer is added to a stirred solution of 4800 grams of 50% sodium hydroxide solution and 1 liter of methanol. The mixture is heated at reflux for 3 hours, whereupon it is poured into 3 liters of salt solution and 1 liter of toluene. The organic layer is rushed over and distilled to afford 3600 grams of product (b.p. 88°-100° C., 3 mm Hg. pressure).

EXAMPLE V

PREPARATION OF HEXAHYDRO-5-HYDROXY-2 (AND 3),4-DIMETHYL-4,7-METHANOINDENE

Reaction:

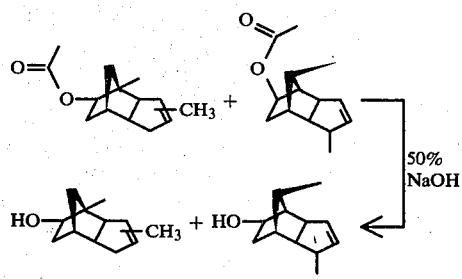

A solution of 474 grams of hexahydro-5-acetoxy-2-(and 3),4-dimethyl-4,7-methanoindene, 240 grams of 50% sodium hydroxide solution, 15 grams of cetyl trimethyl ammonium chloride, and 300 ml of toluene is heated at reflux for 6 hours. The reaction mass is poured into one liter of water. The organic layer is washed once with water and rushed over. Fractional distillation through a 1½"×12' packed column affords 339 grams of hexahydro-5-hydroxy-2 (and 3),4-dimethyl-4,7-methanoindene (b.p. 75°-80° C., 1.4 mm Hg. pressure).

EXAMPLE VI

PREPARATION OF 3a,6,7,7a-TETRAHYDRO-2 (AND 3),4-DIMETHYL-4,7-METHANOINDENE-5(4H)-ONE

Reaction:

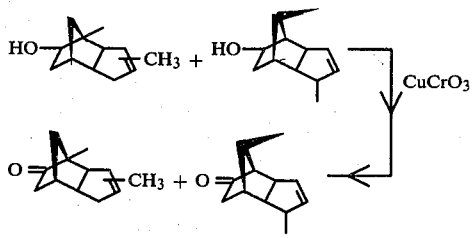

A mixture of 500 grams of hexahydro-2(and 3),4-dimethyl-4,7-methanoindene, 20 grams of Primol$^R$, and 10 grams of copper chromite are heated slowly to 220°-240° C. Hydrogen gas is evolved over a period of 4 hours. The reaction mass is cooled and the organic mass distilled through a 1½"×12' packed column to afford 460 grams of 3a,6,7,7a-tetrahydro-2 (and 3),4-dimethyl-4,7-methanoindene-5(4H)-one (b.p. 85° C. at 1.1 mm Hg. pressure). The material solidifies upon standing.

FIG. 10 shows the GLC profile of 3a,6,7,7a-tetrahydro-2 (and 3),4-dimethyl-4,7-methanoinden-5(4H)-one.

FIG. 11 shows the mass spectrum of 3a,6,7,7a-tetrahydro-2 (and 3),4-dimethyl-4,7-methanoinden-5(4H)-one.

FIG. 12 shows the IR spectrum of 3a,6,7,7a-tetrahydro-2 (and 3),4-dimethyl-4,7-methanoinden-4(4H)-one.

EXAMPLE VII

PREPARATION OF HEXAHYDRO-2 (AND 3),4-DIMETHYL-5-PROPIONOXY-4,7-METHANOINDENE

Reaction:

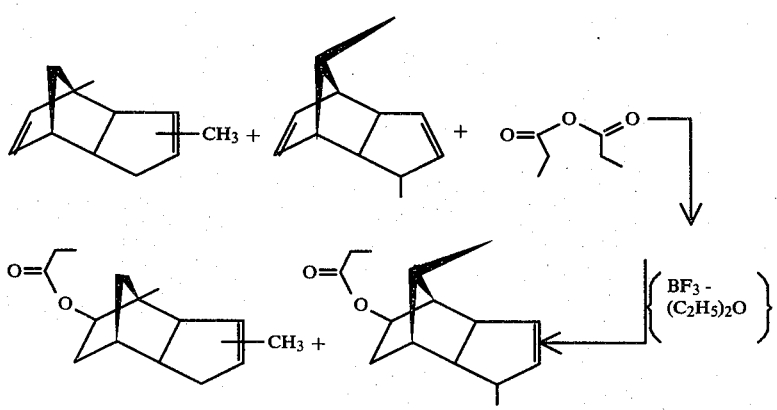

Methylcyclopentadiene dimer (320 grams) is added to a solution of boron trifluoride etherate (20 ml), propionic acid (163 grams) and toluene (200 ml) at 30° C. over a 90-minute period. The mass is stirred three hours at 30° C. and then poured into 500 ml of salt solution. The organic layer is washed with water and then washed with dilute sodium bicarbonate solution. The organic mass is rushed over and fractionally distilled through a 1½"×1' packed column to afford 285 grams of hexahydro-2 (and 3),4-dimethyl-5-propionoxy-4,7-methanoindene (b.p. 100" C. at 1 mm Hg. pressure).

FIG. 13 represents the GLC profile of the crude reaction product containing hexahydro-2 (and 3,)4-dimethyl-5-propionoxy-4,7-methanoindene (200° C. isothermal, ¼'×10' 10% SE-30 packed column).

FIG. 14 shows the NMR spectrum of hexahydro-2 (and 3),4-dimethyl-5-propionoxy-4,7-methanoindene.

FIG. 15 shows the IR spectrum of hexahydro-2 (and 3),4-dimethyl-5-propionoxy-4,7-methanoindene.

EXAMPLE VIII

PREPARATION OF HEXAHYDRO-5-ALLYLOXY-2 (AND 3),4-DIMETHYL-4,7-METHANOINDENE

Reaction:

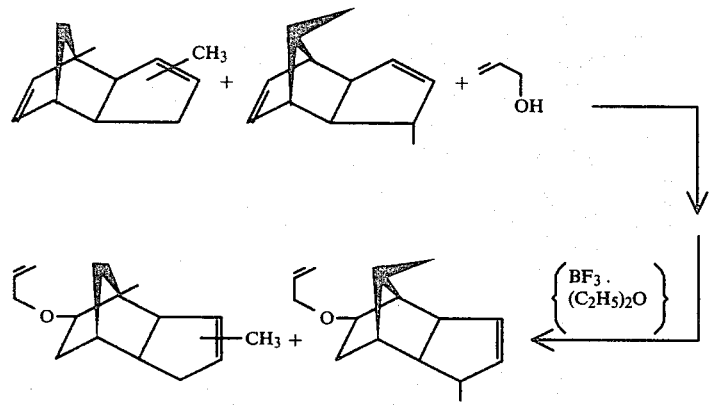

Methyl cyclopentadiene dimer (320 grams) is added to a solution of boron trifluoride etherate (40 grams), allyl alcohol (174 grams) and toluene (200 ml) at 60° C. over a one-hour period. The mass is stirred at 60° C. for 90 minutes and poured into 500 ml of water. The organic layer is washed twice with water and then rushed over. Fractional distillation through a 1½"×12' packed column affords 375 grams of hexahydro-5-allyloxy-2 (and 3),4-dimethyl-4,7-methanoindene (b.p. 84° C. at 1 mm Hg. pressure).

FIG. 16 represents the GLC profile of hexahydro-5-allyloxy-2 (and 3),4-dimethyl-4,7-methanoindene (200° C. isothermal, ¼"×10' 10% SE-30 packed column).

FIG. 17 shows the NMR spectrum of hexahydro-5-allyloxy-2 (and 3),4-dimethyl-4,7-methanoindene.

FIG. 18 shows the IR spectrum of hexahydro-5-allyloxy-2 (and 3),4-dimethyl-4,7-methanoindene.

EXAMPLE IX

PREPARATION OF HEXAHYDRO-5-BUTYLOXY-2 (AND 3),4-DIMETHYL-4,7-METHANOINDENE

Reaction:

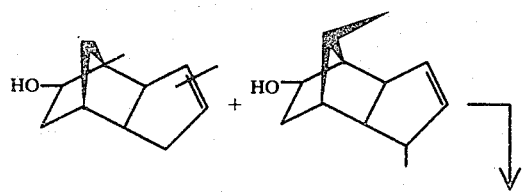

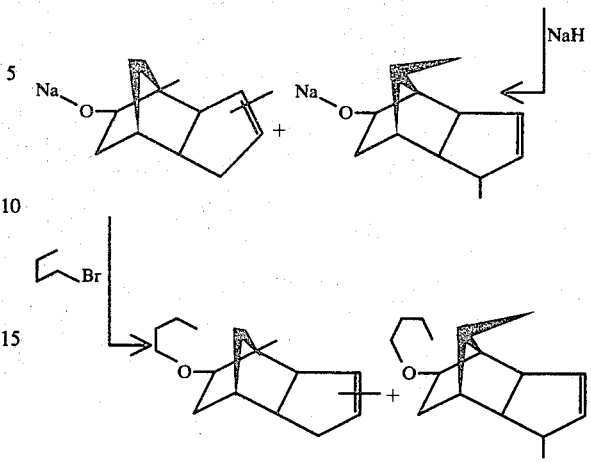

A solution of 352 grams of hexahydro-5-hydroxy-2(and 3),4-dimethyl-4,7-methanoindene in 300 ml of toluene is dropwise added at 80° C. over a 90-minute period to a stirred slurry of 96 grams of 53% sodium hydride in 700 ml of toluene. Hydrogen gas evolves as the addition proceeds. The reaction mass is heated at reflux for one hour after the addition is completed. The mass is cooled to 75° C. A mixture of 1-bromobutane (304 grams) and 10 grams of cetyl trimethyl ammonium chloride are added over a one-hour period. The mass is heated at 75° C. for 5 hours. The mixture is cooled and poured into 1 liter of water. The organic layer is washed twice and rushed over. Fractional distillation through a 1½"×12' packed column affords 384 grams of hexahydro-5-butyloxy-2 (and 3),4-dimethyl-4,7-methanoindene (b.p. 105° C. at 1.6 mm Hg. pressure).

FIG. 19 represents the GLC profile of hexahydro-5-butyloxy-2 (and 3),4-dimethyl-4,7-methanoindene (200° C. isothermal, ¼"×10" 10% SE-30 packed column).

FIG. 20 represents the NMR spectrum of hexahydro-5-butyloxy-2 (and 3),4-dimethyl-4,7-methanoindene.

FIG. 21 represents the IR spectrum of hexahydro-5-butyloxy-2 (and 3),4-dimethyl-4,7-methanoindene.

EXAMPLE X

PREPARATION OF HEXAHYDRO-5-ISOPROPOXY-2 (AND 3),4-DIMETHYL-4,7-METHANOINDENE

Reaction:

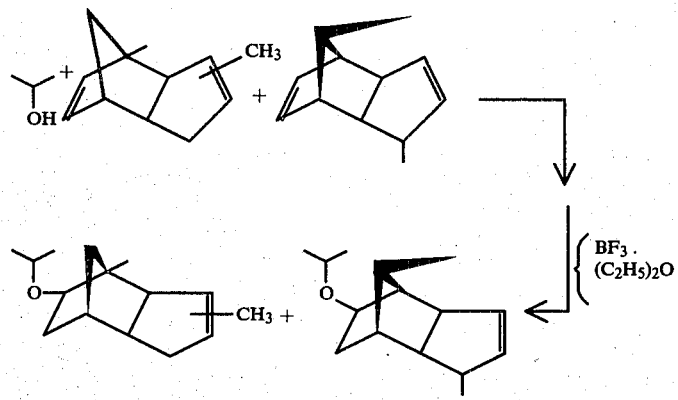

Methyl cyclopentadiene dimer (320 grams) is added to a stirred solution of boron trifluoride etherate (20 ml), isopropanol (132 grams) and toluene (200 grams) at 60° C. over a 1-hour period. The mass is stirred at 60° C. for three hours and then poured into 1 liter of saturated salt solution. The organic layer is washed twice with water and then rushed over. Fractional distillation affords 222 grams hexahydro-5-isopropoxy-2 (and 3),4-dimethyl-4,7-methanoindene (b.p. 80° C. at 0.7 mm Hg. pressure).

FIG. 22 represents the GLC profile of the crude reaction product containing hexahydro-5-isopropoxy-2 (and 3),4-dimethyl-4,7-methanoindene.

FIG. 23 represents the NMR spectrum of hexahydro-5-isopropoxy-2 (and 3),4-dimethyl-4,7-methanoindene.

FIG. 24 represents the IR spectrum of hexahydro-5-isopropoxy-2 (and 3),4-dimethyl-4,7-methanoindene.

EXAMPLE XI

PREPARATION OF 5-HYDROXY-2 (AND 3),4-DIMETHYL-4,7-METHANOINDENE

Reaction:

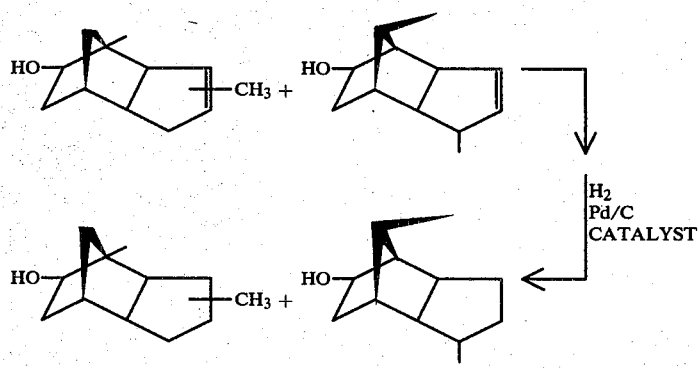

A solution of 500 grams of hexahydro-5-hydroxy-2 (and 3),4-dimethyl-4,7-methanoindene and 200 grams of isopropanol are hydrogenated at 50 psi and 25° C. over 2 grams of 10% palladium on charcoal. After the uptake of 98% of the calculated hydrogen, the solution is filtered and distilled to afford 482 grams of hexahydro-5-hydroxy-2 (and 3),4-dimethyl-4,7-methanoindene (b.p. 99° C. at 2 mm. Hg. pressure).

FIG. 31 represents the NMR spectrum of 5-hydroxy-2 (and 3),4-dimethyl-4,7-methanoindene.

EXAMPLE XII

PREPARATION OF HEXAHYDRO-2 (AND 3),4-DIMETHYL-4,7-METHANOINDEN-5-METHYLCARBONATE

Reactions:

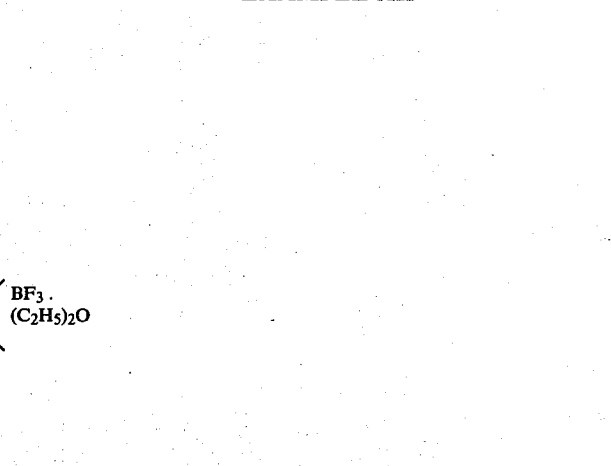

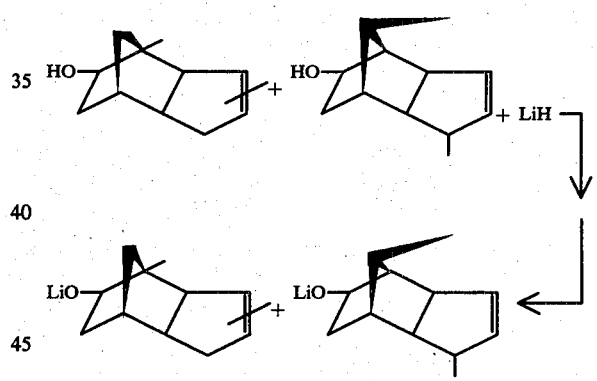

41
-continued

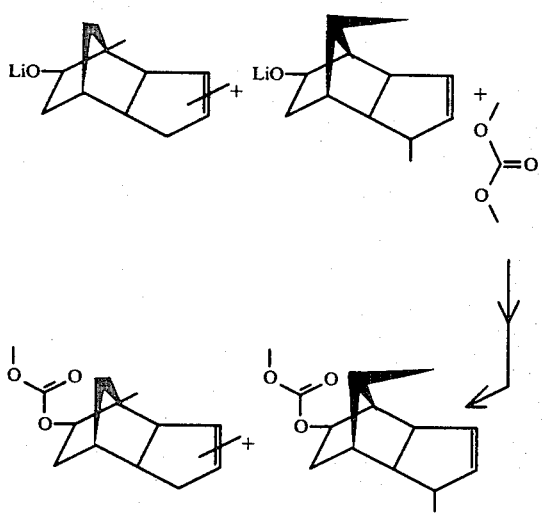

A solution of 356 grams of 5-hydroxy hexahydro-2 (and 3),4-dimethyl-4,7-methanoindene in 500 ml of toluene is added dropwise to a stirred slurry of lithium hydride (24 grams) and 500 ml toluene at 50° C. over a 90-minute period. Hydrogen is eliminated as the addition proceeds. The reaction mass is stirred at 50° C. for one hour whereupon 270 grams of dimethyl carbonate are added over a 30-minute period. The resulting mass is heated to reflux (95° C.) for three hours. 300 ml of solvent are distilled off at atmospheric pressure. The organic solution is cooled and washed two times with water and distilled to afford 187 grams of hexahydro-2 (and 3),4-dimethyl-4,7-methanoinden-5-methyl carbonate (b.p. 115° C., 1.8 mm. Hg. pressure). The material solidifies upon standing.

FIG. 32 represents the GLC profile for the above reaction product.

FIG. 33 represents the NMR spectrum for fraction 5 of the distillate.

FIG. 34 represents the IR spectrum for fraction 5 of the distillate.

FIG. 35 represents the mass spectrum for fraction 5 of the distillate.

EXAMPLE XIII

PATCHOULI PERFUME FORMULATION

The following mixture is prepared:

| Ingredient | Parts by Weight |
|---|---|
| Orange Oil | 50 |
| Beramot Oil | 20 |
| Lime Oil | 100 |
| Neroli Oil | 5 |
| 4-(4-Methyl-4-hydroxyamyl) $\Delta^3$-cyclohexene carboxaldehyde | 5 |
| 2,3,3A,4,5,7A-hexahydro-6,7A,8,8-tetramethyl-1,5-methano-1H-inden-1-ol (prepared according to the process of Example I of U.S. Pat. No. 3,989,760 issued on November 2, 1976) | 100 |
| 1',2',3',4',5',6',7',8'-octahydro 2',3',8',8'-tetramethyl-2'-acetonaphthone isomer mixture produced according to the process of Example VII of Application for U.S. Letters Pat. No. 434,948 filed on January 21, 1974, now U.S. Pat. No. 3,911,018 issued on October 7, 1975 | 50 |
| Gamma Methyl Ionone | 20 |
| 1-acetyl-2,5,5-trimethylcycloheptane produced according to U.S. Pat. No. 3,869,411 issued on March 4, 1975 | 50 |
| Substituted tricyclodecane derivatives prepared according to one of Examples I-XII | 100 | produced according to Example I produced according to Example II produced according to Examples III, IV and V produced according to Example VI produced according to Example VII 43
-continued

| Ingredient | Parts by Weight |
|---|---|

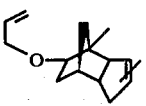
and
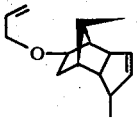

produced according to
Example VIII

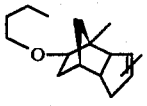
and
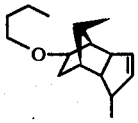

produced according to
Example IX

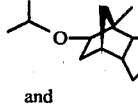
and
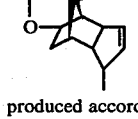

produced according to
Example X

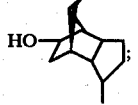

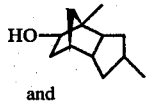
and
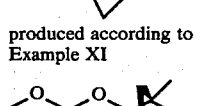

produced according to
Example XI

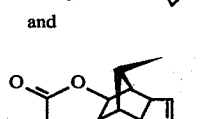
and
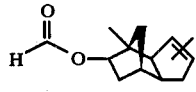

produced according to
Example XII

The substituted tricyclodecane derivatives prepared according to one of Examples I-XII, when added to this formulation in the amount indicated; and also in amounts up to 30% by weight of the total mixture; or in amounts as little as 1.0% by weight of this mixture, imparts aroma characteristics to this patchouli composition, in addition to the patchouli aroma as follows:

TABLE II

| Structure | Fragrance Profile |
|---|---|
| 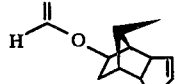 and 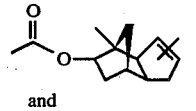 produced according to Example I | A strong maple aroma with pumpkin-like and slightly spicy undertones |
| 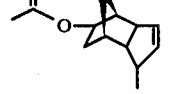 and  produced according to Example II | A fruity, anisic aroma with a raspberry undertone; on dry-out, fruity and berry-like. |
| 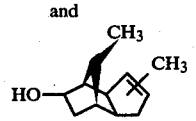 and 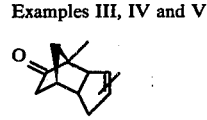 produced according to Examples III, IV and V. | A woody, resinous, camphoraceous patchouli-like aroma reminiscent of patchouli alcohol; with oakmoss undertones then green, and woody and floral and rosey topnotes. |
|  and 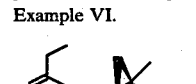 produced according to Example VI. | A fatty, slightly minty and camphoraceous aroma with pith-like and pumpkin nuances as well as woody and piney undertones. |
|  and 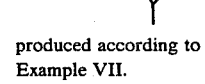 produced according to Example VII. | A green, fruity, creamy, rhubarb stem-like and banana-like aroma. |

TABLE II-continued

| Structure | Fragrance Profile |
|---|---|
| (structure) and (structure) produced according to Example VIII. | A strong, herbaceous aroma with an oily and spicey, green, basil undertone. |
| (structure) and (structure) produced according to Example IX. | A low keyed fruity (banana), spicey (cinnamic), green aroma with sweaty and creamy undertones. |
| (structure) and (structure) produced according to Example X. | A bitter, sweet, herbal, petitgrain-like, lavender and bergamot aroma profile with floral undertones. |
| (structure) and (structure) and (structure) produced according to Example XI. | A minty, spicey, fruity aroma with caryophyllene-like, cedarwood and sandalwood undertones becoming borneol-woody-like on a dry-out. |
| (structure) and (structure) produced according to | A fruity (apple), anisic-like aroma with dry, hay-like and berry-like undertones. |

TABLE II-continued

| Structure | Fragrance Profile |
|---|---|
| Example XII. | |

EXAMPLE XIV

PREPARATION OF SOAP COMPOSITIONS

PART A

A total of 100 g of soap chips produced from unperfumed sodium base toilet soap made from tallow and coconut oil is mixed with 1 g of the substituted tricyclodecane derivative prepared according to one of Examples I–XII until a substantially homogeneous composition is obtained. The soap composition manifests an excellent patchouli-like character having aroma nuances and undertones as indicated in Table III below.

PART B

A total of 100 g of soap chips produced from unperfumed sodium base toilet soap made from tallow and coconut oil is admixed with 1 g of one of the perfume compositions set forth in Example XII until a substantially homogeneous composition is obtained. The soap compositions manifest aromas as indicated in Table II, supra, with a characteristic patchouli aroma.

TABLE III

| Structure | Fragrance Profile |
|---|---|
| (structure) and (structure) produced according to Example I | A strong maple aroma with pumpkin-like and slightly spicy undertones |
| (structure) and (structure) produced according to Example II | A fruity, anisic aroma with a raspberry undertone; on dry-out, fruity and berry-like. |
| (structure) and (structure) produced according to Examples III, IV and V. | A woody, resinous, camphoraceous patchouli-like aroma reminiscent of patchouli alcohol; with oakmoss undertones then green, and woody and floral and rosey topnotes. |

TABLE III-continued

| Structure | Fragrance Profile |
|---|---|
| (structure) and (structure) produced according to Example VI. | A fatty, slightly minty and camphoraceous aroma with pith-like and pumpkin nuances as well as woody and piney undertones. |
| (structure) and (structure) produced according to Example VII. | A green, fruity, creamy, rhubarb stem-like and banana-like aroma. |
| (structure) and (structure) produced according to Example VIII. | A strong, herbaceous aroma with an oily and spicey, green, basil undertone. |
| (structure) and (structure) produced according to Example IX. | A low keyed fruity (banana), spicey (cinnamic), green aroma with sweaty and creamy undertones. |
| (structure) and (structure) produced according to Example X. | A bitter, sweet, herbal, petitgrain-like, lavender and bergamot aroma profile with floral undertones. |
| (structure with CH₃, HO) ; | A minty, spicey, fruity aroma with caryophyllene-like, cedarwood and sandalwood undertones becoming borneol-woody-like on a dry-out. |

TABLE III-continued

| Structure | Fragrance Profile |
|---|---|
| HO— (structure) and HO— (structure) produced according to Example XI. | |
| (structure) and (structure) produced according to Example XII. | A fruity (apple), anisic-like aroma with dry, hay-like and berry-like undertones. |

EXAMPLE XV

PREPARATION OF A DETERGENT COMPOSITION

A total of 100 g of a detergent powder sold under the trademark "RINSO" are mixed with 0.15 g of a perfume composition containing one of the mixtures prepared according to Example XIII until a substantially homogeneous composition having patchouli fragrances with aroma nuances as indicated in Table II is obtained.

EXAMPLE XVI

PREPARATION OF A COSMETIC BASE

A cosmetic powder is prepared by mixing 100 g of talcum powder with 0.25 g of one of the perfume compositions of Examples XIII in a ball mill. A second cosmetic powder is similarly prepared except that the mixture produced in Example XIII is replaced with one of the products produced in one of Examples I–XII, that is, one of the substituted tricyclodecane derivatives of one of Examples I–XII. The cosmetic powder containing the materials of Example XIII have patchouli aromas with dominating undertones and nuances as indicated in Table II, supra, in Example XIII. The cosmetic powder produced using the materials of one of Examples I–XII have patchouli-like characters with aroma nuances as indicated in the Table IV, below:

TABLE IV

| Structure | Fragrance Profile |
|---|---|
| (structure) and (structure) produced according to Example I | A strong maple aroma with pumpkin-like and slightly spicy undertones |

TABLE IV-continued

| Structure | Fragrance Profile |
|---|---|
| (structure) and (structure) produced according to Example II | A fruity, anisic aroma with a raspberry undertone; on dry-out, fruity and berry-like. |
| HO-(structure) and CH₃ CH₃ HO-(structure) produced according to Examples III, IV and V. | A woody, resinous, camphoraceous patchouli-like aroma reminiscent of patchouli alcohol; with oakmoss undertones then green, and woody and floral and rosey topnotes. |
| (structure) and (structure) produced according to Example VI. | A fatty, slightly minty and camphoraceous aroma with pith-like and pumpkin nuances as well as woody and piney undertones. |
| (structure) and (structure) produced according to Example VII. | A green, fruity, creamy, rhubarb stem-like and banana-like aroma. |
| (structure) and (structure) produced according to Example VIII. | A strong, herbaceous aroma with an oily and spicey, green, basil undertone. |
| (structure) and (structure) | A low keyed fruity (banana), spicey (cinnamic), green aroma with sweaty and creamy undertones. |
| produced according to Example IX. | |
| (structure) and (structure) produced according to Example X. | A bitter, sweet, herbal, petitgrain-like, lavender and bergamot aroma profile with floral undertones. |
| CH₃ HO-(structure) ; HO-(structure) and HO-(structure) produced according to Example XI. | A minty, spicey, fruity aroma with caryophyllene-like, cedarwood and sandalwood undertones becoming borneol-woody-like on a dry-out. |
| (structure) and (structure) produced according to Example XII. | A fruity (apple), anisic-like aroma with dry, hay-like and berry-like undertones. |

EXAMPLE XVII

LIQUID DETERGENT CONTAINING SUBSTITUTED TRICYCLODECANE DERIVATIVE PREPARED ACCORDING TO ONE OF EXAMPLES I-XII

Concentrated liquid detergents with warm patchouli-like aromas having undertones and aroma nuances as indicated in Table V, below, containing 0.2%, 0.5% and 1.2% of one of the products produced in accordance with Example I-XII (substituted tricyclodecane derivatives) are prepared by adding appropriate quantities of substituted tricyclodecane derivatives as indicated in Table V below to liquid detergents known as P-87. The warm patchouli aroma of the liquid detergents increases with increasing concentrations of substituted tricyclodecane derivatives as indicated in Table V below with increasing aroma nuances as indicated in Table V below:

TABLE V

| Structure | Fragrance Profile |
|---|---|
| (structures) produced according to Example I | A strong maple aroma with pumpkin-like and slightly spicy undertones |
| (structures) produced according to Example II | A fruity, anisic aroma with a raspberry undertone; on dry-out, fruity and berry-like. |
| (structures) produced according to Examples III, IV and V | A woody, resinous, camphoraceous patchouli-like aroma reminiscent of patchouli alcohol; with oakmoss undertones then green, and woody and floral and rosey topnotes. |
| (structures) produced according to Example VI. | A fatty, slightly minty and camphoraceous aroma with pith-like and pumpkin nuances as well as woody and piney undertones. |
| (structures) produced according to Example VII. | A green, fruity, creamy, rhubarb stem-like and banana-like aroma. |
| (structures) | A strong, herbaceous aroma with an oily and spicey, green, basil undertone. |

TABLE V-continued

| Structure | Fragrance Profile |
|---|---|
| produced according to Example VIII. (structures) | A low keyed fruity (banana), spicey (cinnamic), green aroma with sweaty and creamy undertones. |
| produced according to Example IX. (structures) | A bitter, sweet, herbal, petitgrain-like, lavender and bergamot aroma profile with floral undertones. |
| produced according to Example X. (structures) | A minty, spicey, fruity aroma with caryophyllene-like, cedarwood and sandalwood undertones becoming borneol-woody-like on a dry-out. |
| produced according to Example XI. (structures) | |
| (structures) produced according to Example XII. | A fruity (apple), anisic-like aroma with dry, hay-like and berry-like undertones. |

EXAMPLE XVIII

PREPARATION OF COLOGNE AND HANDKERCHIEF PERFUME

The compositions of Example XVIII are incorporated in colognes having concentrations of 2.0%, 2.5%, 3.0%, 3.5% and 4.0% in 75%, 80%, 85% and 90% aqueous ethanol and into handkerchief perfumes in concentrations of 15%, 20%, 25%, 30%, 35% and 40% (in 80%, 85%, 90% and 95% aqueous ethanol). The use of the compositions of Example XIII affords distinct and definitive patchouli aroma having nuances and undertones as indicated in Table II of Example XIII.

EXAMPLE XIX

COLOGNE AND HANDKERCHIEF PERFUME

The substituted tricyclodecane derivatives produced by the processes of any of Examples I–XII are incorporated into perfumes having concentrations of 2.0%, 2.5%, 3.0%, 4.5% and 5.0% in 75%, 80%, 85% and 95% aqueous ethanol; into handkerchief perfumes at concentrations of 8%, 10%, 12%, 15% and 25% (in 80%, 90%, and 95% aqueous ethanol). Each of the substituted tricyclodecane derivatives produced according to Example I–XII afford distinct and definitive warm patchouli-like aromas with various nuances and undertones as indicated in Table VI to the handkerchief perfumes and to colognes.

TABLE VI

| Structure | Fragrance Profile |
|---|---|
| [structures produced according to Example I] | A strong maple aroma with pumpkin-like and slightly spicy undertones |
| [structures produced according to Example II] | A fruity, anisic aroma with a raspberry undertone; on dry-out, fruity and berry-like. |
| [structures produced according to Examples III, IV and V] | A woody, resinous, camphoraceous patchouli-like aroma reminiscent of patchouli alcohol; with oakmoss undertones then green, and woody and floral and rosey topnotes. |
| [structures produced according to Example VI] | A fatty, slightly minty and camphoraceous aroma with pith-like and pumpkin nuances as well as woody and piney undertones. |
| [structure produced according to Example VII] | A green, fruity, creamy, rhubarb stem-like and banana-like aroma. |
| [structures produced according to Example VII (continued)] | A strong, herbaceous aroma with an oily and spicey, green, basil undertone. |
| [structures produced according to Example VIII] | A low keyed fruity (banana), spicey (cinnamic), green aroma with sweaty and creamy undertones. |
| [structures produced according to Example IX] | A bitter, sweet, herbal, petitgrain-like, lavender and bergamot aroma profile with floral undertones. |
| [structures produced according to Example X] | A minty, spicey, fruity aroma with caryophyllene-like, cedarwood and sandalwood undertones becoming borneol-woody-like on a dry-out. |
| [structures produced according to Example XI] | A fruity (apple), anisic-like aroma with dry, hay-like and berry-like undertones. |

TABLE VI-continued

| Structure | Fragrance Profile |
|---|---|
| produced according to Example XII. | |

EXAMPLE XX

TOBACCO FLAVOR FORMULATIONS

Cigarettes are produced using the following tobacco formulations:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation:

| Ingredients | Parts by Weight |
|---|---|
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| $H_2O$ | 41.90 |

Two portions of 50% of the cigarettes at levels of 10 and 20 ppm, substituted tricyclodecane derivatives as indicated in Table VII below. These cigarettes are hereinafter called "experimental" cigarettes and the cigarettes without the substituted tricyclodecane derivatives are hereinafter called "control" cigarettes. The "control" and "experimental" cigarettes are then evaluated by paired comparison and the results are as follows:

a. In aroma, the "experimental" cigarettes are all found to be more aromatic with nuances as indicated in Table VII below;
b. In smoke flavor, the "experimental" cigarettes are found to be more aromatic, more sweet with bitter, richer and less harsh in the mouth and more cigarette tobacco-like than the "control" cigarettes.

The "experimental" cigarettes containing 20 ppm of each of the compounds prepared according to Examples I–XII as indicated in Table VII below are found to be woody, slightly chemical and mouth coating in the smoke flavor.

TABLE VII

| Structure | Tobacco Flavor Profile |
|---|---|
| 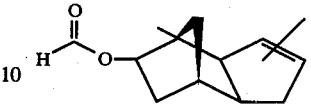 and 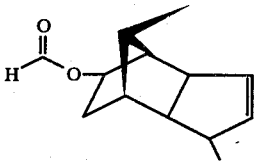 produced according to Example I | A sweet, fruity, citrusy aroma and taste prior to and on smoking in the main stream and the side stream. |
| 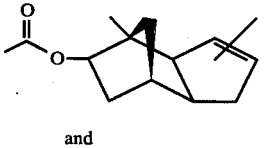 and 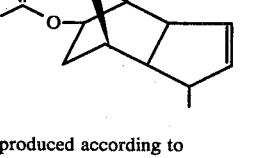 produced according to Example II. | A sweet, woody, spicey, herbaceous aroma and taste both prior to and on smoking in the main stream and side stream. |
| 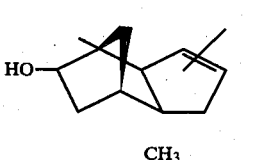 and 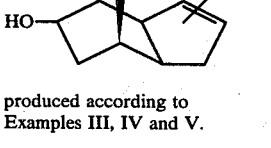 produced according to Examples III, IV and V. | A sweet, herbaceous, spicey, hay-clover-like and woody aroma and taste profile both prior to and on smoking in the main stream and the side stream. |
| 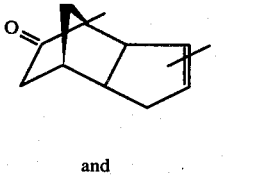 and 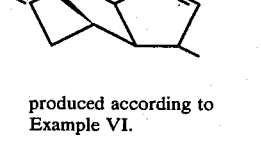 produced according to Example VI. | A sweet, creamy and buttery aroma and taste both prior to and on smoking in the main stream and in the side stream. |

TABLE VII-continued

| Structure | Tobacco Flavor Profile |
|---|---|
| (structure) and (structure) produced according to Example VII. | A sweet, fruity, plum-like, fatty, cucumber-like aroma and taste both prior to and on smoking in the main stream and in the side stream. |
| (structure) and (structure) produced according to Example VIII. | A cocoa-like, sweet, floral and green aroma prior to smoking and a sweet, floral and green aroma on smoking in the main stream and in the side stream. |
| (structure) and (structure) produced according to Example IX. | A sweet, floral, carnation, creamy aroma and taste prior to smoking and a green, floral aroma and taste on smoking in the main stream and in the side stream. |
| (structure) and (structure) produced according to Example X. | A sweet, green, cucumber, melon, pea-like aroma and taste both prior to and on smoking in the main stream and the side stream. |
| (structure with CH₃, HO) and (structure with HO) and (structure with HO) produced according to Example XI. | An earthy, grapefruit peel-like, albedo, camphoraceous aroma and taste both prior to and on smoking in the main stream and in the side stream. |
| (structure) and (structure) produced according to Example XII. | A sweet, woody, camphoraceous, spicey aroma and taste profile both prior to and on smoking in the main stream and in the side stream. |

All cigarettes both "control" and "experimental" are evaluated for smoke flavor with 20 mm cellulose acetate filter. In summary, each of the materials of Examples I–XII enhance the tobacco-like tastes of the blended cigarettes.

EXAMPLE XXI

The following chocolate basic formulation is prepared:

| Ingredients | Parts by Weight |
|---|---|
| Dimethoxy phenol (10% in propylene glycol) | 0.5 |
| Amyl acetate | 0.1 |
| Amyl cinnamate | 0.1 |
| Gamma butyryl lactone | 0.2 |
| Furfural | 0.05 |
| Benzaldehyde | 0.05 |
| Trimethyl pyrazine | 0.05 |
| Phenyl acetic acid | 0.35 |
| Isovaleraldehyde | 1.6 |
| Ethyl maltol | 12.0 |
| Ethyl vanillin | 20.0 |
| 1,3-Propylene Glycol USP | 165.0 |
| Nestle Cocoa Extract | 800.0 |

This basic chocolate flavor is divided into two parts. To the first part is added at the rate of 0.05 ppm the substituted tricyclodecane derivative prepared according to Example II at the rate of 0.05%. To the second part, nothing is added. Both flavors are compared at the rate of 200 ppm. The flavor with the ingredient of Example II has additional very characteristic cocoa butter-like notes both in aroma and taste. These notes are completely missing in the basic chocolate flavor that does not contain the additional material prepared according to Example II. Therefore, the flavor with the material of Example II is preferred as having the desired cocoa butter characteristic.

EXAMPLE XXII

BASIC WALNUT FLAVOR FORMULATION

The following basic walnut flavor formulation is prepared:

| Ingredients | Parts by Weight |
|---|---|
| Cyclotene | 4 |
| Vanillin | 1 |
| Butyl isoyalerate | 2 |
| Benzaldehyde | 6 |
| 2,3-Diethyl pyrazine 10% in food grade ethyl alcohol | 2 |
| Ethyl-2-methyl valerate | 2 |
| Gamma Butyrolactone | 20 |
| Gamma Hexenyl lactone | 10 |
| 2,4-Decadienal (0.1% in food grade ethyl alcohol) | 0.5 |
| 2,4-Heptadienal (0.1% in food grade ethyl alcohol) | 0.5 |
| Butylidene phthalide | 2 |
| Propylene glycol USP | 95 |

The foregoing flavor formulation is divided into two parts. To the first part at the rate of 5% is added the substituted tricyclodecane derivative prepared according to Example V. To the second part, nothing is added. Both flavors are compared by a bench panel at the rate of 20 ppm in water. The flavor with the addition of the product produced according to Example V has a pleasant, fresh walnut kernel taste with a fresh walnut aroma not present in the basic walnut flavor formulation. Therefore the flavor with the material produced according to Example V is preferred as being much more characteristic in walnut flavor by the bench panel (unanimous preference). The flavor is also evaluated at 1 ppm and the same unanimous preference is obtained.

EXAMPLE XXIII

BASIC ORAL HYGIENE FLAVOR FORMULATION

The following basic oral hygiene flavor formulation is prepared:

| Ingredients | Parts by Weight |
|---|---|
| Peppermint oil | 89.0 |
| Spearmint oil | 2.0 |
| Clove oil | 1.0 |
| Anethole | 2.0 |
| Cardamon oil | 0.1 |
| Wintergreen oil | 5.0 |
| Cinnamic aldehyde | 0.9 |

The basic oral hygiene flavor formulation is now divided into two parts. To the first part at the rate of 10% is added the substituted tricyclodecane derivative prepared according to Example VIII, the allyl ether. To the second part, nothing is added. The flavor with the addition of the material produced according to Example VIII has a fresher herbaceous aroma and flavor characteristic with anis seed notes. The peppermint characteristics also appear to be enhanced. Therefore, the flavor with the material produced according to Example VIII is preferred by the bench panel.

EXAMPLE XXIV

PREPARATION OF A SOAP COMPOSITION

One hundred grams of soap chips are produced according to Example V of U.S. Pat. No. 4,058,487 issued on Nov. 15, 1977, as follows:

"The sodium salt of an equal mixture of $C_{10}$–$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated cocoanut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off, and the remaining aqueous solution is drum dried. The resulting solid actives are then blended in a chip mixture with 10 pounds water, 0.2 pounds titanium hydroxide and 0.7 pounds of one of the materials produced according to Examples I–XII as enumerated in the Table below. The chips are then plodded into logs, cut to size and finally stamped into bars having a pH of approximately 6.9.

Each of the perfumed soaps manifests aromas with strong patchouli notes as indicated in the Table VIII below:

TABLE VIII

| Structure | Fragrance Profile |
|---|---|
| (structure of formate ester of tricyclodecane) and (structure of formate ester of tricyclodecene) produced according to Example I | A strong maple aroma with pumpkin-like and slightly spicy undertones |
| (structure of acetate ester of tricyclodecane) and (structure of acetate ester of tricyclodecene) produced according to Example II | A fruity, anisic aroma with a raspberry undertone; on dry-out, fruity and berry-like. |
| (structure of hydroxy tricyclodecane) and (structure of dimethyl hydroxy tricyclodecane with CH$_3$, CH$_3$) produced according to Examples III, IV and V. | A woody, resinous, camphoraceous patchouli-like aroma reminiscent of patchouli alcohol; with oakmoss undertones then green, and woody and floral and rosey topnotes. |

TABLE VIII-continued

| Structure | Fragrance Profile |
|---|---|
| (structure) and (structure) produced according to Example VI. | A fatty, slightly minty and camphoraceous aroma with pith-like and pumpkin nuances as well as woody and piney undertones. |
| (structure) and (structure) produced according to Example VII. | A green, fruity, creamy, rhubarb stem-like and banana-like aroma. |
| (structure) and (structure) produced according to Example VIII. | A strong, herbaceous aroma with an oily and spicey, green, basil undertone. |
| (structure) and (structure) produced according to Example IX. | A low keyed fruity (banana), spicey (cinnamic), green aroma with sweaty and creamy undertones. |
| (structure) and (structure) produced according to Example X. | A bitter, sweet, herbal, petitgrain-like, lavender and bergamot aroma profile with floral undertones. |
| (structure with CH₃, HO) ; | A minty, spicey, fruity aroma with caryophyllene-like, cedarwood and sandalwood undertones becoming borneol-woody-like on a dry-out. |
| (structure HO—) and (structure HO—) produced according to Example XI. | |
| (structure) and (structure) produced according to Example XII. | A fruity (apple), anisic-like aroma with dry, hay-like and berry-like undertones. |

EXAMPLE XXV

PREPARATION OF A DETERGENT COMPOSITION

A total of 100 pounds of a detergent powder prepared according to U.S. Pat. No. 4,058,472 and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol and 40 parts by weight of di-$C_{14}$-$C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of one of the substituted tricyclodecane derivatives produced according to one of Examples I–XII as set forth in Table IX below until a substantially homogeneous composition is obtained. Each of the compositions have excellent patchouli aromas with nuances and undertones as enumerated in the Table below:

| Structure | Fragrance Profile |
|---|---|
| (structure H—C(=O)—O—) and (structure H—C(=O)—O—) produced according to Example I | A strong maple aroma with pumpkin-like and slightly spicy undertones |
| (structure) and (structure) | A fruity, anisic aroma with a raspberry undertone; on dry-out, fruity and berry-like. |

-continued

| Structure | Fragrance Profile |
|---|---|
| produced according to Example II 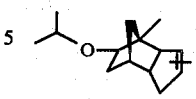 produced according to Examples III, IV and V. | A woody, resinous, camphoraceous patchouli-like aroma reminiscent of patchouli alcohol; with oakmoss undertones then green, and woody and floral and rosey topnotes. |
| 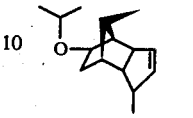 produced according to Example VI. | A fatty, slightly minty and camphoraceous aroma with pith-like and pumpkin nuances as well as woody and piney undertones. |
| 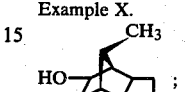 produced according to Example VII. | A green, fruity, creamy, rhubarb stem-like and banana-like aroma. |
| 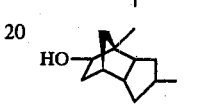 produced according to Example VIII. | A strong, herbaceous aroma with an oily and spicey, green, basil undertone. |
| 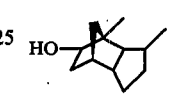 produced according to Example IX. | A low keyed fruity (banana), spicey (cinnamic), green aroma with sweaty and creamy undertones. |

-continued

| Structure | Fragrance Profile |
|---|---|
| 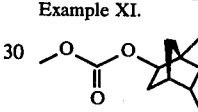 produced according to Example X. | A bitter, sweet, herbal, petitgrain-like, lavender and bergamot aroma profile with floral undertones. |
| 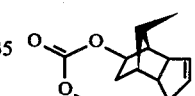 produced according to Example XI. | A minty, spicey, fruity aroma with caryophyllene-like, cedarwood and sandalwood undertones becoming borneol-woody-like on a dry-out. |
| 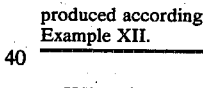 produced according to Example XII. | A fruity (apple), anisic-like aroma with dry, hay-like and berry-like undertones. |

What is claimed is:

1. An organometallic compound defined according to the structure:

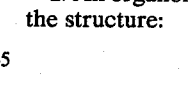

wherein M is selected from the group consisting of sodium, potassium and lithium.

2. A mixture of organometallic compounds defined according to the structure:

wherein M is selected from the group consisting of sodium, potassium and lithium.

* * * * *